US011998755B2

(12) United States Patent
Charles et al.

(10) Patent No.: US 11,998,755 B2
(45) Date of Patent: *Jun. 4, 2024

(54) HEAD-MOUNTABLE ADJUSTABLE DEVICES FOR GENERATING MAGNETIC FIELDS

(71) Applicant: Wave Neuroscience, Inc., Newport Beach, CA (US)

(72) Inventors: Robert Andrew Charles, New Boston, NH (US); Daniel Ernest Hamilton, Mt. Vernon, NH (US); Derek John Hugger, Goffstown, NH (US); James W. Phillips, Fountain Valley, CA (US); Jacob Wenner Eisner, San Francisco, CA (US); Jeffrey Alan Kessler, San Francisco, CA (US); Aaron Soloway, San Francisco, CA (US); Peter Scott MacDonald, Palo Alto, CA (US)

(73) Assignee: WAVE NEUROSCIENCE, INC., Newport Beach, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 17/067,523

(22) Filed: Oct. 9, 2020

(65) Prior Publication Data

US 2021/0170190 A1   Jun. 10, 2021

Related U.S. Application Data

(63) Continuation of application No. 15/935,482, filed on Mar. 26, 2018, now Pat. No. 10,835,754, which is a
(Continued)

(51) Int. Cl.
*A61N 2/12*  (2006.01)
*A61B 5/369* (2021.01)
(Continued)

(52) U.S. Cl.
CPC ............... *A61N 2/12* (2013.01); *A61B 5/369* (2021.01); *A61N 2/006* (2013.01); *A61N 2/06* (2013.01); *A61B 5/374* (2021.01)

(58) Field of Classification Search
CPC ...... A61B 5/0476; A61B 5/048; A61N 2/006; A61N 2/12; A61N 2/06
See application file for complete search history.

(56) References Cited

U.S. PATENT DOCUMENTS 3,821,949 A   7/1974   Hartzell et al.
4,727,857 A   3/1988   Hoerl
(Continued)

FOREIGN PATENT DOCUMENTS

DE   3417773 A1    2/1985
DE   29821635 U1   7/1999
(Continued)

OTHER PUBLICATIONS

Angelakis E., et al., "EEG Neurofeedback: A Brief Overview and an Example of Peak Alpha Frequency Training for Cognitive Enhancement in the Elderly," The Clinical Neuropsychologist, Jan. 2006, vol. 21 (1), 20 pages.
(Continued)

*Primary Examiner* — Thaddeus B Cox
*Assistant Examiner* — Joshua Daryl D Lannu
(74) *Attorney, Agent, or Firm* — Buchalter, a Professional Corporation

(57) ABSTRACT

Helmets for applying a magnetic field to the head of a subject, comprising: a housing comprising a concave surface configured to receive a portion of the head of the subject; a motor coupled to one or more of: a first permanent magnet via a first axle along a first axis of rotation, wherein the first axle drives movement of the first magnet; a second magnet via a second axle along a second axis of rotation wherein the
(Continued)

second axle drives movement of the second magnet; and a third magnet via a third axle along the third axis of rotation wherein the third axle drives movement of the third magnet, wherein the axes are parallel; and a fit mechanism comprising a adjuster coupled to the first magnet, wherein movement of the adjustor moves the first magnet independently of the second or the third magnet.

20 Claims, 22 Drawing Sheets

Related U.S. Application Data continuation of application No. 15/583,802, filed on May 1, 2017, now Pat. No. 9,962,555.

(60) Provisional application No. 62/484,579, filed on Apr. 12, 2017, provisional application No. 62/447,361, filed on Jan. 17, 2017.

(51) Int. Cl.
*A61B 5/374* (2021.01)
*A61N 2/00* (2006.01)
*A61N 2/06* (2006.01)

(56) References Cited

U.S. PATENT DOCUMENTS

| | | |
|---|---|---|
| 5,036,858 A | 8/1991 | Carter et al. |
| 5,092,835 A | 3/1992 | Schurig et al. |
| 5,409,445 A | 4/1995 | Rubins |
| 5,453,072 A | 9/1995 | Anninos et al. |
| 5,496,258 A | 3/1996 | Anninos et al. |
| 5,632,720 A | 5/1997 | Kleitz |
| 5,667,469 A | 9/1997 | Zhang et al. |
| 5,691,324 A | 11/1997 | Sandyk |
| 5,697,883 A | 12/1997 | Anninos et al. |
| 5,707,334 A | 1/1998 | Young |
| 5,769,778 A | 6/1998 | Abrams et al. |
| 5,788,624 A | 8/1998 | Lu et al. |
| 5,817,000 A | 10/1998 | Souder |
| 5,935,054 A | 8/1999 | Loos |
| 5,954,629 A | 9/1999 | Yanagidaira et al. |
| 6,001,055 A | 12/1999 | Souder |
| 6,083,252 A | 7/2000 | King et al. |
| 6,157,278 A | 12/2000 | Katznelson et al. |
| 6,194,852 B1 | 2/2001 | Lovatt et al. |
| 6,231,497 B1 | 5/2001 | Souder |
| 6,234,953 B1 | 5/2001 | Thomas et al. |
| 6,238,333 B1 | 5/2001 | Loos |
| 6,266,556 B1 | 7/2001 | Ives et al. |
| 6,290,638 B1 | 9/2001 | Canedo et al. |
| 6,402,678 B1 | 6/2002 | Fischell et al. |
| 6,463,328 B1 | 10/2002 | John |
| 6,488,617 B1 | 12/2002 | Katz |
| 6,537,197 B1 | 3/2003 | Ruohonen et al. |
| 6,648,812 B2 | 11/2003 | Ardizzone |
| 6,663,557 B2 | 12/2003 | Werny |
| 6,679,825 B2 | 1/2004 | Alicea |
| 6,978,179 B1 | 12/2005 | Flagg et al. |
| 7,033,312 B2 | 4/2006 | Rohan et al. |
| 7,102,144 B2 | 9/2006 | Matsuda et al. |
| 7,258,659 B2 | 8/2007 | Anninou et al. |
| 7,282,021 B2 | 10/2007 | Rohan et al. |
| 7,297,100 B2 | 11/2007 | Thomas et al. |
| 8,465,408 B2 | 6/2013 | Phillips et al. |
| 8,475,354 B2 | 7/2013 | Phillips et al. |
| 8,480,554 B2 | 7/2013 | Phillips et al. |
| 8,585,568 B2 | 11/2013 | Phillips et al. |
| 8,870,737 B2 | 10/2014 | Phillips et al. |
| 8,888,672 B2 | 11/2014 | Phillips et al. |
| 8,888,673 B2 | 11/2014 | Phillips et al. |
| 8,926,490 B2 | 1/2015 | Phillips et al. |
| 8,961,386 B2 | 2/2015 | Phillips et al. |
| 9,015,057 B2 | 4/2015 | Phillips et al. |
| 9,272,159 B2 | 3/2016 | Phillips et al. |
| 9,308,387 B2 | 4/2016 | Phillips et al. |
| 9,446,259 B2 | 9/2016 | Phillips et al. |
| 9,456,784 B2 | 10/2016 | Helekar et al. |
| 9,649,502 B2 | 5/2017 | Phillips et al. |
| 9,713,729 B2 | 7/2017 | Phillips et al. |
| 9,962,555 B1 * | 5/2018 | Charles ............ A61B 5/369 |
| 10,065,048 B2 | 9/2018 | Phillips et al. |
| 10,835,754 B2 * | 11/2020 | Charles ............ A61N 2/06 |
| 2002/0007128 A1 | 1/2002 | Ives et al. |
| 2002/0147380 A1 | 10/2002 | Ardizzone |
| 2002/0153015 A1 | 10/2002 | Garibaldi et al. |
| 2002/0183587 A1 | 12/2002 | Dormer |
| 2003/0093028 A1 | 5/2003 | Spiegel |
| 2004/0138578 A1 | 7/2004 | Pineda et al. |
| 2004/0143296 A1 | 7/2004 | Wang et al. |
| 2004/0210102 A1 | 10/2004 | van Mullekom |
| 2005/0043774 A1 | 2/2005 | Devlin et al. |
| 2005/0070778 A1 | 3/2005 | Lackey et al. |
| 2005/0107654 A1 | 5/2005 | Riehl |
| 2005/0107655 A1 | 5/2005 | Holzner |
| 2005/0118266 A1 | 6/2005 | Khan et al. |
| 2005/0118286 A1 | 6/2005 | Suffin et al. |
| 2005/0124847 A1 | 6/2005 | Ardizzone et al. |
| 2005/0124848 A1 | 6/2005 | Holzner |
| 2005/0154426 A1 | 7/2005 | Boveja et al. |
| 2005/0182287 A1 | 8/2005 | Becker |
| 2005/0187423 A1 | 8/2005 | Ardizzone et al. |
| 2005/0228209 A1 | 10/2005 | Schneider et al. |
| 2005/0256539 A1 | 11/2005 | George et al. |
| 2006/0015153 A1 | 1/2006 | Gliner et al. |
| 2006/0058572 A1 | 3/2006 | Anninou et al. |
| 2006/0094924 A1 | 5/2006 | Riehl |
| 2006/0149119 A1 | 7/2006 | Wang |
| 2006/0161039 A1 | 7/2006 | Juliana et al. |
| 2006/0189866 A1 | 8/2006 | Thomas et al. |
| 2006/0212090 A1 | 9/2006 | Lozano et al. |
| 2006/0217781 A1 | 9/2006 | John |
| 2006/0258950 A1 | 11/2006 | Hargrove et al. |
| 2006/0287566 A1 * | 12/2006 | Zangen ............ A61N 2/006 600/15 |
| 2007/0004957 A1 | 1/2007 | Hilburg |
| 2007/0100389 A1 | 5/2007 | Jaax et al. |
| 2007/0106170 A1 | 5/2007 | Dunseath, Jr. et al. |
| 2007/0142874 A1 | 6/2007 | John |
| 2007/0179558 A1 | 8/2007 | Gliner et al. |
| 2007/0191727 A1 | 8/2007 | Fadem |
| 2007/0203390 A1 | 8/2007 | Rohan et al. |
| 2007/0208209 A1 | 9/2007 | Holcomb |
| 2007/0282156 A1 | 12/2007 | Konings |
| 2008/0009772 A1 | 1/2008 | Tyler et al. |
| 2008/0046013 A1 | 2/2008 | Lozano |
| 2008/0081941 A1 | 4/2008 | Tononi |
| 2008/0125669 A1 | 5/2008 | Suffin et al. |
| 2008/0262287 A1 | 10/2008 | Dussau |
| 2009/0082690 A1 * | 3/2009 | Phillips ............ A61B 5/24 600/9 |
| 2009/0083071 A1 | 3/2009 | Phillips et al. |
| 2009/0198144 A1 | 8/2009 | Phillips et al. |
| 2009/0204015 A1 | 8/2009 | Phillips et al. |
| 2010/0185042 A1 | 7/2010 | Schneider et al. |
| 2011/0034822 A1 | 2/2011 | Phillips et al. |
| 2011/0112427 A1 | 5/2011 | Phillips et al. |
| 2011/0118536 A1 | 5/2011 | Phillips et al. |
| 2011/0137104 A1 | 6/2011 | Phillips et al. |
| 2013/0144107 A1 | 6/2013 | Phillips et al. |
| 2013/0144108 A1 | 6/2013 | Phillips et al. |
| 2013/0150650 A1 | 6/2013 | Phillips et al. |
| 2014/0121446 A1 | 5/2014 | Phillips et al. |
| 2014/0163305 A1 | 6/2014 | Watterson |
| 2014/0276182 A1 * | 9/2014 | Helekar ............ A61B 5/4064 600/15 |
| 2016/0045756 A1 | 2/2016 | Phillips et al. |
| 2017/0120066 A1 | 5/2017 | Phillips et al. |
| 2017/0312536 A1 | 11/2017 | Phillips et al. |

(56) References Cited

U.S. PATENT DOCUMENTS

| | | |
|---|---|---|
| 2018/0126184 A1 | 5/2018 | Phillips et al. |
| 2018/0229049 A1 | 8/2018 | Phillips et al. |

FOREIGN PATENT DOCUMENTS

| | | |
|---|---|---|
| EP | 2197534 A1 | 6/2010 |
| EP | 2498857 A1 | 9/2012 |
| WO | 9615829 A2 | 5/1996 |
| WO | 9629114 A1 | 9/1996 |
| WO | 03058518 A2 | 7/2003 |
| WO | 2007067148 A1 | 6/2007 |
| WO | 2008074707 A1 | 6/2008 |
| WO | 2009036040 A1 | 3/2009 |
| WO | 2009042718 A1 | 4/2009 |
| WO | 2009042720 A1 | 4/2009 |
| WO | 2009042721 A1 | 4/2009 |
| WO | 2009042722 A1 | 4/2009 |
| WO | 2011017466 A1 | 2/2011 |
| WO | 2011059986 A1 | 5/2011 |
| WO | 2018136431 A1 | 7/2018 |

OTHER PUBLICATIONS

Anninos P., et al., "MEG Evaluation of Parkinson's Diseased Patients After External Magnetic Stimulation," Acta Neurologica Belgica, 2007, vol. 107, pp. 5-10.

Anninos P.A., et al., "Nonlinear Analysis of Brain Activity in Magnetic Influenced Parkinson Patients," Brain Topography, 2000, vol. 13 (2), pp. 135-144.

"Applied Signal Processing," Retrieved from Internet: http://users.abo.fi/htoivone/courses/sbappl/aspchapter1.pdf, 2004, pp. 1-20.

Arns M., et al., "Potential Differential Effects of 9 Hz rTMS and 10 Hz rTMS in the Treatment of Depression," Letter to the Editor, Brain Stimulation, 2010, vol. 3, pp. 124-126.

Blum D.E., "Computer-Based Electroencephalography: Technical Basics, Basis for New Applications, and Potential Pitfalls," Electroencephalography and Clinical Neurophysiology, 1998, vol. 106, pp. 118-126.

Discovery Science: Transcranial Magnetic Stimulation Treatment for Addiction, Autism, Depression (Dr. Yi Jin) from PopSci's Future of Pleasure originally broadcast, Oct. 26, 2009, Retrieved from URL: http://www.youtube.com/watch?v=E3tPuB31CYc, Dec. 16, 2011.

Dr Jin Y., "The Future of the Brain," First Annual Brain and Behavior Symposium, Retrieved from URL: http://neurosciencecenter.brooksideinstitute.com/2007.sub.-symposium.sub-.-03Speaker.asp, Jun. 8, 2007, pp. 1-11.

Gasquet I., et al., "Pharmacological Treatment and Other Predictors of Treatment Outcomes in Previously Untreated Patients With Schizophrenia: Results From the European Schizophrenia Outpatient Health Outcomes (SOHO) Study," International Clinical Psychopharmacology, 2005, vol. 20 (4), pp. 199-205.

"Gaussian Peak Fit VI—LabVIEW 2009 Help," National Instruments, Jun. 2009, 4 pages.

Hamidi M., et al., "Repetitive Transcranial Magnetic Stimulation Affects Behavior by Biasing Endogenous Cortical Oscillations," Frontiers in Integrative Neuroscience, Jun. 24, 2009, vol. 3 (14), pp. 1-12.

Jin Y., et al., "Alpha EEG Predicts Visual Reaction Time," International Journal of Neuroscience, Sep. 1, 2006, vol. 116 (9), pp. 1035-1044.

Jin Y., et al., "Therapeutic Effects of Individualized Alpha Frequency Transcranial Magnetic Stimulation (Alpha TMS) on the Negative Symptoms of Schizophrenia," Schizophrenia Bulletin, 2006, vol. 32 (3), pp. 556-561.

Klimesch W., et al., "EEG Alpha Oscillations: The Inhibition-Timing Hypothesis," Brain Research Reviews, 2007, vol. 53, pp. 63-88.

Klimesch W., et al., "Enhancing Cognitive Performance With Repetitive Transcranial Magnetic Stimulation at Human Individual Alpha Frequency," European Journal of Neuroscience, 2003, vol. 17, pp. 1129-1133.

Leuchter A.F., et al., "The Relationship Between Brain Oscillatory Activity and Therapeutic Effectiveness of Transcranial Magnetic Stimulation in the Treatment of Major Depressive Disorder," Frontiers in Human Neuroscience, Feb. 26, 2013, vol. 7 (37), pp. 1-12.

"MERT: Magno-EEG Resonant Therapy," Retrieved from Internet: http://neurosciencecenter.brook-sideinstitute.com/mertfaq.asp, http://web.archive.org/web/20080514214345, http://neurosciencecenter.brooksideinstitute.com/mert.asp, http://web.archive.org/web/20080514161113, http:/web.archive.org/web/20080509095813, Aug. 29, 2007, pp. 1-5.

Myung I.J., "Tutorial on Maximum Likelihood Estimation," Journal of Mathematical Psychology, 2003, vol. 47, pp. 90-100.

O'Haver T., "Curve Fitting C: Non-Linear Iterative Curve Fitting," Retrieved from URL: http://web.archive.org/web/20090606121639/http://terpconnect.umd.ed-u/about.toh/spectrum/CurveFittingC.html, Jun. 6, 2009, pp. 1-5.

"Real-Time Filtering in BioExplorer," Retrieved from Internet: http://web.archive.org/web/20070125020332/, http://www.brain-trainer.com/Fi- ltering.pdf, Jan. 25, 2007, pp. 1-7.

Sauseng P., et al., "Spontaneous Locally Restricted EEG Alpha Activity Determines Cortical Excitability in the Motor Cortex," Neuropsychologia, 2009, vol. 47, pp. 284-288.

Triggs W.J., et al., "Effects of Left Frontal Transcranial Magnetic Stimulation on Depressed Mood, Cognition, and Corticomotor Threshold," Society of Biological Psychiatry, 1999, vol. 45, pp. 1440-1446.

"What is TMS?," Retrieved from the Internet: http://web.archive.org/web/20101014023718/ http://braintreatmentcenter.com/tms.html; and http://www.braintreatmentcenter.com/addiction., Jun. 8, 2011, pp. 1-3.

Communication for European Application No. 08833077.4, dated May 23, 2016, 6 pages.

Co-pending of U.S. Appl. No. 12/237,304, filed Sep. 24, 2008, 93 pages.

Co-pending of U.S. Appl. No. 13/893,171, filed May 13, 2013, 132 pages.

Co-pending of U.S. Appl. No. 14/827,107, filed Aug. 14, 2015, 80 pages.

Co-pending of U.S. Appl. No. 15/232,692, filed Aug. 9, 2016, 149 pages.

Co-pending of U.S. Appl. No. 15/486,428, filed Apr. 13, 2017, 76 pages.

Extended European Search Report for European Application No. 08833077.4, dated Jan. 5, 2011, 10 pages.

Extended European Search Report for European Application No. 10830602.8, dated Jun. 30, 2016, 11 pages.

Extended European Search Report for European Application No. 18160327.5, dated Oct. 24, 2018, 13 pages.

International Preliminary Report on Patentability for International Application No. PCT/US2008/077569, dated Mar. 30, 2010, 7 pages.

International Preliminary Report on Patentability for International Application No. PCT/US2008/077571, dated Mar. 30, 2010, 9 pages.

International Preliminary Report on Patentability for International Application No. PCT/US2008/077573, dated Mar. 30, 2010, 11 pages.

International Preliminary Report on Patentability for International Application No. PCT/US2008/077575, dated Mar. 30, 2010, 8 pages.

International Preliminary Report on Patentability for International Application No. PCT/US2010/044465, dated Feb. 16, 2012, 7 pages.

International Preliminary Report on Patentability for International Application No. PCT/US2010/056075, dated May 24, 2012, 8 pages.

International Preliminary Report on Patentability for International Application No. PCT/US2018/013903, dated Aug. 1, 2019, 14 pages.

(56) References Cited

OTHER PUBLICATIONS

International Search Report and Written Opinion for International Application No. PCT/US2008/077569, dated Jan. 26, 2009, 8 pages.
International Search Report and Written Opinion for International Application No. PCT/US2008/077571, dated Nov. 21, 2008, 9 pages.
International Search Report and Written Opinion for International Application No. PCT/US2008/077573, dated Nov. 24, 2008, 12 pages.
International Search Report and Written Opinion for International Application No. PCT/US2008/077575, dated Dec. 9, 2008, 8 pages.
International Search Report and Written Opinion for International Application No. PCT/US2010/044465, dated Sep. 29, 2010, 8 pages.
International Search Report and Written Opinion for International Application No. PCT/US2010/056075, dated Mar. 14, 2011, 11 pages.
International Search Report and Written Opinion for International Application No. PCT/US2018/013903, dated May 15, 2018, 16 pages.
Office Action for Japanese Application No. 2017008983, dated Nov. 27, 2017, 2 pages.
Office Action for U.S. Appl. No. 12/237,304, dated Feb. 12, 2015, 18 pages.
Office Action for U.S. Appl. No. 12/237,304, dated Jan. 6, 2017, 12 pages.
Office Action for U.S. Appl. No. 12/237,304, dated Jul. 3, 2012, 13 pages.
Office Action for U.S. Appl. No. 12/237,304, dated Jul. 8, 2016, 8 pages.
Office Action for U.S. Appl. No. 12/237,304, dated Oct. 8, 2015, 16 pages.
Office Action for U.S. Appl. No. 12/237,304, dated Oct. 10, 2017, 12 pages.
Office Action for U.S. Appl. No. 14/827,107, dated Aug. 31, 2018, 10 pages.
Office Action for U.S. Appl. No. 15/232,692, dated Dec. 14, 2017, 30 pages.
Office Action for U.S. Appl. No. 15/583,802, dated Aug. 28, 2017, 27 pages.
Office Action for U.S. Appl. No. 15/634,351, dated Sep. 10, 2018, 11 pages.

* cited by examiner

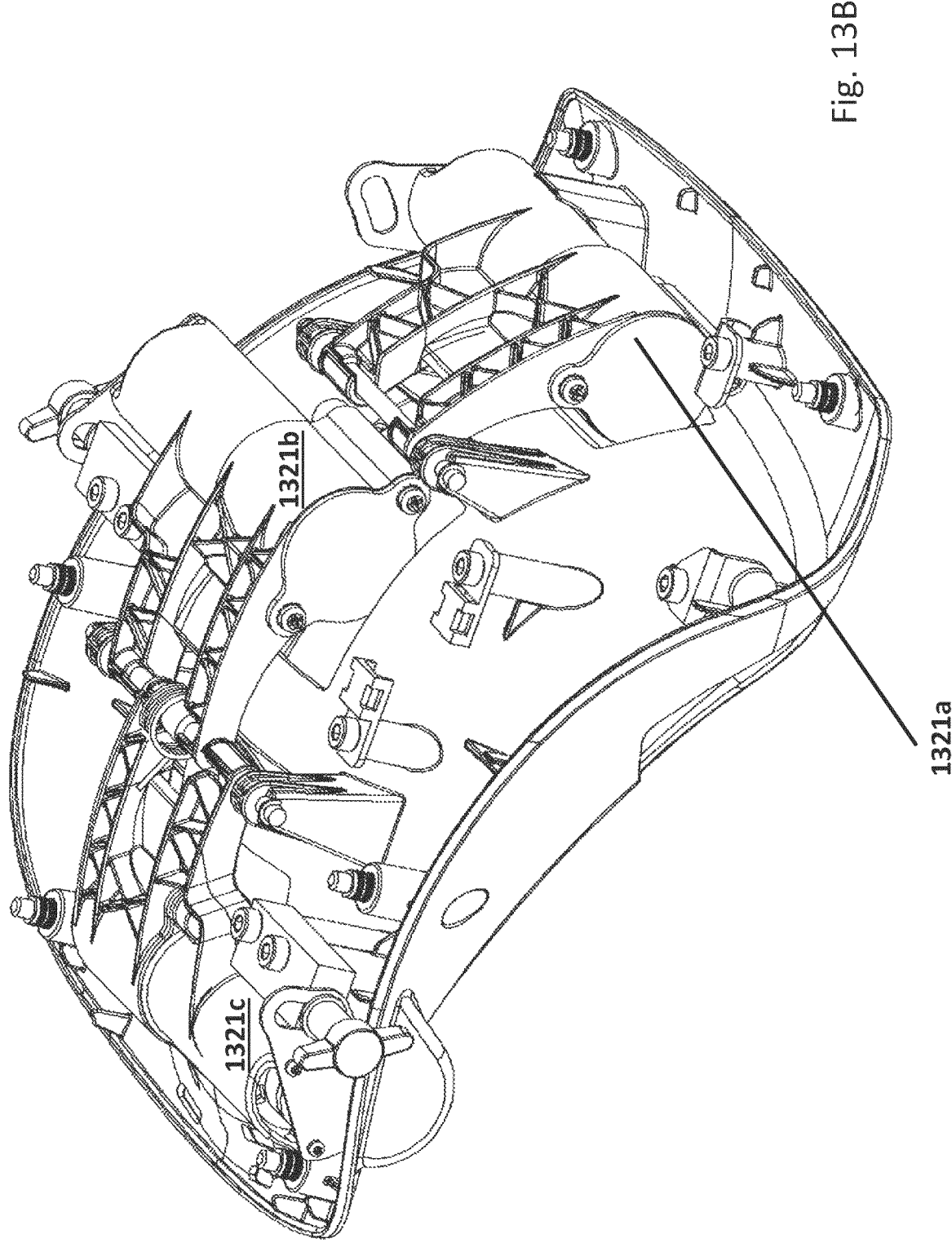

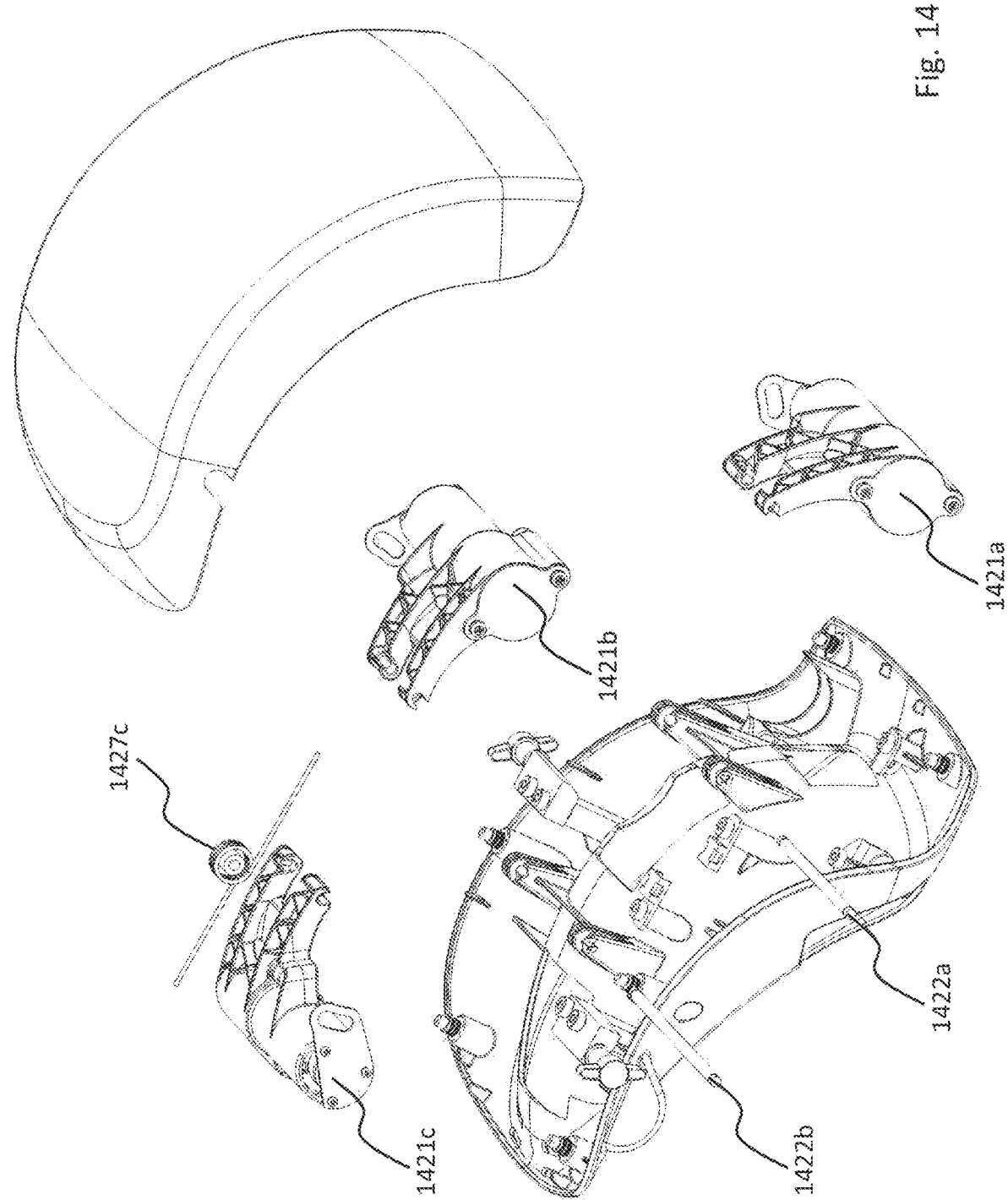

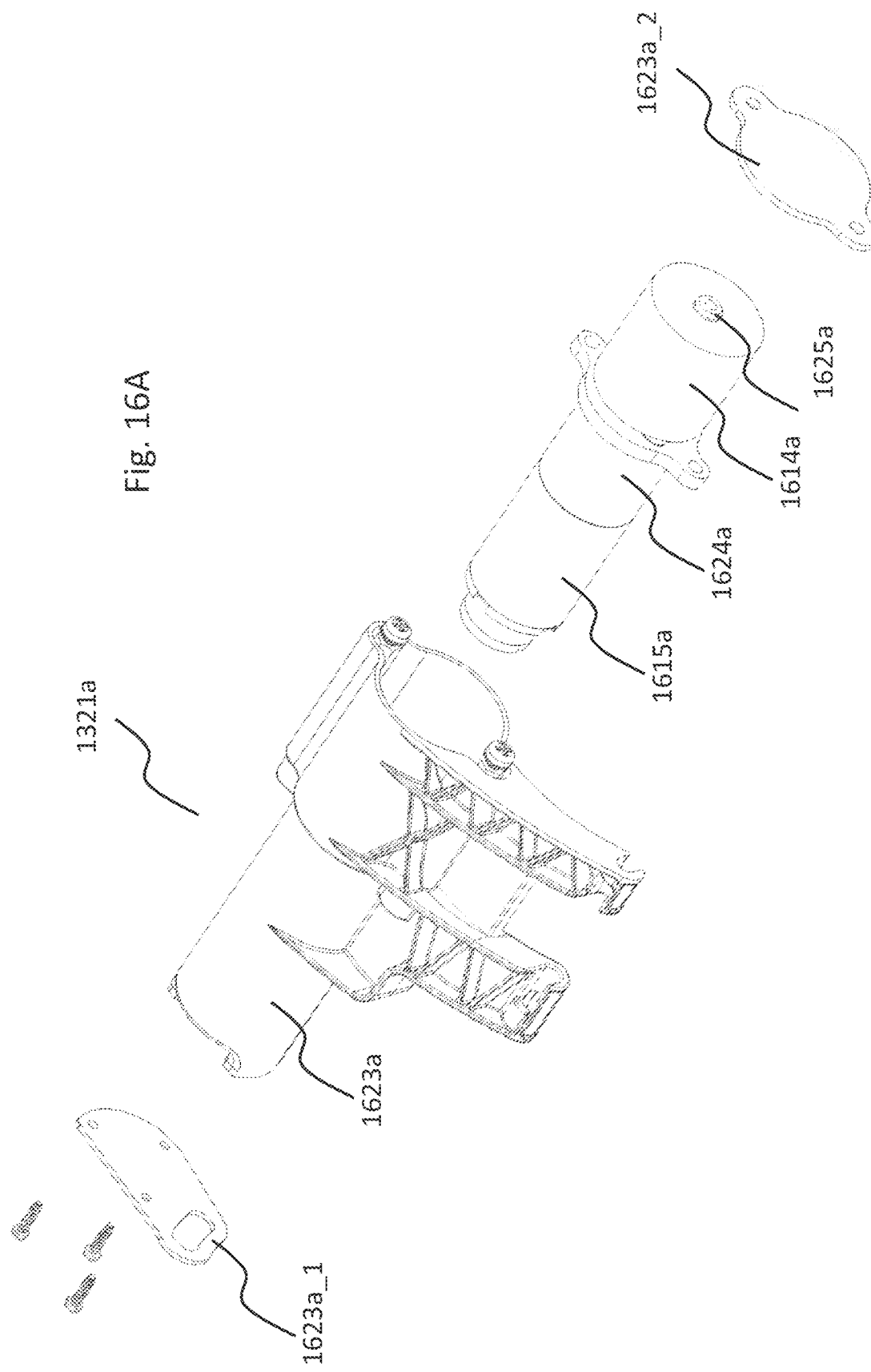

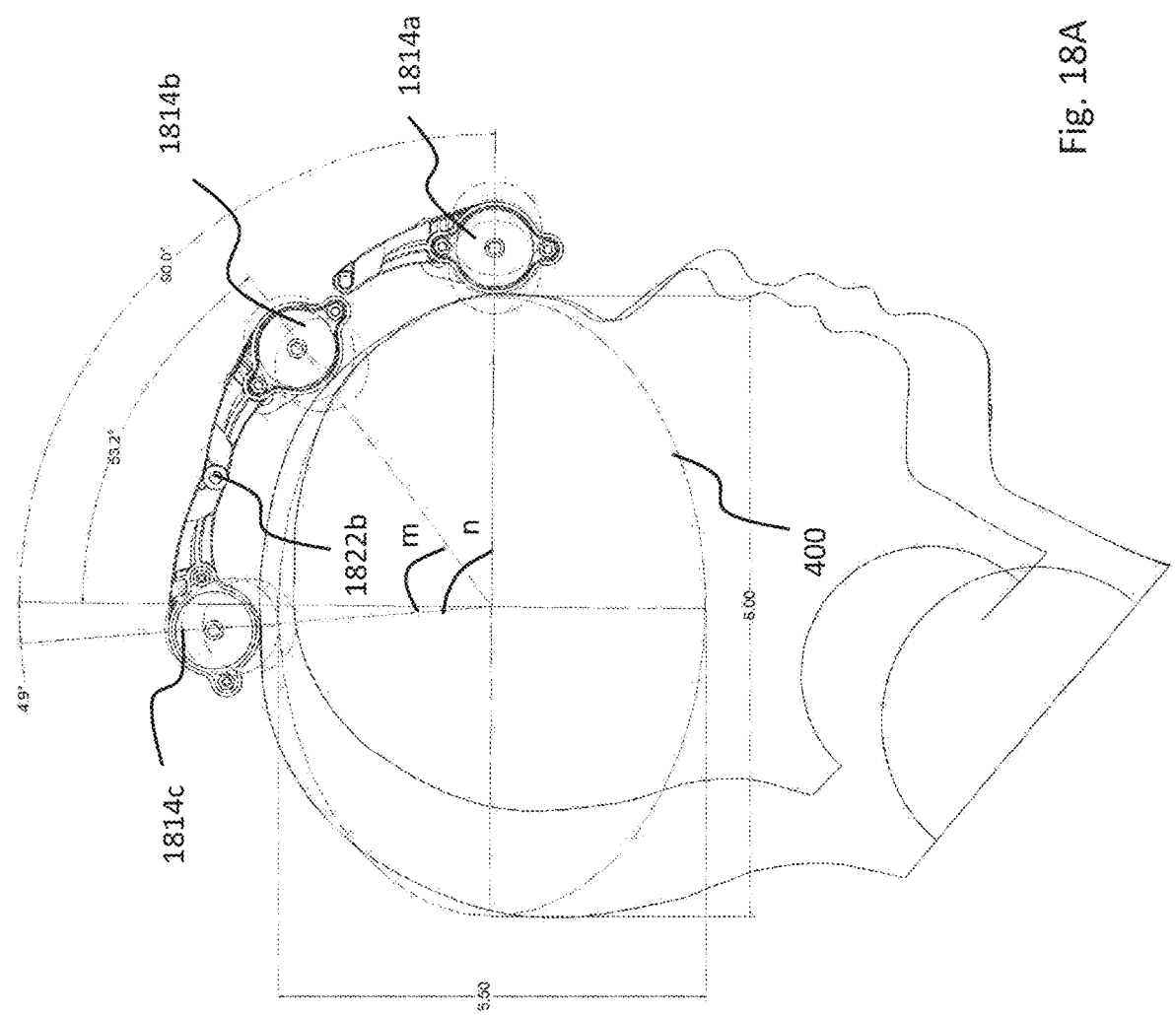

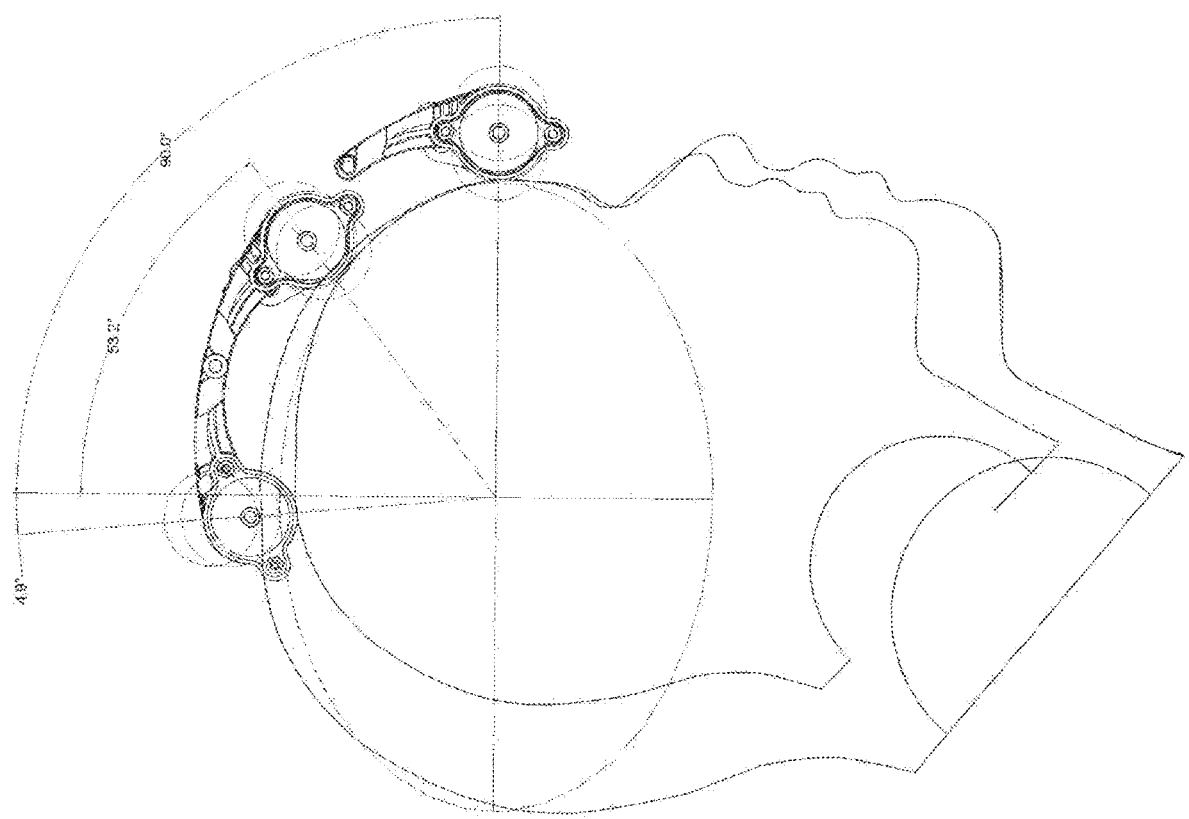

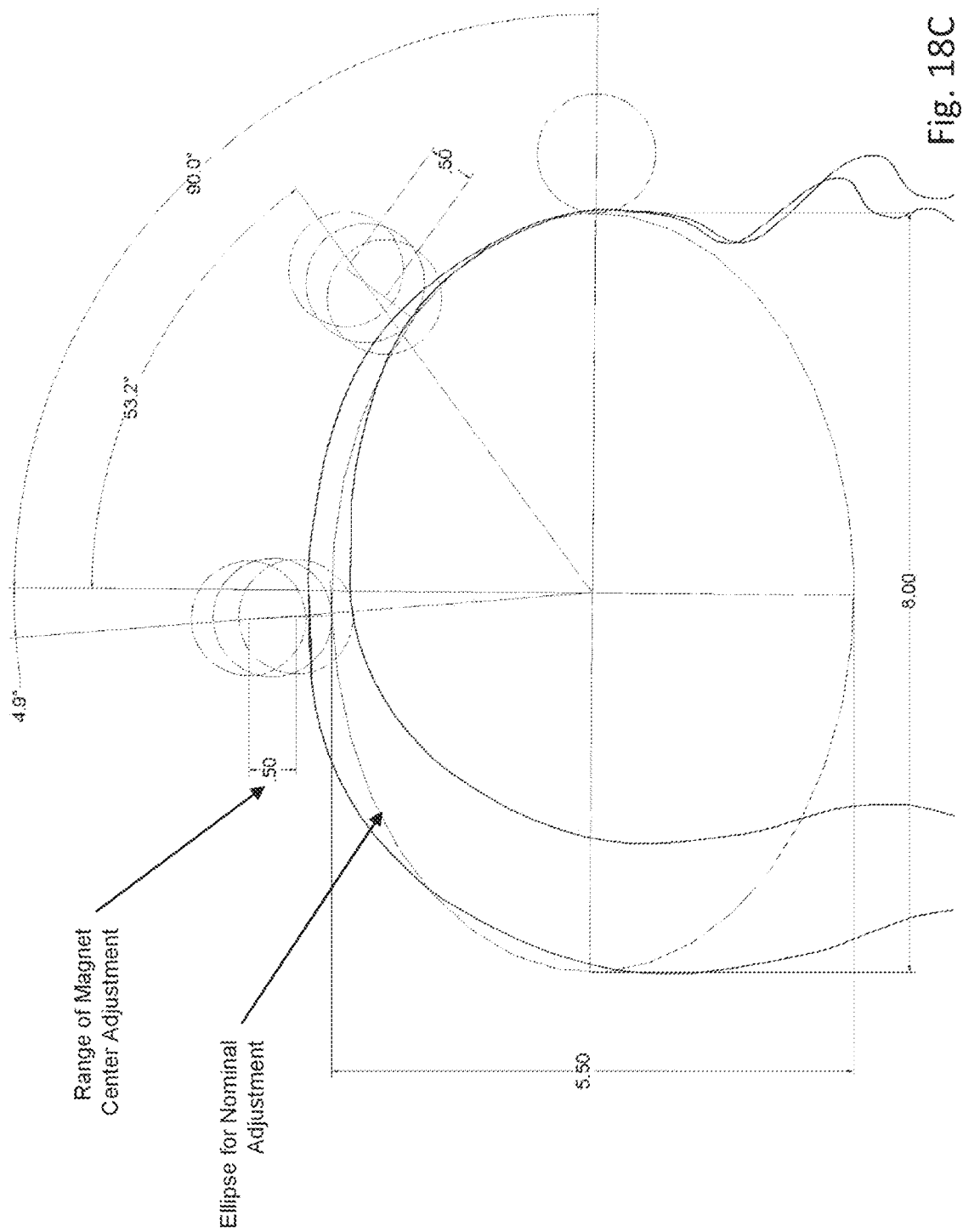

HEAD-MOUNTABLE ADJUSTABLE DEVICES FOR GENERATING MAGNETIC FIELDS

CROSS-REFERENCE TO RELATED APPLICATIONS

The present application is a continuation of U.S. patent application Ser. No. 15/583,802, filed May 1, 2017, entitled "HEAD-MOUNTABLE ADJUSTABLE DEVICES FOR GENERATING MAGNETIC FIELDS", which is a nonprovisional application of, and claims the benefit of, U.S. Provisional Application No. 62/447,361, filed on Jan. 17, 2017, and U.S. Provisional Application No. 62/484,579, filed on Apr. 12, 2017, which the entire contents of each are incorporated herein by reference.

BACKGROUND OF THE INVENTION

Mental disorders generate serious problems for the affected people, their families, and society. Currently, psychiatrists and neurophysiologists treat these disorders with a variety of medications, many of which have significant negative side effects. Treatment of these disorders with magnetic fields may generate positive therapeutic responses. Magnetic fields, especially varying magnetic fields can be generated by movement of one or more magnets.

SUMMARY OF THE INVENTION

Existing solutions of devices for generating magnetic fields lack capability in individual and independent adjustments of magnets of the devices, thus, current solutions are not optimized and customized to generate a varying magnetic field with customized degrees of freedom and variability, for example, tuning of the varying magnetic field strength at different locations in a three-dimensional space relative to the head of the subject. Further, traditional devices for generating magnetic fields fail to enable portable, wearable solutions in combination with individual and independent adjustments of magnets. Yet further, traditional devices fail to control and tune magnetic field characteristics via movement changes of a magnet assembly, for example, via varying rotational directions of a magnet array including multiple magnets. The head-mountable device or helmet as disclosed herein solves the above-mentioned problems of existing devices. Described herein, in some embodiments, are portable head-mountable devices or helmets for novel, inexpensive, wearable, easy to use generation of magnetic fields to a head of a subject. Described herein, in some embodiments, are head-mountable devices or helmets configurable to treat mental disorders that involve no medication. Described herein, in some embodiments, are wearable devices on a subject's head, portable for usage at various locations. Described herein, in some embodiments, are helmets with fit mechanisms that individually and independently adjust a position of a magnet within the helmet relative to the head of the subject. Such fit mechanism allows generation of a magnetic field with much finer tuning and more flexible adjustment over a three-dimensional space than traditional solutions. Disclosed herein, in some embodiments, are magnets that rotate in opposite directions in order to optimize and customize the magnetic field generated thereby to generate magnetic fields with a larger dynamic range in variability than existing devices.

Provided herein is a device comprising a helmet for applying a magnetic field to a head of a subject, comprising: a housing comprising a concave surface configured to receive at least a portion of the head of the subject; a magnet assembly within said housing comprising: a first motor coupled to one or more of: a first permanent magnet via a first axle along a first axis of rotation, wherein the first axle is configured to drive movement of the first permanent magnet; a second permanent magnet via a second axle along a second axis of rotation wherein the second axle is configured to drive movement of the second permanent magnet; and a third permanent magnet via a third axle along a third axis of rotation wherein the third axle is configured to drive movement of the third permanent magnet, wherein the first axis, the second axis, and the third axis are substantially parallel to each other; and a first fit mechanism comprising a first adjuster coupled to the first permanent magnet, wherein movement of the first adjustor moves the first permanent magnet independently of the second permanent magnet or the third permanent magnet relative to the head of the subject. In some embodiments, said housing comprises a first motor coupled to one or more of: a first permanent magnet via a first axle having a first axis of rotation, wherein the first axle is configured to drive movement of the first permanent magnet; a second permanent magnet via a second axle having a second axis of rotation wherein the second axle is configured to drive movement of the second permanent magnet; and a third permanent magnet via a third axle having a third axis of rotation wherein the third axle is configured to drive movement of the third permanent magnet, In some embodiments, the first adjuster is accessible to a user or the subject when the housing is positioned on the head of the subject. In some embodiments, the first fit mechanism reversibly moves the first permanent magnet, with a range of movement of the first permanent magnet no greater than about 13.0 mm. In some embodiments, minimal adjustment allowable by the first fit mechanism is no greater than about 0.1 mm. In some embodiments, the first fit mechanism reversibly moves the first permanent magnet by about 0.01 inches to about 0.5 inches. In some embodiments, adjustment by the first fit mechanism is manual. In some embodiments, adjustment by the first fit mechanism is automatic. In some embodiments, the first fit mechanism comprises a feedback receiver that receives a position feedback from a height measurement element, the height measurement element configured to measure the distance from the first permanent magnet to the head of the subject. In some embodiments, the first fit mechanism comprises a processor and a computer readable media executable by the processor to control the movement of the first adjuster based on the position feedback. In some embodiments, the first fit mechanism comprises a processor and a computer readable media executable by the processor to control the movement of the first permanent magnet based on the position feedback In some embodiments, the first fit mechanism comprises: a first adjuster movable relative to said housing, movement of the first adjuster causes height adjustment of the first axle and thereby adjustment of the first magnet relative to said housing; a fastening element attached to said housing, the fastening element configured to fasten the first axle and thereby the first permanent magnet at a height; a limiter configured to limit a height adjustment within a pre-selected range; a height measurement element configured to measure a distance from the first permanent magnet to the head of the subject; or a combination thereof. In some embodiments, the first adjuster is a knob, a lever, a buckle with adjustable straps or a screw mechanism. In some embodiments, the first adjuster is a knob, a lever, a buckle with adjustable straps, a screw mechanism, or any combination thereof. In some embodiments, the first fit mechanism does not extend outside of said housing in a closed configuration and wherein the first adjuster within said housing is accessible to a user or the subject from outside of said housing. In some embodiments, part of the first fit mechanism extends outside of said housing in a closed configuration such that it is accessible to a user or the subject. In some embodiments, the part comprises a first adjuster. In some embodiments, the first adjuster extends outside of said housing in a closed configuration such that it is accessible to a user or the subject. In some embodiments, at least part of the first fit mechanism is not accessible to a user or the subject from outside of said housing when the helmet is in a closed configuration. In some embodiments, a second and third adjuster is a knob, a lever, a buckle with adjustable straps or a screw mechanism. In some embodiments, the device as disclosed herein comprises a second fit mechanism comprising a second adjuster coupled to the second permanent magnet, wherein movement of the second adjuster moves the second permanent magnet independently of the first permanent magnet or third permanent magnet relative to the head of the subject. In some embodiments, the second adjuster is accessible to the user or the subject when the housing is positioned on the head of the subject. In some embodiments, the device further comprises a second fit mechanism comprising a second adjuster coupled to the second permanent magnet, wherein the second adjuster is accessible to the user or the subject when the housing is positioned on the head of the subject, and wherein movement of the second adjuster moves the second permanent magnet independently of the first permanent magnet or third permanent magnet relative to the head In some embodiments, the second fit mechanism reversibly moves the second permanent magnet such that a distance from the second permanent magnet to the head of the subject is from about 0.1 millimeter to about 50.0 millimeters. In some embodiments, the device comprises a third fit mechanism comprising a third adjuster coupled to the third permanent magnet, wherein movement of the third adjuster moves the third permanent magnet independently of the first permanent magnet or the second permanent magnet relative to the head of the subject. In some embodiments, the third adjuster is accessible to the user or the subject when the housing is positioned on the head of the subject. In some embodiments, the third fit mechanism reversibly moves the third permanent magnet such that a distance from the third permanent magnet to the head of the subject is from about 0.1 millimeter to about 50.0 millimeters. In some embodiments, the first permanent magnet is placed against a forehead of the subject. In some embodiments, the first permanent magnet is placed near a forehead of the subject, and wherein a distance between the first permanent magnet and the forehead is fixed upon placement of the helmet and wherein the third permanent magnet is positioned close to a top of the head of the subject, and wherein the second permanent magnet is positioned in between the first and the third permanent magnet upon placement of the helmet and wherein the first and the third permanent magnet rotate in a first direction, and wherein the second permanent magnet rotates in an opposite direction from the first rotation direction. In some embodiments, a distance between the first permanent magnet and the forehead is fixed upon placement of the helmet. In some embodiments, the third permanent magnet is positioned close to a top of the head of the subject. In some embodiments, the second permanent magnet is positioned in between the first and the third permanent magnet upon placement of the helmet. In some embodiments, the first and the third permanent magnet rotate in a first direction. In some embodiments, the second permanent magnet rotates in an opposite direction from the first rotation direction. In some embodiments, the rotational axis of the first permanent magnet is the first axle, the rotational axis of the second permanent magnet is the second axle, and the rotational axis of the third permanent magnet is the third axle. In some embodiments, poles of said first and third permanent magnets are aligned. In some embodiments, poles of said first, second, and third permanent magnets are aligned. In some embodiments, neutral planes of said first and third permanent magnets are aligned. In some embodiments, neutral planes of said first, second, and third permanent magnets are aligned. In some embodiments, neutral planes of two or more of said first, second, and third permanent magnets are aligned. In some embodiments, the term "aligned" when used in reference to two or more neutral planes means that the planes are substantially parallel. In some embodiments, the first fit mechanism adjusts a distance between the first motor and the head. In some embodiments, the first fit mechanism adjusts a distance between the first motor and the head of the subject. In some embodiments, part of said first, second or third permanent magnets is configured to extend outside of said housing. In some embodiments, the first, second, or third permanent magnet remains within the said housing. In some embodiments, frequency of movement of said permanent magnets is identical. In some embodiments, a frequency of a movement of said first, second, and third permanent magnets is identical. In some embodiments, the device is portable. In some embodiments, the device is of portable size and weight. In some embodiments, the device weights less than about 9.9 pounds or less than about 4.5 kg. In some embodiments, the helmet comprises a maximal dimension of less than about 40 centimeters, the maximal dimension being a width, a length, a diameter, or a diagonal of the helmet. In some embodiments, the device comprises a maximal volume of less than about 0.064 cubic meters. In some embodiments, the helmet comprises a maximal dimension of less than about 40 centimeters, the maximal dimension being a width, a length, a diameter, or a diagonal of the helmet, or wherein the helmet comprises a maximal volume of less than about 0.064 cubic meters. In some embodiments, said housing is reversibly transformable between a closed configuration and an open configuration. In some embodiments, the device comprises padding between the concave surface and the head of the subject. In some embodiments, the portion includes a region of a frontal lobe, a parietal lobe, or both of the subject. In some embodiments, the portion includes a region of a forehead, a top of head, or both of the subject. In some embodiments, said permanent magnets are spaced apart from each other by a preselected distance. In some embodiments, the preselected distance is adjustable. In some embodiments, the device comprises a connection to a controller, wherein the controller controls the first fit mechanism. In some embodiments, the controller controls the first motor and thereby the frequency of movement of one or more of said permanent magnets. In some embodiments, the connection is a wired connection, a wireless connection, or both. In some embodiments, the controller is not within the helmet. In some embodiments, the controller is not physically attached to the helmet. In some embodiments, the controller comprises a processor and computer readable media executable by the processor. In some embodiments, the controller comprises a user interface. In some embodiments, the controller comprises an interface to receive a non-transitory computer-readable media. In some embodiments, the controller comprises a wireless connection, or a wire connection to an Internet. In some embodiments, the controller comprises a second processor and computer readable media executable by the second processor configured to: collect EEG data of the subject; receive the EEG data of the subject; store the EEG data of the subject; calculate the intrinsic frequency using the EEG data of the subject; calculate the Q-factor of the intrinsic frequency using the EEG data of the subject; or a combination thereof. In some embodiments, the device comprises a connection to a power source. In some embodiments, the power source is rechargeable. In some embodiments, the power source is within the helmet. In some embodiments, the device comprises a fastening element that is configured to fasten the concave surface relative to the head of the subject. In some embodiments, the fastening element is an adjustable headband. In some embodiments, each of said permanent magnets has a magnetic field strength of about 1 Gauss to about 3 Tesla (30,000 Gauss).

Provided herein are devices for applying a magnetic field to the head of the subject, comprising: a housing comprising a concave surface configured to receive at least a portion of the head of the subject; and a magnet assembly within said housing comprising: a first permanent magnet configured to rotate about a first axis of rotation, a second permanent magnet configured to rotate about a second axis of rotation, a third permanent magnet configured to rotate about a third axis of rotation, wherein the first axis, the second axis, and the third axis are substantially parallel to each other; and a first motor drivingly coupled to one or more of the first, second, and third permanent magnets via one or more rotating axles; wherein two of said first, second, and third permanent magnets rotate in a first direction about their respective axes of rotation, and one of said first, second, and third permanent magnets rotates in a second direction about its axis of rotation, wherein the second direction is opposite to the first direction. In some embodiments, the device comprises a first fit mechanism comprising a first adjuster coupled to the first permanent magnet, wherein movement of the first adjustor moves the first permanent magnet independently of the second permanent magnet or the third permanent magnet relative to the head of the subject. In some embodiments, the first adjuster is accessible to a user or the subject when the housing is positioned on the head of the subject. In some embodiments, the first fit mechanism reversibly moves the first permanent magnet, range of movement of the first permanent magnet no greater than about 13.0 mm. In some embodiments, the first fit mechanism reversibly moves the first permanent magnet, range of movement of the first permanent magnet no greater than about 0.5 inches. In some embodiments, minimal adjustment allowable by the first fit mechanism is no greater than about 0.1 mm. In some embodiments, adjustment by the first fit mechanism is manual. In some embodiments, adjustment by the first fit mechanism is automatic. In some embodiments, the first fit mechanism comprises a feedback receiver that receives a position feedback from a height measurement element, the height measurement element configured to measure the distance from the first permanent magnet to the head of the subject. In some embodiments, the first fit mechanism comprises a processor and a computer readable media executable by the processor to control the movement of the first adjuster based on the position feedback. In some embodiments, the first fit mechanism comprises a processor and a computer readable media executable by the processor to control the movement of the first permanent magnet based on the position feedback. In some embodiments, the first fit mechanism comprises: a first adjuster movable relative to said housing, movement of the first adjuster causes height adjustment of the first axle thereby adjustment of the first magnet relative to said housing; a fastening element attached to said housing, the fastening element configured to fasten the first axle thereby the first permanent magnet at a height; a limiter configured to limit a height adjustment within a pre-selected range; a height measurement element configured to measure a distance from the first permanent magnet to the head of the subject; or a combination thereof. In some embodiments, the first adjuster is a knob, a lever, a buckle with adjustable straps or a screw mechanism. In some embodiments, the first fit mechanism does not extend outside of said housing in a closed configuration and wherein the first adjustor within said housing is accessible to a user or the subject from outside of said housing. In some embodiments, part of the first fit mechanism extends outside of said housing in a closed configuration such that it is accessible to a user or the subject. In some embodiments, the part comprises a first adjuster. In some embodiments, at least part of the first fit mechanism is not accessible to a user or the subject from outside of said housing when the housing is in a closed configuration. In some embodiments, the device comprises a second fit mechanism comprising a second adjuster coupled to the second permanent magnet, wherein movement of the second adjustor moves the second permanent magnet independently of the first permanent magnet or third permanent magnet relative to the head of the subject. In some embodiments, the second adjuster is accessible to the user or the subject when the housing is positioned on the head of the subject. In some embodiments, the second fit mechanism reversibly moves the second permanent magnet such that a distance from the second permanent magnet to the head of the subject is from about 0.1 millimeter to about 50.0 millimeters. In some embodiments, the device comprises a third fit mechanism comprising a third adjuster coupled to the third permanent magnet, wherein movement of the third adjustor moves the third permanent magnet independently of the first permanent magnet or the second permanent magnet relative to the head of the subject. In some embodiments, the third adjuster is accessible to the user or the subject when the housing is positioned on the head of the subject. In some embodiments, the third fit mechanism reversibly moves the third permanent magnet such that a distance from the third permanent magnet to the head of the subject is from about 0.1 millimeter to about 50.0 millimeters. In some embodiments, the first permanent magnet is placed against a forehead of the subject. In some embodiments, a distance between the first permanent magnet and the forehead is fixed upon placement of the helmet. In some embodiments, the third permanent magnet is positioned close to a top of the head of the subject. In some embodiments, the second permanent magnet is positioned in between the first and the third permanent magnet upon placement of the helmet. In some embodiments, the rotational axis of the first permanent magnet is a first axle, the rotational axis of the second permanent magnet is a second axle, and the rotational axis of the third permanent magnet is a third axle. In some embodiments, poles of said first and third permanent magnets are aligned. In some embodiments, poles of said first, second, and third permanent magnets are aligned. In some embodiments, neutral planes of said first and third permanent magnets are aligned. In some embodiments, neutral planes of said first, second, and third permanent magnets are aligned. In some embodiments, the first fit mechanism adjusts a distance between the first motor and the head. In some embodiments, part of said first, second or third permanent magnets is configured to extend outside of said housing. In some embodiments, the first, second, or third permanent magnet remains within the said housing. In some embodiments, frequency of movement of said permanent magnets is identical. In some embodiments, the device is portable. In some embodiments, the device is of portable size and weight. In some embodiments, the device weights less than 4.5 kg. In some embodiments, the helmet comprises a maximal dimension of less than about 40 centimeters, the maximal dimension being a width, a length, a diameter, or a diagonal of the helmet. In some embodiments, the helmet comprises a maximal volume of less than about 0.064 cubic meters. In some embodiments, said housing is reversibly transformable between a closed configuration and an open configuration. In some embodiments, the device comprises padding between the concave surface and the head of the subject. In some embodiments, the device comprises padding between a concave surface of the housing and the head of the subject In some embodiments, the portion includes a region of a frontal lobe, a parietal lobe, or both of the subject. In some embodiments, the portion includes a region of a forehead, a top of head, or both of the subject. In some embodiments, the portion includes a region of a frontal lobe, a parietal lobe a region of a forehead, a top of head, or any combination thereof of the subject. In some embodiments, said permanent magnets are spaced apart from each other by a preselected distance. In some embodiments, the preselected distance is adjustable. In some embodiments, said permanent magnets are spaced apart from each other by a preselected distance, and wherein the preselected distance is adjustable. In some embodiments, the device comprises a connection to a controller, wherein the controller controls the first fit mechanism. In some embodiments, the controller controls the first motor thereby frequency of movement of one or more of said permanent magnets. In some embodiments, the controller controls the first motor thereby affecting the frequency of movement of one or more of the said first, second, and third permanent magnets. In some embodiments, the connection is a wired connection, a wireless connection, or both. In some embodiments, the controller is not within the device. In some embodiments, the controller is not physically attached to the device. In some embodiments, the controller is not within the helmet or wherein the controller is not physically attached to the helmet In some embodiments, the controller comprises a processor and computer readable media executable by the processor. In some embodiments, the controller comprises a user interface. In some embodiments, the controller comprises an interface to receive a non-transitory computer-readable media. In some embodiments, the controller comprises a wireless connection, a wire connection to an Internet. In some embodiments, the controller comprises a second processor and computer readable media executable by the second processor configured to: collect EEG data of the subject; receive the EEG data of the subject; store the EEG data of the subject; calculate the intrinsic frequency using the EEG data of the subject; calculate the Q-factor of the intrinsic frequency using the EEG data of the subject; or a combination thereof. In some embodiments, the device comprises a connection to a power source. In some embodiments, the controller comprises a processor, computer readable media executable by the processor, a user interface, an interface to receive a non-transitory computer-readable media, a wireless connection, a wire connection to an Internet, a connection to a power source, or any combination thereof. In some embodiments, the power source is rechargeable. In some embodiments, the power source is within the device. In some embodiments, the helmet comprises a fastening element that is configured to fasten the concave surface relative to the head of the subject. In some embodiments, the helmet comprises a fastening element that is configured to fasten the helmet relative to the head of the subject. In some embodiments, the fastening element is an adjustable headband. In some embodiments, the fastening element comprises an adjustable headband. In some embodiments, each of said permanent magnets has a magnetic field strength of about 1 Gauss to about 3 Tesla (30,000 Gauss). In some embodiments, the device comprises an electroencephalogram (EEG). In some embodiments, the housing comprises a concave surface.

Provided herein is a method of applying a magnetic field to the head of a subject comprising: donning a helmet on the head of a subject; modifying the position of a permanent magnet within the helmet through a fit mechanism; rotating a permanent magnet about an axis. In some embodiments, modifying of the position of a permanent is performed manually, automatically, or any combination thereof. In some embodiments, the fit mechanism modifies the position of a permanent magnet by about 0.01 inches to about 0.5 inches. In some embodiments, the method comprises: a height measurement element measuring a distance from a permanent magnet to the head of the subject; a height measurement communicating the distance to a processor; the processor storing the distance; and the processor directing the fit mechanism to modify the position of a permanent magnet within the housing. In some embodiments, the method comprises: a user inputting data into a controller; the controller communicating the controller data to a processor; the processor storing the controller data; and the processor directing the fit mechanism to modify the position of a permanent magnet within the housing. In some embodiments, the method comprises: an EEG measuring the EEG data of the subject; the EEG transmitting the EEG data to a processor; the processor storing the EEG data; the processor calculating the intrinsic frequency from the EEG data; the processor calculating the Q-factor of the intrinsic frequency from the EEG data; and the processor directing the fit mechanism to modify the position of a permanent magnet within the housing.

A device comprising a helmet for applying a magnetic field to a head of a subject, the helmet comprising: a housing configured to receive at least a portion of the head of the subject; a magnet assembly within said housing comprising: a first motor coupled to one or more of: a first permanent magnet via a first axle having a first axis of rotation, wherein the first axle is configured to drive movement of the first permanent magnet; a second permanent magnet via a second axle having a second axis of rotation wherein the second axle is configured drive movement of the second permanent magnet; and a third permanent magnet via a third axle having a third axis of rotation wherein the third axle is configured drive movement of the third permanent magnet, wherein the first axis, the second axis, and the third axis are substantially parallel to each other; and a first fit mechanism comprising a first adjuster coupled to the first permanent magnet, wherein movement of the first adjustor moves the first permanent magnet independently of the second permanent magnet or the third permanent magnet relative to the head of the subject. The device of claim 1, wherein the first adjuster is accessible to a user or the subject when the housing is positioned on the head of the subject. In some embodiments, the first fit mechanism is configured to reversibly move the first permanent magnet by about 0.01 inches to about 0.5 inches. In some embodiments, the first fit mechanism comprises a feedback receiver that receives a position feedback from a height measurement element, wherein the height measurement element is configured to measure a distance from the first permanent magnet to the head of the subject and wherein the position feedback comprises the distance measured or other information based on the distance measured. In some embodiments, the first fit mechanism comprises a processor and a computer readable media executable by the processor to control the movement of the first adjuster based on the feedback. In some embodiments, the first fit mechanism comprises: a first adjuster movable relative to said housing, wherein movement of the first adjuster causes height adjustment of the first axle thereby adjustment of the first magnet relative to said housing; a fastening element attached to said housing, the fastening element configured to fasten the first axle thereby the first permanent magnet at a height; a limiter configured to limit a height adjustment within a pre-selected range; a height measurement element configured to measure a distance from the first permanent magnet to the head of the subject; or a combination thereof. In some embodiments, the first adjuster comprises: a knob; a lever; a buckle with adjustable straps; a screw mechanism; or any combination thereof. In some embodiments, the first adjuster extends outside of said housing in a closed configuration such that it is accessible to a user or the subject. Some embodiments, further comprise a second fit mechanism comprising a second adjuster coupled to the second permanent magnet, wherein the second adjuster is accessible to the user or the subject when the housing is positioned on the head of the subject, and wherein movement of the second adjuster moves the second permanent magnet independently of the first permanent magnet or third permanent magnet relative to the head of the subject by a distance of from about 0.1 millimeter to about 50.0 millimeters. Some embodiments, further comprise a third fit mechanism comprising a third adjuster coupled to the third permanent magnet, wherein the third adjuster is accessible to the user or the subject when the housing is positioned on the head of the subject, and wherein movement of the third adjuster moves the third permanent magnet independently of the first permanent magnet or the second permanent magnet relative to the head of the subject by a distance of from about 0.1 millimeter to about 50.0 millimeters. In some embodiments, the first permanent magnet is placed near a forehead of the subject, and wherein a distance between the first permanent magnet and the forehead is fixed upon placement of the helmet and wherein the third permanent magnet is positioned close to a top of the head of the subject, and wherein the second permanent magnet is positioned in between the first and the third permanent magnet upon placement of the helmet and wherein the first and the third permanent magnet rotate in a first direction, and wherein the second permanent magnet rotates in an opposite direction from the first rotation direction. In some embodiments, the north pole-south pole axes of two or more of said first, second, and third permanent magnets are aligned during rotational movements. In some embodiments, neutral planes of two or more of said first, second, and third permanent magnets are aligned. In some embodiments, the first fit mechanism adjusts a distance between the first motor and the head of the subject. In some embodiments, a frequency of a movement of said first, second, and third permanent magnets is identical. In some embodiments, the helmet weights less than about 4.5 kg. In some embodiments, the helmet comprises a maximal dimension of less than about 40 centimeters, the maximal dimension being a width, a length, a diameter, or a diagonal of the helmet, or wherein the helmet comprises a maximal volume of less than about 0.064 cubic meters. In some embodiments, said housing is reversibly transformable between a closed configuration and an open configuration. Some embodiments further comprise a padding between a concave surface of the housing and the head of the subject. In some embodiments, the portion includes a region of a frontal lobe, a parietal lobe a region of a forehead, a top of head, or any combination thereof of the subject. In some embodiments, said permanent magnets are spaced apart from each other by a preselected distance, and wherein the preselected distance is adjustable. Some embodiments further comprise a connection to a controller, wherein the controller controls the first fit mechanism. In some embodiments, the controller controls the first motor thereby affecting the frequency of movement of one or more of the said first, second, and third permanent magnets. In some embodiments, the connection is a wired connection, a wireless connection, or both. In some embodiments, the controller is not within the helmet or wherein the controller is not physically attached to the helmet. In some embodiments, the controller comprises a processor, computer readable media executable by the processor, a user interface, an interface to receive a non-transitory computer-readable media, a wireless connection, a wire connection to an Internet, a connection to a power source, or any combination thereof. In some embodiments, the controller further comprising a second processor and computer readable media executable by the second processor configured to: collect EEG data of the subject; receive the EEG data of the subject; store the EEG data of the subject; calculate the intrinsic frequency using the EEG data of the subject; calculate the Q-factor of the intrinsic frequency using the EEG data of the subject; or a combination thereof. Some embodiments further comprise a fastening element that is configured to fasten the helmet relative to the head of the subject. In some embodiments, the fastening element comprises an adjustable headband. In some embodiments, each of said permanent magnets has a magnetic field strength of about 1 Gauss to about 3 Tesla (30,000 Gauss).

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the systems and methods provided will be obtained by reference to the following detailed description that sets forth illustrative embodiments and the accompanying drawings of which:

FIG. 13B shows the head-mountable device of FIG. 12 with the upper housing part removed;

FIG. 14 shows the same exemplary embodiment of the head-mountable device of FIG. 12 with the upper housing part removed and magnet housings separated out and highlighted;

FIG. 16A-B shows an exemplary embodiment of a magnet and its assembly of a head-mountable device as in FIGS. 13A-B, and 14;

FIG. 18A shows an example of magnet position adjustments of a head-mountable device as disclosed herein to fit on a larger head of a patient;

FIG. 18B shows an example of magnet position adjustments of a head-mountable device as disclosed herein to fit on a smaller head of a patient; and FIG. 18C shows an example of ranges for magnet position adjustments of a head-mountable device as disclosed herein.

DETAILED DESCRIPTION OF THE INVENTION

Figure 1:
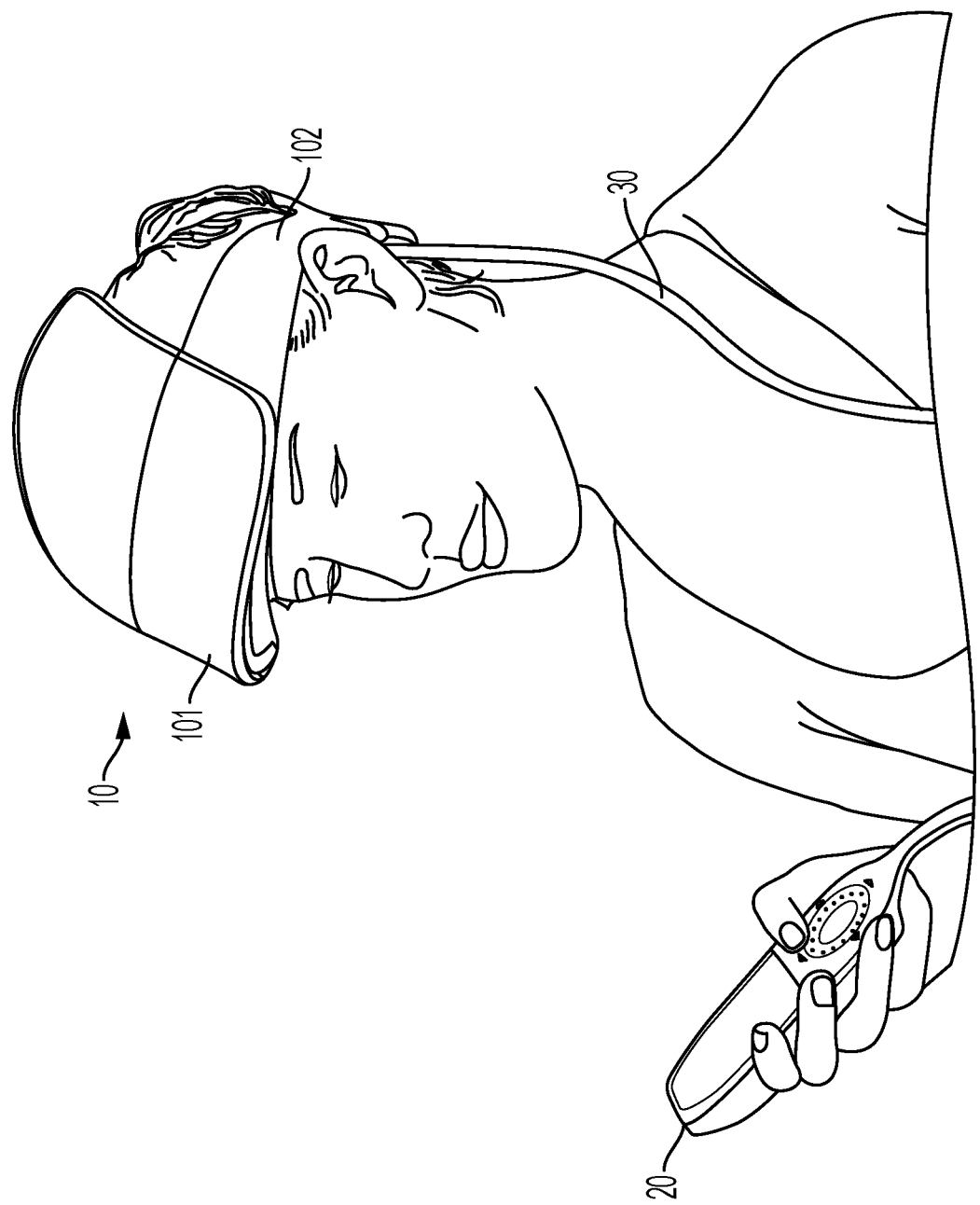
FIG. 1 shows an exemplary head-mountable device, in accordance with embodiments.
Figure 2:
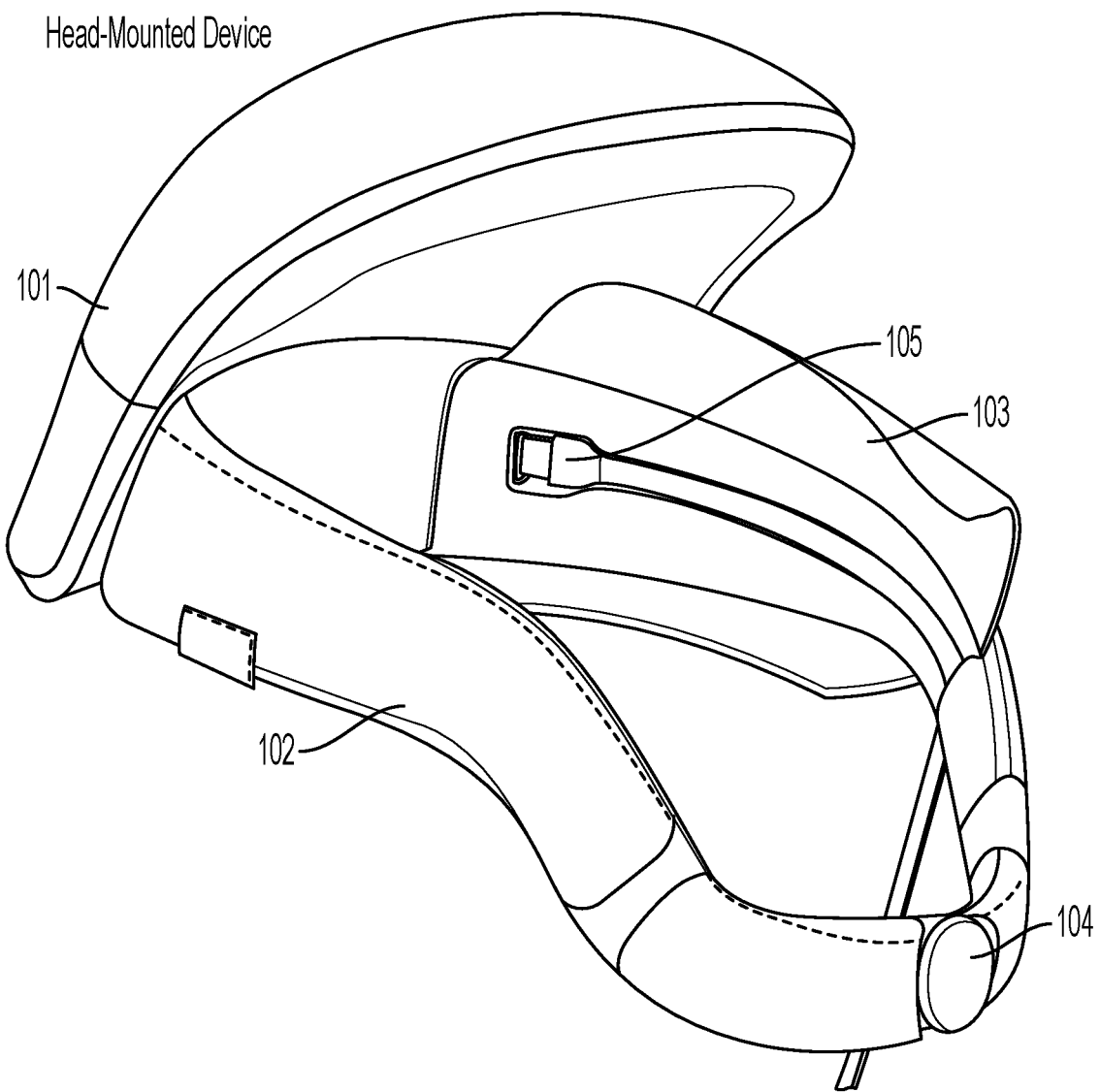
FIG. 2 shows an exemplary helmet of the exemplary head-mountable device of FIG. 1, in accordance with embodiments.

Existing solutions of devices for generating magnetic fields lack capability in individual and independent adjustments of magnets of the devices, thus, current solutions are not optimized and customized to generate a varying magnetic field with customized degrees of freedom and variability, for example, tuning of the varying magnetic field strength at different locations in a three-dimensional space relative to the head of the subject. Traditional devices for generating magnetic field fail to enable portable, wearable solutions in combination with individual and independent adjustments of magnets. Additionally, traditional devices fail to control and tune magnetic field characteristics via movement changes of a magnet assembly, for example, via varying rotational directions of a magnet array including multiple magnets. The head-mountable device or helmet as disclosed herein solves the above-mentioned problems of existing devices. Provided herein are portable head-mountable devices or helmets for novel, inexpensive, wearable, easy to use generation of magnetic fields to a head of a subject. Provided herein, in some embodiments, are head-mountable devices or helmets configurable to treat mental disorders that involve no medication. Provided herein, in some embodiments, are wearable devices on a subject's head, portable for usage at various locations. Provided herein, in some embodiments, are helmets with fit mechanisms that individually and independently adjust a position of a magnet of the helmets relative to the head of the subject. Such a fit mechanism allows generation of a magnetic field with much finer tuning and more flexible adjustment over a three-dimensional space than traditional solutions. Disclosed herein, in some embodiments, are magnets that rotate in opposite directions in order to optimize and customize the magnetic field generated thereby to generate magnetic field with a larger dynamic range in variability than existing devices.

Provided herein are helmets for applying a magnetic field to the head of the subject, comprising: a housing comprising a concave surface configured to receive at least a portion of the head of the subject; a magnet assembly within said housing comprising: a first motor coupled to one or more of: a first permanent magnet via a first axle along a first axis of rotation, wherein the first axle is configured to drive movement of the first permanent magnet; a second permanent magnet via a second axle along a second axis of rotation wherein the second axle is configured to drive movement of the second permanent magnet; and a third permanent magnet via a third axle along the third axis of rotation wherein the third axle is configured to drive movement of the third permanent magnet, wherein the first axis, the second axis, and the third axis are substantially parallel to each other; and a first fit mechanism comprising a first adjuster coupled to the first permanent magnet, wherein movement of the first adjustor moves the first permanent magnet independently of the second permanent magnet or the third permanent magnet relative to the head of the subject.

Provided herein are helmets for applying a magnetic field to the head of the subject, comprising: a housing comprising a concave surface configured to receive at least a portion of the head of the subject; and a magnet assembly within said housing comprising: a first permanent magnet configured to rotate about a first axis of rotation, a second permanent magnet configured to rotate about a second axis of rotation, a third permanent magnet configured to rotate about a third axis of rotation, wherein the first axis, the second axis, and the third axis are substantially parallel to each other; and a first motor drivingly coupled to one or more of the first, second, and third permanent magnets via one or more rotating axles; wherein two of said first, second, and third permanent magnets rotate in a first direction about their respective axes of rotation, and one of said first, second, and third permanent magnets rotates in a second direction about its axis of rotation, wherein the second direction is opposite to the first direction.

In some embodiments, the devices and methods disclosed herein include a head-mountable, wearable device, or helmet. As disclosed herein, head-mountable device, wearable device and helmets are equivalent terms. FIGS. 1-3 and 12 show embodiments of the wearable helmet 10, 1200. The helmet, or equivalently the head-mountable device, includes one piece of housing 1201 that fits to at least a part of a subject's scalp curvature 101. The housing has a predetermined three-dimensional shape or an adjustable three-dimensional shape in order to fit to a part of a scalp's curvature. The housing includes a lower part 107, 1307 that is placed between magnet(s) and rotor(s) 114a-114c and 115a-115c and the scalp. The lower part includes a concave surface. In some embodiments, the concave surface has a fixed three dimensional curvature defined by non-flexible materials. The non-flexible materials include plastic, polymer, or the like. The housing includes an upper part 106, 1206 that is placed above magnet(s) and rotor(s) and the scalp. The upper part and lower part form a same piece of housing. Alternatively, the housing only includes a lower part or an upper part. The upper part or lower part or both have a predetermined three-dimensional shape or an adjustable three-dimensional shape in order to fit to a part of a scalp's curvature. In some embodiments, the upper part or lower part or both have a predetermined three-dimensional shape or an adjustable three-dimensional shape in order to fit to a scalp from approximately the forehead to the top of the scalp of the wearer. In some embodiments, the upper part, lower part, or both have a predetermined three-dimensional shape or an adjustable three-dimensional shape in order to fit to a curvature surface of motor(s) and/or magnet(s). In some embodiments, the helmet has an open and/or a closed configuration. In its open configuration, in some case, the upper part and the lower part of the helmet are not mechanically attached or connected to each other. In some embodiments, the helmet is open when the majority of the magnet assemblies (magnets and rotor(s), shaft, and other units) are accessible to a user or a subject. In the closed configuration, in some embodiments, the upper part and the lower part of the helmet are mechanically attached or connected to each other or the majority of the magnet assembly is not accessible to a user or a subject. In some embodiments, the lower part includes flexible or deformable material as a cushion or a pad between the helmet and the scalp. Non-limiting examples include rubber, foam, plastic, metal, or the like. In some embodiments, the helmet has a closed configuration during its operation for protection of the element therewithin. As such, adjustments of the elements are arranged to be accessible when the helmet is in its closed position. For non-limiting examples, the magnets are arranged so that they are controlled to extend at least partially out from the lower part of the helmet for fit adjustment to a subject's scalp, and the magnet adjuster 1523 to loosen the magnets for adjustment is also positioned outside or assembled from outside of the helmet. In some embodiments, the helmet or elements therewithin comprise a shielding or the like to limit the directional or focused distribution of magnetic field(s) specifically to certain region of the scalp. In some embodiments, a custom fit headset is permanently adjusted to the patient. As an example, a helmet or use of the like is molded to fit the specific patient's head.

In some embodiments, a helmet includes an elastic element 111 selected from one or more of a cushion, a padding, a sponge, or any other elastic or resilient members for increasing comfort of the subject when the helmet is worn. These elastic or resilient members are consumable and replaceable. These members are optional.

In some embodiments, a helmet includes a fastening element 102, 1202 to fasten helmet to at least one portion of a scalp. The fastening of a helmet is reversible. Preferably, the fastening element is adjusted so that it allows the helmet to fit and be fastened on various locations of a scalp. In some embodiments, the fastening element is adjusted so that it fits and fasten the helmet to different subjects at various locations of their scalps. The fastening element includes a headband, a strap, an adjustment element, a connection, or a combination thereof. The adjustment element 104 is any adjustment element that is suitable to use on a conventional helmet, headband, head strap, chin strap, or the like. The connection is any connecting element that is suitable to use on a conventional helmet, headband, head strap, chin strap, or the like. As a non-limiting example, the adjustment element is a knob on the headband that is turned in two directions to adjust the tightness of fit. As another example, the adjustment element is a buckle with adjustable straps. In some embodiments, the adjustment element does not adjust individual magnet or motors independent of other magnet(s) or motor(s).

In some embodiments, the fastening element 102, 1202 is attached to the housing 101, 1201 of the helmet. In some embodiments, the fastening element is attached to the housing at any suitable locations. In some embodiments, the attachment location is adjusted by a user. In some embodiments, the attachment element is any suitable element that enables permanent or reversible attachment. In some embodiments, the fastening element is attached to the lower part of the housing 107, 1307 of the helmet so that a portion of it sits close to the forehead or the eyebrows of the wearer.

In some embodiments, a helmet includes a lighting element 112 for indication to a subject. A helmet includes an audio or a visual element for indication to the wearer. In some embodiments, the indication is related to the therapy, treatment, and/or a procedure. In some embodiments, the lighting source is located at a location of a helmet that is close to a wearer's eye. In some embodiments, the lighting source is located on a front rim or front edge of the helmet.

In some embodiments, the helmet 10, 1200 includes one or more selected from an upper housing 106, 1206, a magnet housing (110, 410, 510, 610, 1623*a*), a motor housing (110, 410, 510, 610), a head liner pad 111, a lower housing 107, 1207, a magnet assembly pivot 113, an adjustable strap 1228, a pivot pin for one or more magnets 1422*a*, 1422*b*, an adjuster 1523 for adjusting position of one or more magnets headband wrap 103, a removable head band 109, and a LED 112.

Figure 7:
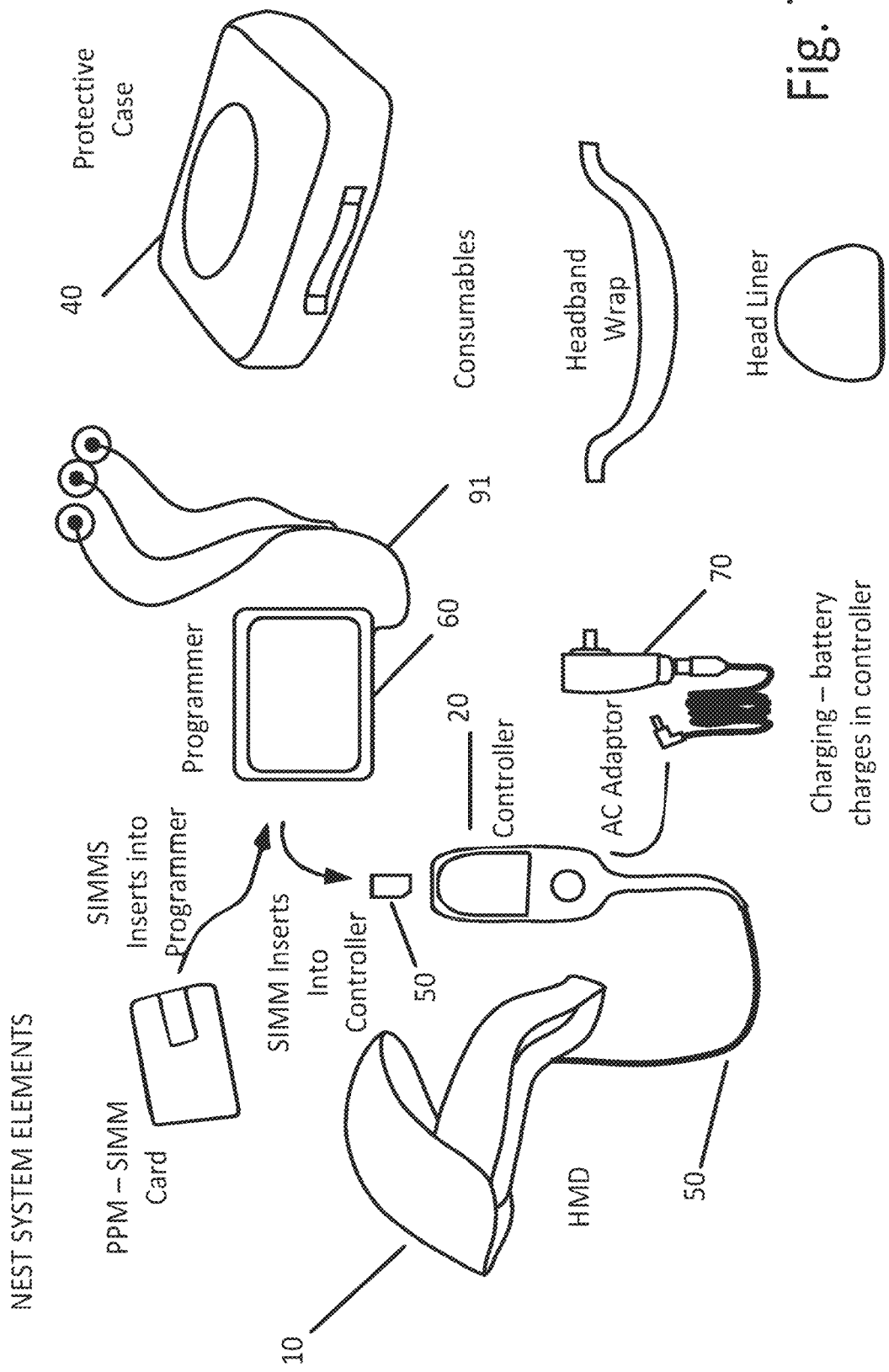
FIG. 7 shows an example of the head-mountable device and its system, in accordance with embodiments.

Another exemplary embodiment of the device as disclosed herein is shown in FIG. 7. The helmet 10 has an enclosure to fit at least part of three magnets therewithin. The magnets are adjustably fixed to the helmet mechanically via a fit mechanism. The helmet includes a concave surface that is positioned against a region of scalp of the subject. In some embodiments, the concave surface is made of a flexible material. In some embodiments, the concave surface is made of a non-flexible material with a flexible padding. The concave surface is adjustable to fit variations in human subject's head shape and/or size. In some embodiments, the concave surface has a fixed shape, size, or both that is not customized by a user.

In some embodiments, the helmet 10 and its supporting elements are of portable sizes. In some embodiments, the helmet and its supporting element are of portable weight. In some embodiments, the helmet is safe, easy and convenient to use without assistance from medical professionals. With the above advantages, the helmet as disclosed herein is used conveniently in places other than health care facilities. Non-limiting examples of places that the helmet is used includes home, office, hotel, vehicle, park, gym, campsite, library, or the like. The helmet is used when the subject stays still in a same location or in various motions. The helmet is used with a rechargeable power source. The helmet is used without a connection to an external power outlet. The helmet has a left-right symmetry or lateral symmetry to its shape.

In some embodiments, the motors and magnets reside in the headset 10, 1200 but the motor controllers and other system electronics reside external to the headset, for example, in the system controller as shown in FIG. 7. In further embodiments, the headset of the system and the external device controller 20 are connected via an electrical cable 30. The system controller includes the motor controllers, power supplies to convert AC electricity to DC electricity, a micro-controller to control the system, a display for human readable information, push-buttons to control the start and stop of therapy and/or other elements of the device. A USB port in the micro-controller accepts a flash drive with the patient therapy "prescription."

In some embodiments, the magnetic field disclosed herein is generated by the movement of permanent magnets. The magnetic field has a magnetic field strength. The field strength is measured at one or more treatment site of the head of the subject. The position of the helmet or individual magnets is adjusted such that the magnetic field strength at one or more selected treatment sites is at, below, or above a pre-determined value.

In some embodiments, various parameters of the magnetic fields generated by the helmet described herein are manipulated. These parameters include but are not limited to:

(a) the combined field strength at the treatment site, which is determined by the strength of the magnets used and the distance between the magnets and the subject's head;

(b) the frequency of the magnetic field, or the rate of change of the magnetic field, which is determined by movement of one or more magnets (as a non-limiting example, by the rotational speed at which at least one magnet rotates relative to the treatment area);

(c) the amplitude of the waveform (or the net change in magnetic flux) to which the treatment area is subjected to, and (d) the phase of the magnetic field between two (or more) magnets (i.e. the magnetic phase) when the magnetic field frequencies of the two (or more) magnets are the same (or substantially the same).

In some embodiments, the magnetic field is a combination of the magnetic field generated by individual magnets within the head-mountable device. In further embodiments, the magnetic field is a static or varying magnetic field. In further embodiments, the varying magnetic field has one or more parameters of the field changing over time. In further embodiments, the rate of variation of the magnetic field is determined by the movement of the magnets within the head-mountable device. In some embodiments, the magnetic field has a field strength within the range of about 0.1 Gauss to about 3 Tesla (30,000 Gauss).

For instance, the individual magnet field generated by one magnet or the combination magnetic field generated by all the magnets within the helmet is at or close to a frequency within a specific EEG band, for example, delta band (about 1-about 4 Hz), theta band (about 4-about 8 Hz), alpha band (about 8-about 13 Hz), and beta band (about 13-about 30 Hz). In some embodiments, the magnet field(s) includes one or more frequencies from within one or more EEG bands. Alternatively, the magnet field is at one or more frequencies within a range from about 1 Hz to about 100 Hz.

In some embodiments, the combined or individual magnetic field strength is below the threshold for undesired firing of neurons in the subject. In some case, the combined or individual magnetic field strength is below the threshold for heating up tissue of the subject within a predetermined period of time.

In some embodiments, a helmet 10, 1200 includes one or more magnet assemblies 1321a-c, and 1421a-c. Each assembly includes one or more of magnets, one or more of motors actuating the magnets, one or more gear boxes, and other elements.

Figure 3:
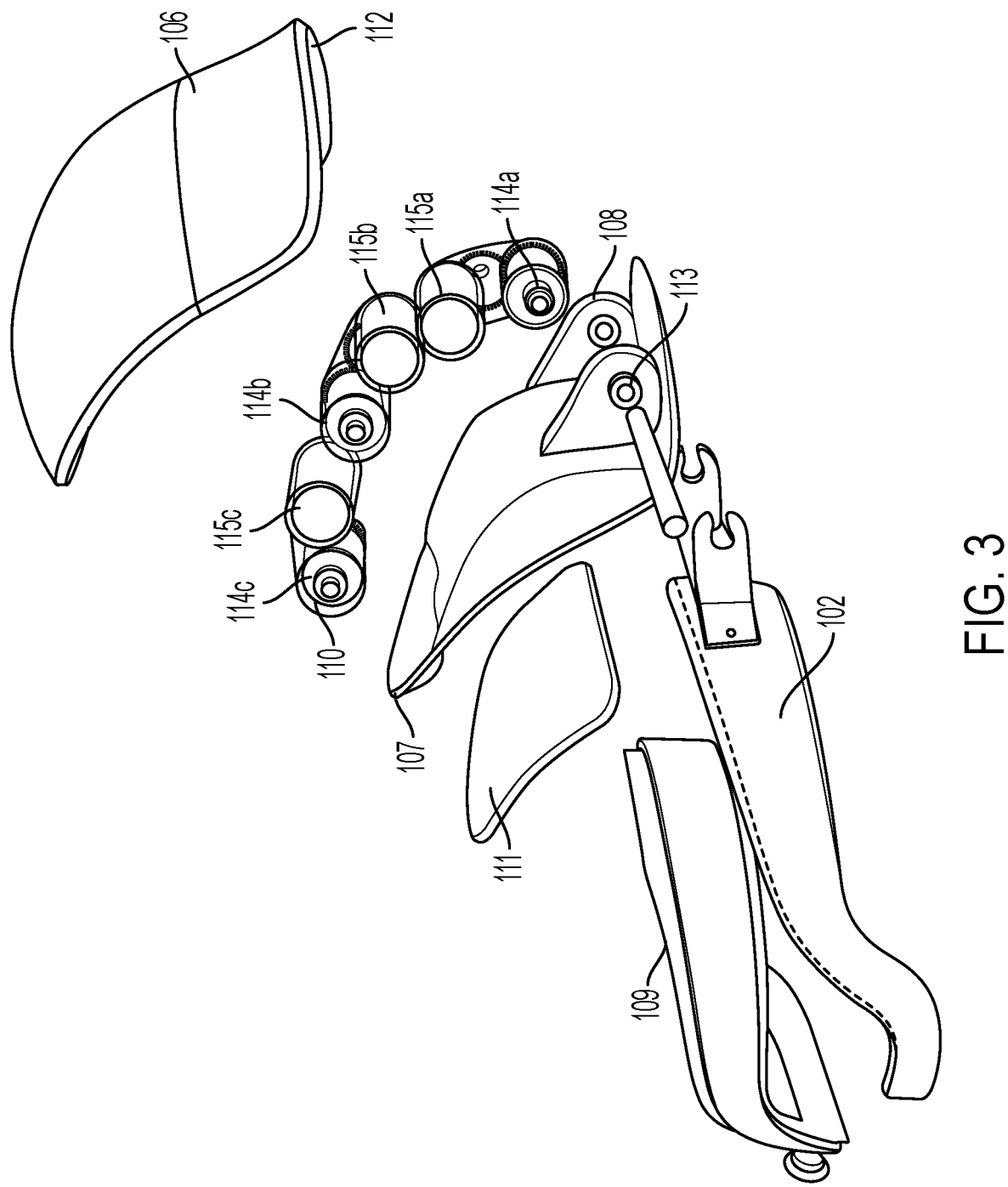
FIG. 3 shows the exemplary head-mountable device of FIG. 1, in accordance with embodiments.
Figure 4:
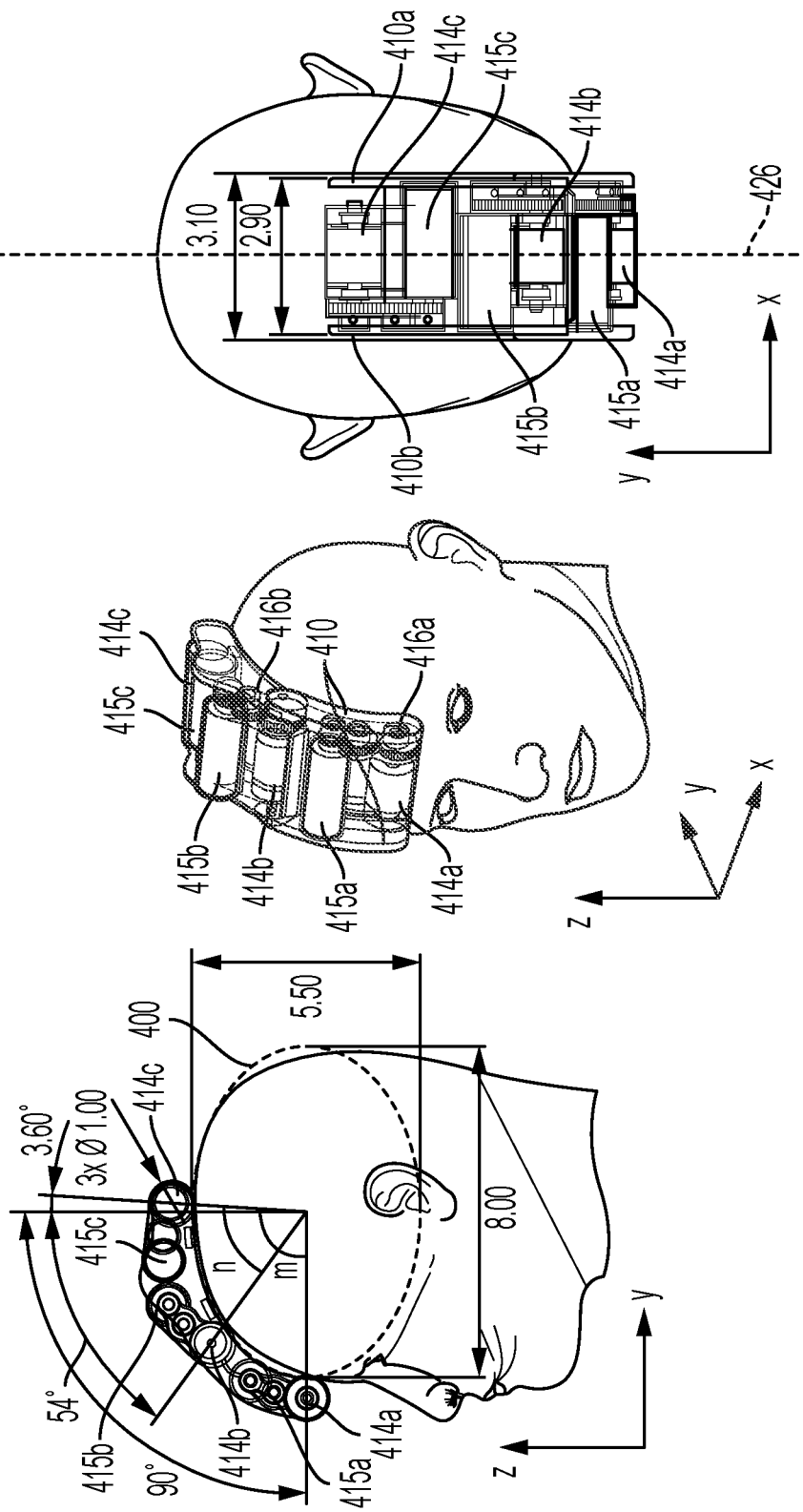
FIG. 4 shows an exemplary magnet assembly of a head mountable device, in accordance with embodiments.

Referring to FIGS. 3-4, in a particular embodiment, each assembly includes three magnets, optionally cylindrical, and the other elements coupled to the magnets for its actuation, positioning, protection, and other related functions. Such elements include three motors, three axles, housing, and/or positioning adjustment elements.

Figure 16B:
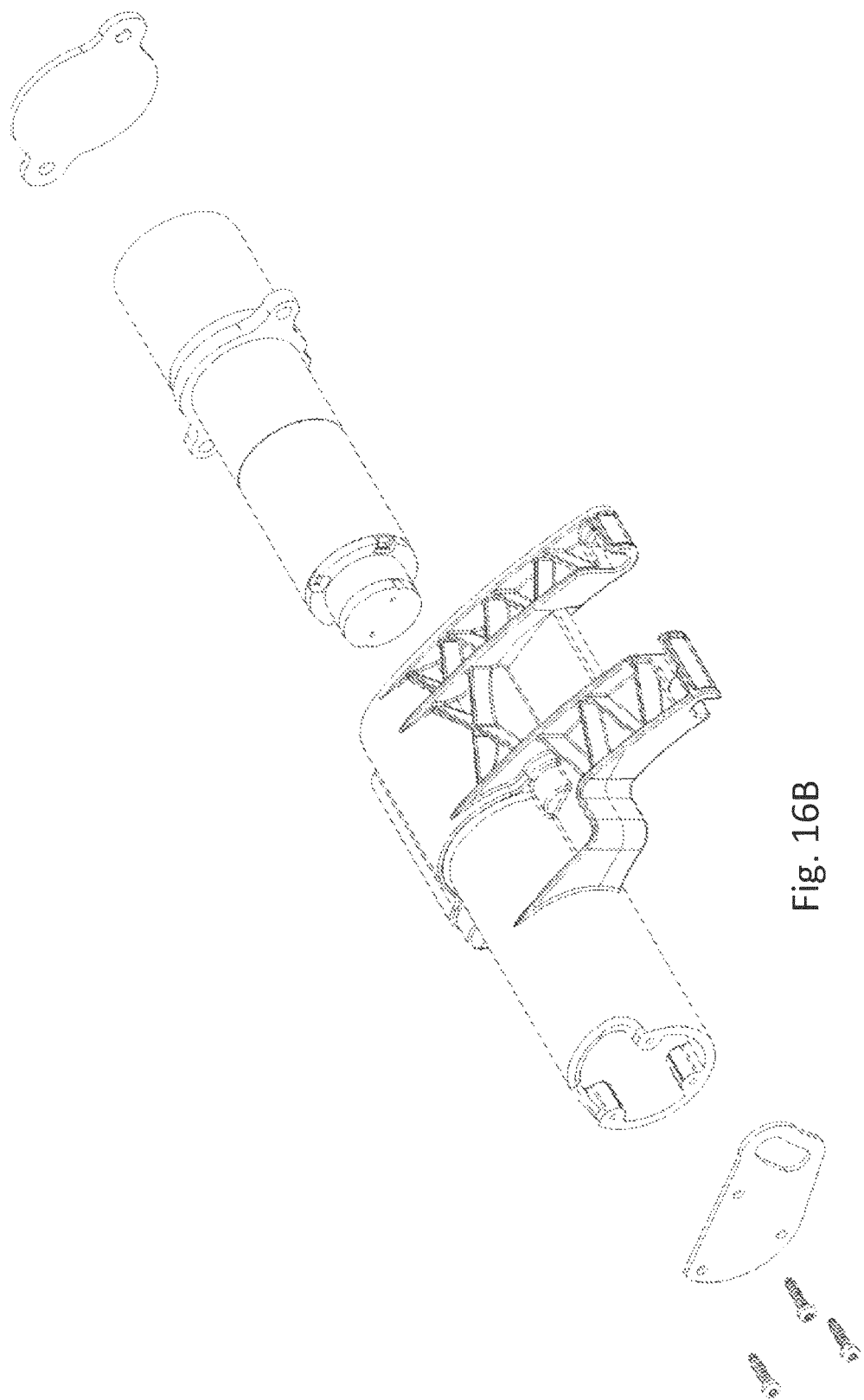

Referring to FIGS. 16A-B, in a particular embodiment, a magnet and its assembly as in the embodiment shown in FIGS. 13-14 are seen. This magnet assembly is optionally positioned at any of the three locations of magnet assemblies as shown in FIGS. 13-14. Each magnet assembly includes a protective housing of the assembly 1623a. In some embodiments, the protective housing remains fixed to the helmet and the scalp of the wearer during operation of the device. In some embodiments, the adjustment of magnet positions is via adjustment of the corresponding protective housing. In some embodiments, the protective housing includes a fixed or adjustable attachment to the housing 1201 of the helmet. In some embodiments, the protective housing includes a pivotable connection to a pivot pin 1422a, 1422b for adjusting positions of the upper and middle magnet assemblies 1321b-c relative to the position of the helmet and the scalp of the wearer. In some embodiments, the fixed connection between the protective housing and the helmet is loosened via an adjuster 1523. In some embodiments, the adjustable connection between the protective housing and the helmet is fastened via an adjuster 1523. In some embodiments, the protective housing includes a substantially hollow housing for enclosing a magnet, a motor, a gear box, and other elements therewithin. In further embodiments, the protective housing includes one or two covers 1623a_1, 1623a_2 as shown in FIG. 16 that fit to close to one or both ends of the hollow housing. In some embodiments, the one or two covers include a complementary interface, for example, a slit in 1623a_1 that interacts with the adjuster for fastening or loosening the attachment of the housing to the pivot pin. Alternatively, any other type of protective housing is used to service the similar purpose, for a non-limiting example, a clamshell housing.

In some embodiments, the protective cover includes a hard and non-flexible material. In some embodiments, the protective cover includes a material that minimizes interference to the magnet, motor, and/or gear box therewithin from elements of other magnet assemblies, housing of the helmet, and/or external sources. In some embodiments, the protective cover includes a material that helps reduce weight and/or cost of the protective cover without compromising its functions disclosed herein. In some embodiments, the pieces of the protective cover are removably attached to each other to enable easy dissembling or reassembly of the protective cover.

In some embodiments, the motor(s) and/or magnet(s) include a motor/magnet housing 110, 410, 510, and 610. The housing 110, 410, 510, 610 includes two structure pieces 410a, 410b supporting at least one motor, at least one magnet, or both. The two structural pieces 410a, 410b is parallel to each other. The two structure pieces have an elongate shape extending substantially in a two-dimensional plane defined by the "y" axis and the "z" axis of the subject. The housing supports a motor, a magnet, or both at one or both ends. The rotating axis of a motor, a gear, and/or a magnet is substantially orthogonal to one or both structure pieces of the housing. As a non-limiting example, the rotational axis of magnet 414a is the "x" axis and is orthogonal to the housing 410. In some embodiments, a magnet 414a-414c is attached indirectly to a housing 410 through a motor (right panel of FIG. 4). In some embodiments, a magnet 414a-414c is only attached to the housing 410 at one end. The one end is close to or at its south pole or its north pole (right panel of FIG. 4). The housing element 110, 410, 510, 610 is curved such that a lower edge of at least one of the two structure pieces 410a or 410b substantially fit to a portion of the scalp curvature of the wearer (left and middle panels in FIG. 4). The housing element 110, 410, 510, 610 has a lower edge that is curved to be part of an elliptical shape (400 of left panel in FIG. 4). Part of the elliptical shape 400 fits the scalp curvature substantially from the wearer's forehead to the top of the scalp. The housing element 110, 410, 510, 610 has a lower edge that is curved to be part of a circle, a concave line, a convex line, a straight line, or the like. The housing element 110, 410, 510, 610 has a lower edge that is curved to a predetermined shape and is not adjustable. Alternatively, the housing element 110, 410, 510, 610 has a lower edge that is deformable to fit to a specific portion of the scalp. The housing element 110, 410, 510, 610 is made of stiff or deformable materials. For the housing element, the materials only include non-ferromagnetic materials but do not include ferromagnetic materials. Alternatively, the materials only include ferromagnetic materials but do not include non-ferromagnetic materials. Alternatively, the materials include non-ferromagnetic materials, ferromagnetic materials, or both. As non-limiting examples, the materials include one or more selected from: plastic, aluminum, copper, polymer, wood, rubber, silver, gold, glass, steel and other ferromagnetic materials, or the like.

The distance between two supporting structures of the housing are about 2 inches (about 51.0 mm) to about 4 inches (about 102.0 mm). In some embodiments, the distance is in the range of about 2.8 inches (about 72.0 mm) to about 3.2 inches (about 82.0 mm). The magnet has a distance of about 0.75 inches (about 20.0 mm) to about 3.5 inches (about 89.0 mm) from its north pole to its south pole.

Each assembly, in this particular case, encloses a magnet 1614a, rotatably positioned in the protective housing. The magnets optionally rotate about a shaft or an axle connected thereon via a shaft adapter 1625a. The shaft adapter is sized to match the inner diameter of the magnet cross section to the cross section of the shaft. In some embodiments, the shaft or axle that each magnet is fixedly or rotatably attached to the protective housing thus allows rotational movement of each magnet thereabout.

In some instances, the assembly also includes a motor 1615a and a gear box 1624a for generating torque to actuate the magnet 1614a for rotation at a preselected frequency. In this particular embodiment, one or more of the motor, gearbox, magnet, shaft and shaft adapter are attached together for a compact configuration within the protective housing. In some embodiments, such attachment allows no or minimal displacement between two elements, no or minimal rotational or angular movement between two elements, or both.

In some embodiments, a helmet 10, 1200 includes at least one motor to at least three motors 115a-115c, 1615a. In some embodiments, the helmet includes a gear drive or a direct drive mechanism. In further embodiments, the at least one motor to at least three motors are suitable for operation with a gear drive mechanism, a direct drive mechanism, or both.

In some embodiments, the motor disclosed herein is a direct current (DC) motor. In further embodiments, the motor is a brushless DC motor, or a brushed DC motor, or in some embodiments a graphite or metallic brushed motor. In some embodiments, the operational voltage of the motor is about 12 Volts, about 24 volts, or any other voltages. In some embodiments, the operational current of the motor is about 0.5 Amps. In some embodiments, the operational current is the range of about 0.05 Amps to about 1.0 Amps.

In some embodiments, the current required depends on the motor voltage and the size of the magnets used. The numbers provided assume a voltage range of about 5V to about 48V.

In some embodiments, the helmet disclosed herein includes a gearbox 1624a, an encoder, or the like. The gear box includes a set of gears with its casing. The gear ratio is between about 2:1 to about 16:1. The gear box diameter is about 16 mm to about 24 mm. For instances, the gear ratio is entirely dependent on motor selection and the level of noise desired. In some embodiments, the gear box diameter is the same as or similar to the motor diameter. In some embodiments, the gear box dimeter is larger than the motor diameter. In some embodiments, the gear box diameter is no larger than the diameter of the magnet. In some embodiments, the gear box diameter is sufficiently large so that it prevents the magnet from being as close to the scalp as possible.

In some embodiments, the helmet includes at least one to at least three magnets 114a-114c. In further embodiments, the magnets are permanent or electromagnets. In further embodiments, the magnets are cylindrical magnets rotatable about an axis (for example, axis x in FIGS. 4-5) along its longitudinal direction and perpendicular to circular cross sections. In some embodiments, one motor drives the at least one magnet to at least three magnets. In further embodiments, each magnet is driven by at least one to at least three magnets. In some embodiments, each motor drives a different magnet separately.

In some embodiments, the magnets 114a-114c are arranged in an array along a concave surface that fits to a part of a subject's scalp curvature. In further embodiments, the magnets are arranged in a row along a curved surface from approximately a subject's forehead to about the top of the scalp. In certain instances, the concave surface is not necessarily the same as the curved surface of the top or bottom part of the helmet. Parts remain fixed while the magnet positions are customized to adjust fit to different subjects. In some embodiments, the magnet(s) are arranged so that the magnetic flux is substantially in the left-to-right direction along x axis, the anterior-to-posterior direction along y axis, or the head-to-foot direction of the subject along z axis. In some embodiments, the magnets 114a-114c are arranged in an array along a concave surface such that the north pole-to-south pole direction of each magnet in the array is substantially parallel to each other. The motors 115a-115c are arranged in an array along a substantially similar concave surface as the magnets 114a-114c. In some embodiments, the magnet/motor array pivot/rotate about a magnet assembly pivot 113. The array pivot is located close to an edge of the lower housing 107 and upper housing 106. The array pivot is located above the wearer's scalp with an adjustable height such that its distance to the scalp curvature is selected to suit the need in different procedures and/or for various subjects. Such distance is related to the array pivot support 108 which provide structural support for the pivot and attachment to the lower housing 107. The array pivot is located close to or at the rotational axis of a magnet 114a in the array. Alternatively, the array pivot is located near or at any other magnet or motor in the array. Using the array pivot, the location of the magnet/motor array relative to a portion of the wearer's scalp curvature is adjusted. The adjustment to each magnet occurs at the same time when the array pivot 113 is adjusted. However, individual adjustment of the location to each magnet in the array is or is not identical depending at the location of the array pivot 113 with respect to the location of each magnet. As a non-limiting example, when the array pivot is near the rotational axis of magnet 114a, the height of magnet 114b and 114c above a wearer's scalp is altered as the array pivot 113 is rotated, the height of magnet 114a is changed the least as compared to the other two magnets. The height change of magnet 114c is the largest as compared to those of the other two magnets 114b and 114a as the distance from magnet 114c to the rotation center, the pivot array pivot 113, is the longest among three magnets 114a-114c.

Figure 5:
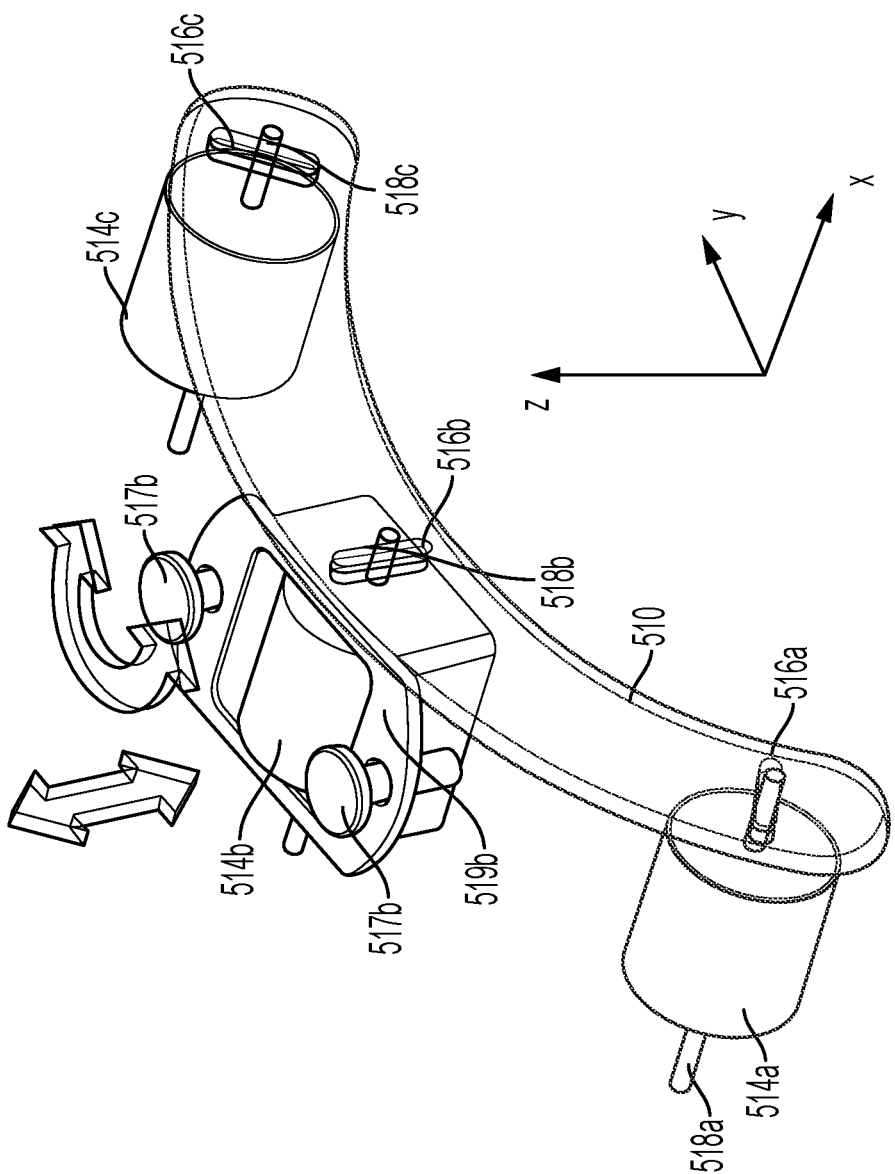
FIG. 5 shows an example of magnet height adjustment of a head mountable device, in accordance with embodiments.
Figure 17:
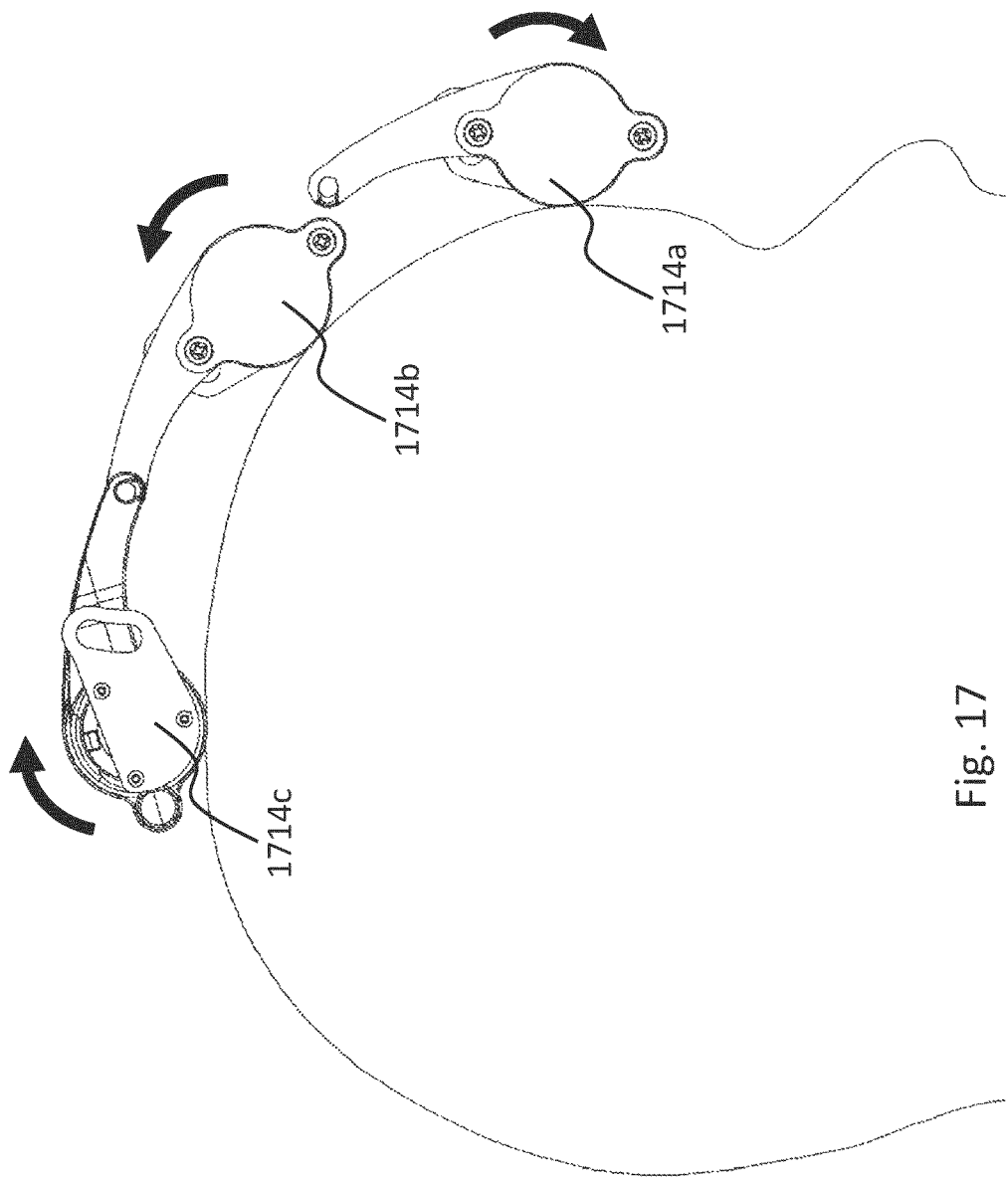
FIG. 17 shows an example of magnets of a head-mountable device as disclose herein, their positions when mounted to a patient and their rotational directions, in accordance with previously shown embodiments.

Referring to FIG. 17, the magnets 1714a-c and their corresponding assemblies are arranged along the curved surface from a subject's forehead to about the top of the scalp such that the rotational axes of the magnets are substantially parallel (for example, the rotational axis shown as parallel to axis x in FIGS. 4-5). In this particular embodiment, the middle magnet 1714b rotates in an opposite direction to the rotational direction of the top and bottom magnets 1714a, 1714c. In some embodiments, all three magnets are rotating about parallel rotational axes. In further embodiments, the rotational axis are substantially parallel to a region of the scalp surface. In some embodiments, the rotational axis is horizontal when the helmet is placed on a horizontal surface. In further embodiments, all three magnets rotate substantially about an axis that is parallel to the "x" axis, "y" axis, or any axis within the "x-y" plane as shown in FIGS. 4-5. In some embodiments, the rotational axis is parallel to or within the "x-y" plane.

Figure 13A:
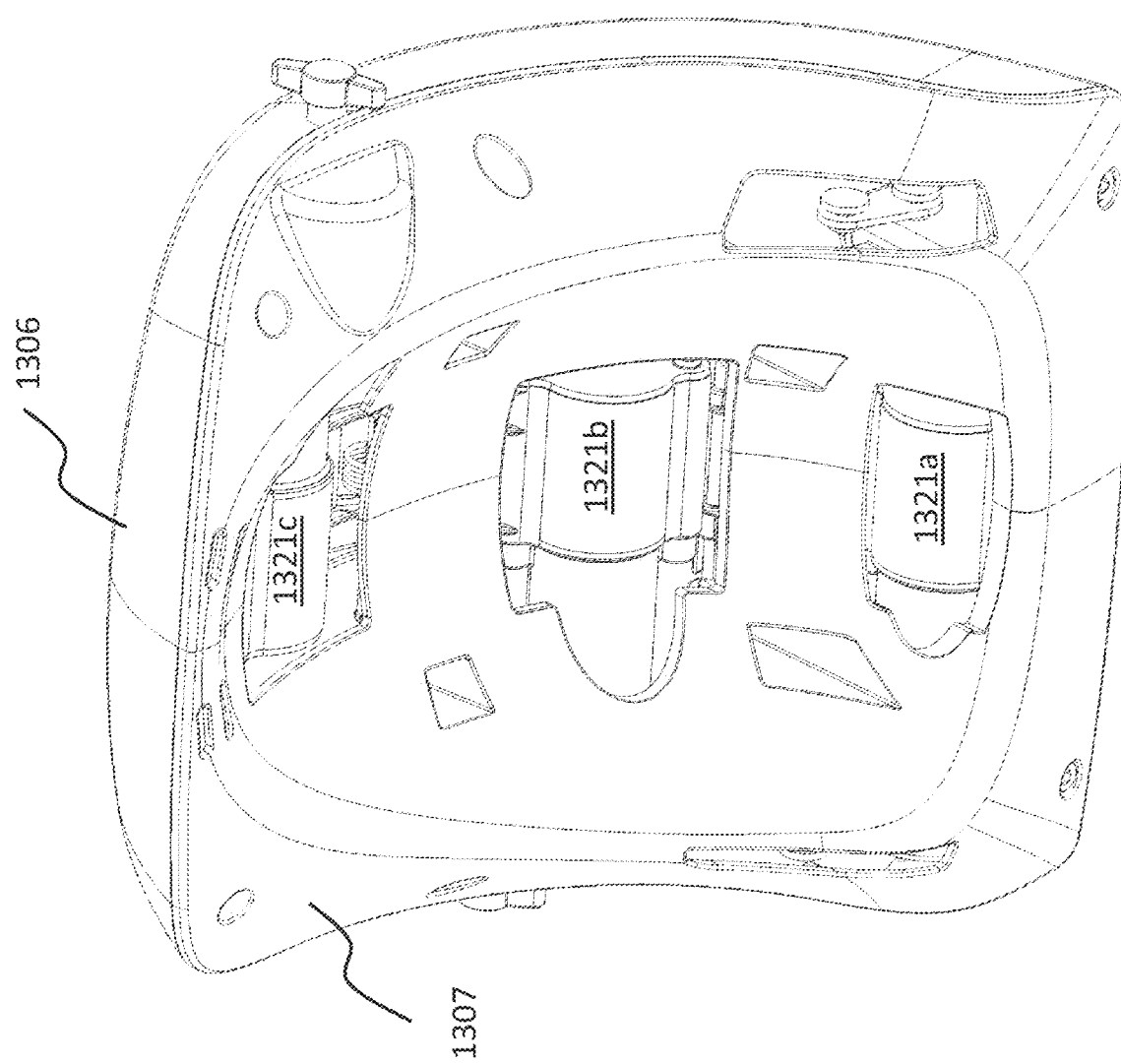
FIG. 13A shows a view from the bottom of the head-mountable device of FIG. 12.

In some embodiments, one or more of the magnets are completely enclosed within the helmet, thus the magnets do not extend beyond the concave surface of the lower housing 107, 1307. Alternatively, as seen in FIG. 13A, the concave surface includes openings that enable part of the magnets, motors, or other elements within the helmet to come through and extend beyond the concave surface. Such openings in the lower housing allows the magnets and other elements to move relative to the scalp of the wearer even when the helmet and the lower housing is fixed on the head of the wearer. As a result, fine tuning of position of each magnet is easy and convenient without moving the helmet housing.

In some embodiments, a deformable and flexible padding is placed in between the magnets and the head of the subject when part of the magnet(s) extends outside of the concave lower part of the helmet. In some embodiments, such padding increases comfort and reduces and minimizes physical contact of the magnets with the head of the subject. In some embodiments, such padding reduces undesired vibration due to movement of magnet(s). Advantages associated with the openings include more adjustability to the distance between one or more magnets and the desired application area of the subject. In some embodiments, such adjustment of the magnets within the helmet or beyond the concave surface are adjustable manually using the fit mechanisms. In some embodiments, such adjustment are automatically controlled by the controller having a digital processing device. In some embodiments, such adjustment use measurement of parameters of the magnet field as a position feedback. In some embodiments, such adjustment use any suitable measurements as a position feedback to the position adjustment. Such position feedback includes but is not limited to a drop gauge, a resistance sensor, a pressure sensor, an infrared sensor, a temperature sensor, or any combination thereof. The first fit mechanism may comprise a feedback receiver that receives a position feedback from a height measurement element, wherein the height measurement element is configured to measure a distance from the first permanent magnet to the head of the subject and wherein the position feedback comprises the distance measured or other information based on the distance measured.

The other information in the position feedback includes but is not limited to a distance data, a distance signal, a distance calculation, a distance measurement, a distance value, a value correlated with a distance, data based on the distance measured, a calculation based on the distance measured, or any combination thereof. Such adjustment of position of the magnets relative to the head occur before each therapy, during each therapy, or after each therapy. As a non-limiting example, the controller controls the adjuster and other elements of the fit mechanism to adjust height of the magnet closest to the top of the head of the subject at an increment of about 5.0 mm (moving toward the head) each adjustment after a position feedback from a drop gauge, when the drop gauge measures a distance of less than about 10.0 mm, decrease the increment from about 5.0 mm to about 1.0 mm and then to about 0.1 mm until the distance at the drop gauge equals about 5.5 mm.

In this embodiment, each magnet is separately coupled to a motor via a direct drive mechanism or gear drive mechanism. The drive mechanism includes a drive shaft. The movement of each magnet generates a magnetic field that is effective to a region of the head in close proximity to the magnet. In combination, a magnetic field combining the three magnet fields has a large effective region of the head, which includes areas in proximity to one, two, or all three of the three magnets. The effective area of the magnetic field is determined by parameters of the magnetic field. The motor is shielded to reduce interference to the magnetic field. In some embodiments, the helmet is positioned such that the bottom magnet is pressed against the subject's forehead. The bottom magnet is the closest to the forehead and eyebrow of the subject. In some embodiments, the helmet is positioned such that the top magnet is pressed against an area in close proximity to the top of the subject's head. In some embodiments, the middle magnet is placed between the other magnets.

The middle magnet is rotating in an opposite direction to one or both of the other two magnets. The advantages of having the middle magnet rotating in an opposite direction include one or more selected from the following: improved synchronization during operation of the three magnets; reduced heat emission; removal or elimination of undesired sound noise; improved energy efficiency for achieving similar operational frequency or speed; more stable generation of magnetic field; and less interference of motor operation by magnetic fields or currents; thus resulting in less expensive, more stable, less energy consuming, and more effective operation of the device.

Referring to FIGS. 3-6, the helmet 10 houses at least one, two, three, four, five, or six magnets 114a-114c, 414a-414c. The helmet houses at least one, two, three, four, five, or six motors 115a-115c and 415a-415c in addition to a certain number of magnets. Each motor is configured to actuate at least one, two, three, four, five, or six magnets 114a-114c, 414a-414c. Each magnet is actuated by at least one, two, three, or four motors. In some embodiments, the helmet houses at least three magnets and at least three motors. The magnets are permanent magnets. The magnets are electromagnets. The magnets are replaced by other elements that generate equivalent magnet field. These elements have similar size to the magnet(s) so that they are housed within the helmet.

Each magnet 114a-114c, 414a-414c is any suitable shape that is actuated to rotate. Any two magnets are or are not similar size or shape to each other. In some embodiments, each magnet has a substantially cylindrical shape. The north-pole to south-pole axis of a magnet is orthogonal to circular cross-sections of the cylindrical shape. The magnets are arranged in parallel and are separated by a predetermined distance. The magnets are arranged such that they will rotate about rotational axes that are substantially parallel to each other. The magnets are positioned such that the north pole-south pole axis is substantially aligned with the x axis of the wearer, which aligns with the left-to-right direction of the subject. The north pole-south pole axis has an angle to the x axis of the wearer. The north pole-south pole axis has an angle to the z axis of the wearer, which aligns with the head-to-foot direction of the subject. The north pole-south pole axis has an angle to the y axis, which aligns with the anterior-to-posterior direction of the wearer. The angle is about 1 degree to about 80 degrees. The north pole of one or more magnets faces the same direction of the wearer; the direction is left, right, anterior, posterior, head, foot, or an oblique direction in a three-dimensional space defined by the x, y, and z-axes of the subject.

The magnets 414a-414c are separated by a distance such that at least one motor is positioned between two otherwise adjacent magnets. The motor 415a is configured to actuate a magnet 414a to which it is adjacent. A motor is a gear drive or a direct drive. For a gear drive or a gear box, it includes a gear set 416a, 416b with at least two gears, at least three gears, at least four gears, or at least five gears. Alternatively, the motor includes a gear train of at least two, three, four, five, or six gears. The one or more gears of the same gear set have different diameters.

Alternatively, in some embodiments, a motor and gear box or a gear set driving a magnet is located laterally by a side of a magnet. Alternatively, the gears are enclosed within a gear box that is aligned laterally with the corresponding magnet as shown in FIGS. 13A-B. In some embodiments, the motor or gear box is located in different locations relative to the corresponding magnet that they actuate. For non-limiting examples, the motor and/or gear box is left or right to the north pole or south pole of a magnet that it actuates. A motor or gear box is located anterior to a magnet, a motor or gear set is located above a magnet, or posterior to a magnet. The motor or gear box position relative to a magnet varies depending on the pre-selected position of one or more magnets with respect to a scalp. In some embodiments, the position of a motor and/or gear box does not interfere with a predetermined fit of the magnet to the scalp curvature. As a non-limiting example, a motor or gear box is not positioned such that it is between magnet(s) and a portion of scalp of the subject. As seen in FIG. 4, one magnet 414a is positioned in close vicinity to or at the forehead and eyebrow of a subject. The north pole-south pole of the magnet is substantially parallel to the x-axis of the patient. In some embodiments, the magnets are positioned with different distances in between two adjacent magnets (are or are not separated by motor(s)). As seen in FIG. 4, magnets 414a-414c are aligned substantially to a quarter of a circumference of an elliptical shape 400.

The magnets are positioned such that the north pole-south pole axes of at least two magnets are not parallel. A line connecting the center of magnet 414a to the center of the elliptical shape 400 forms an angle "m" to the line connecting center of magnet 414c to the center of the elliptical shape. A line connecting the center of magnet 414a to the center of the elliptical shape forms another angle "n" to the line connecting center of magnet 414c to the center of the elliptical shape. The angle "m" is about 90 degrees, about 93.6 degrees, or in a range of about 75 degrees to about 105 degrees. The angle "n" is about 54 degrees, about 50 degrees, or in a range of about 40 degrees to about 70 degrees. The elliptical shape has a long axis of about 8 inches (about 204.0 mm). The elliptical shape has a short axis of about 5.5 inches (about 140.0 mm). The long axis or short axis of the elliptical shape is in a range of about 3 inches (about 77.0 mm) to about 12 inches (about 305.0 mm).

In some embodiments, the helmet as disclosed herein includes one or more fit mechanisms for adjusting the position/height of one or more magnets with respect to the head of the subject. In some embodiments, the helmet includes a plurality of fit mechanisms that each mechanism adjusts each of the at least three permanent magnets. In some embodiments, the helmet includes a plurality of fit mechanisms that each mechanism adjusts each of the at least one motor driving one or more magnets. In some embodiments, the fit mechanism is completely enclosed within the volume defined by the upper and lower parts of the helmet (FIG. 3) in a closed configuration. In further embodiments, part of the fit mechanism is physically accessible to a user or a subject from outside of the helmet. In some embodiments, the fit mechanism is only physically accessible to a user or a subject from outside of the helmet. In some embodiments, the fit mechanism is remotely accessible to a user or a subject from outside of the helmet via remote control in a closed configuration.

Figure 6:
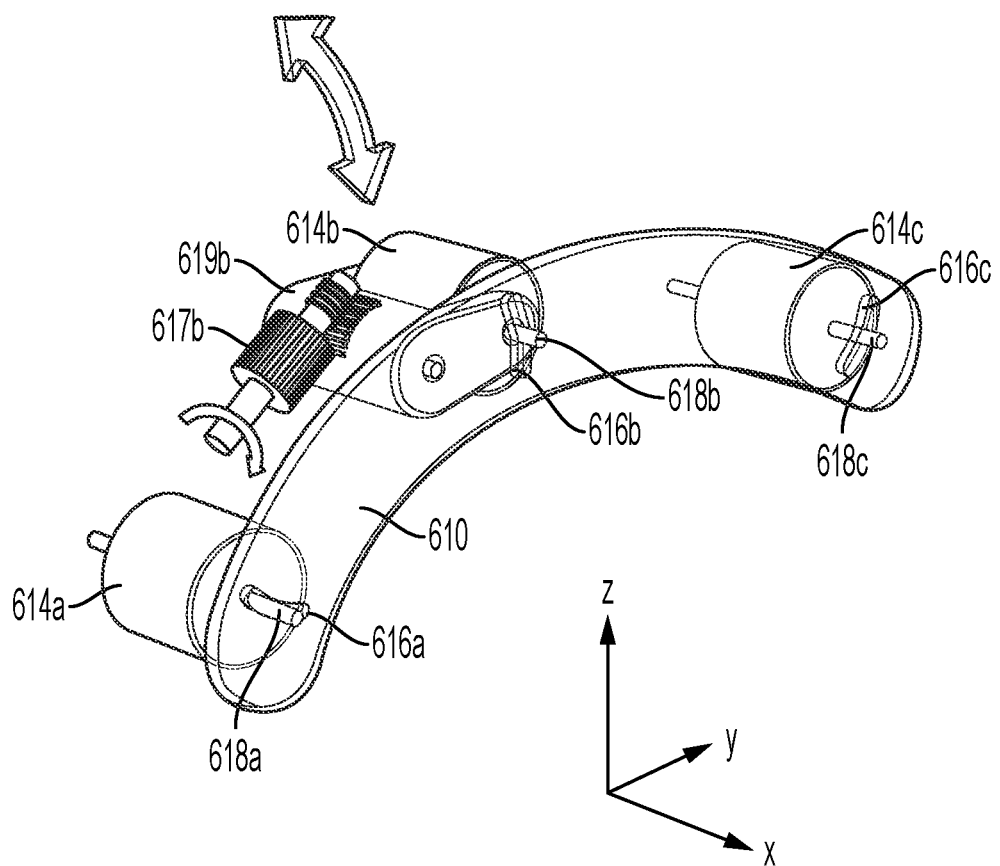
FIG. 6 shows another example of magnet height adjustment of a head mountable device, in accordance with embodiments.

Referring to FIGS. 5-6, in some embodiments, the position/height of one or more magnets 514a-514c is adjusted manually or automatically via a fit mechanism. In some embodiments, the fit mechanism adjusts magnet positions when the helmet is fastened and fixed relative to the head of the subject. In further embodiments, the fit mechanism adjusts magnet height/position to the scalp when the upper part and lower part of the helmet is fastened relative to the head. In some embodiments, each magnet is adjusted independently. The height of each magnet is adjusted independently using a fit mechanism. In some embodiments, independent adjustment using fit mechanism(s) is convenient and efficient in adjusting individual distance from each magnet to the specific area of the head of the subject, thus allows optimal flexibility in magnet placement and dynamic fitting of the helmet to various subjects. Further, such individual adjustment in some embodiments provides additional flexibility to a non-flexibly concave surface of the helmet and provides more customized fitting to different head shapes, sizes, and medical needs of patients.

In some embodiments, the fit mechanism is a local radial translational adjustment (FIG. 5) or a local pivot adjustment (FIG. 6) without affecting the height of other magnets. One or more magnet(s) 514a-514c, 614a-614c of a helmet includes a rotational shaft (interchangeable and equivalent to a rotational axle as disclosed herein) 518a-518c, 618a-618c. In some embodiments, the rotational shafts 514a-514c, 614a-614c are or are not parallel to each other. In some embodiments, the shortest distance from the rotational shafts 514a-514c, 614a-614c to the scalp are or are not similar. In some embodiments, the rotational shaft(s) is located to achieve a shortest possible distance from the shaft(s) to the scalp curvature. The rotational shafts 514a-514c, 614a-614c are movably received in a slit 516a-516c, 616a-616c. In some embodiments, the slit enables translational movement of the rotational shafts in order to adjust height of the magnets above a scalp of a wearer. In some embodiments, the helmet also includes a drop gauge to measure height of magnet(s) above scalp. In some embodiments, the helmet also includes an element that provides physical or digital feedback, re: the magnet height. Such feedback is indicated by a visual indicator, a digital signal at the controller, an audio indicator, or the like. Alternatively, two or more magnets are adjusted dependently. As a non-limiting example, a local radial translational adjustment (FIG. 5) or local pivot adjustment (FIG. 6) is used to adjust the height of at least two magnets at the same time.

In some embodiments, the fit mechanism includes an adjuster 517b. The rotational shaft (equivalently to the axle herein) 518b of magnet 514b is moved along the slit 516b via adjustment of one or both knobs 517b. One or both of the knobs 517b are turned clockwise or counter-clockwise when viewing from the top. The screw thread (not shown) of knob(s) secures element 519b to the magnet(s) and motor(s) housing element 510 at a selected position along the slit 516b. Thus, the magnet 514b is indirectly secured to the housing at the selected position of the slit 516b. Alternatively, the rotational shaft 618b is moved along the slit 616b via adjustment of at least one worm gear comprising a worm 617b and a gear 619b. Rotation of the worm adjuster 617b results in rotation of the gear 619b and thus causes the rotational shaft 618b attached thereto to move along the slit 616b and changes the height of the magnet 614b relative to the scalp of the subject. The slit 516a-c, 616a-c extends in a direction that is substantially orthogonal to the side edge of the housing element 510, 610. In some embodiments, the slit is a substantially straight slit or a curved slit. In some embodiments, the slit is of arbitrary shape that is suitable to fit the rotational shaft 518a-c, 618a-c therethrough and enables magnet height change when the rotational shaft moves along the slit. In some embodiments, the slit is of arbitrary shape that enables magnet height change from about 0.01 inches (about 0.3 mm) to about 1.0 inches (about 26.0 mm).

In some embodiments, the magnet that is closest to the forehead/eyebrow of the patient is not adjustable via a fit mechanism. In further embodiments, the magnet that is closest to the forehead/eyebrow of the patient has a fixed distance to the head of the subject when the helmet is fastened on the subject.

Figure 15:
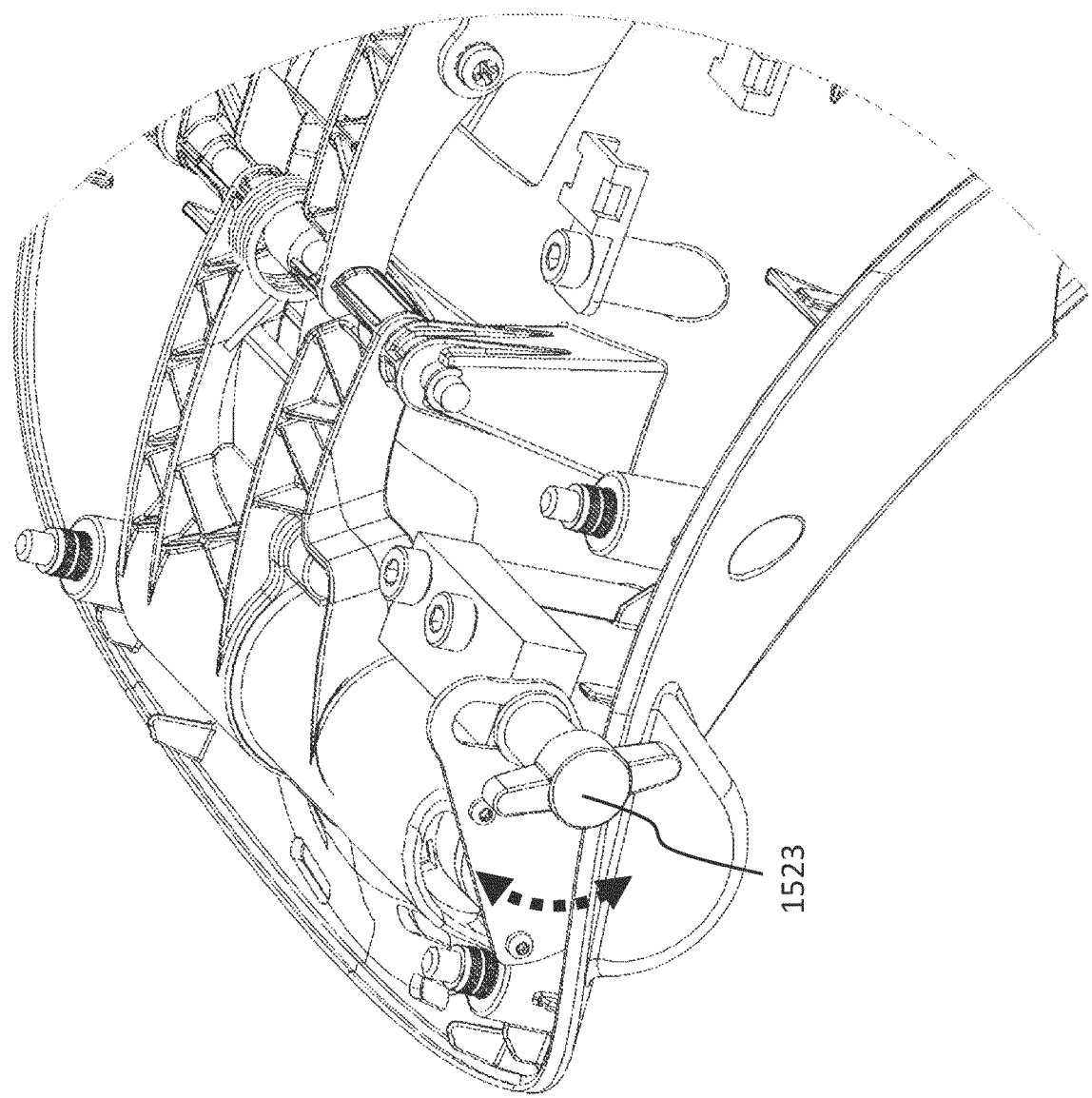
FIG. 15 shows an exemplary embodiment of an adjuster for adjusting position of one or more magnet(s) within the head-mountable device.

Referring to FIGS. 14-15, in a particular embodiment, position of one or more magnets are adjusted via one or more adjuster 1523. Preferably, the adjuster is positioned outside of the helmet housing parts or conveniently accessible from outside of the helmet by a user. In this case, the magnet positions are optionally adjusted by loosening thumbscrew 1523, each thumbscrew for loosening the attachment of one or both of the top two magnets to the housing. After loosening, the top two magnets are fitted to the correct position optionally via rotation about the pivot pin 1422a-1422b, ensuring that the magnets are pressing on the scalp, and then re-tightening the thumbscrew. Optionally, the two adjustable magnets are slightly spring loaded to aid with the adjustment as shown in FIG. 14. In this embodiment, the spring pushes the magnet housings towards the patient to move the magnets as close as possible to the patient's head. The spring 1427c is optionally a torsional coil spring, a helical compression spring, an extension spring, a leaf spring, a resilient rubber or foam pad, or any other spring type. Referring to FIG. 14, in a particular instance, both the top and middle magnets are pivotably attached to the same pin 1422b while the bottom magnet is pivotably attached to a different pin 1422a.

In some embodiments, the connection or attachment to the pivotable pin includes a latch, a hook, a loop, a screw, or other possible elements.

Referring to FIG. 18A, in a particular embodiment, positions of the top 1814c and middle 1814b magnets are adjusted in order to fit to a patient's head that is larger than the helmet in the portion corresponding to the helmet. In this embodiment, the bottom magnet closest to the forehead of the patient remains fixed relative to the scalp and housing of the helmet, while the other two magnets are moved relative to the scalp and housing. More specifically, by loosening adjuster screws, both the top and middle magnets are pivotable about the pivot pin 1822b to which they are connected. In this case, the pivoting motion results in a displacement of the center of the magnet (at the rotating shaft) away from the scalp. The line between the magnet center and the center of a virtual elliptical shape 400, approximating the head of the wearer, forms an acute angle to the minor axis of the ellipse. Such angle changes slightly when the magnet center is moved away from the scalp to fit a larger head. Similarly, the middle magnet when moved is not moving along a line connecting the center of the ellipse 400 and the magnet center at its previous position before movement.

Before fit adjustment of the magnets, a line connecting the center of magnet 1814b to the center of the elliptical shape 400 forms an acute angle "m" to the line connecting the center of magnet 1814c to the center of the elliptical shape. A line connecting the center of magnet 1814b to the center of the elliptical shape forms another angle "n" to the line connecting the center of magnet 1814c to the center of the elliptical shape. The angle "m" is about 90 degrees, about 93.6 degrees, about 94.9 degrees, or in a range of about 75 degrees to about 105 degrees. The angle "n" is about 54 degrees, about 53.2 degrees, or in a range of about 40 degrees to about 70 degrees. The elliptical shape has a long axis of about 8 inches (about 204.0 mm). The elliptical shape has a short axis of about 5.5 inches (about 140.0 mm). The long axis or short axis of the elliptical shape is in a range of about 3 inches (about 77.0 mm) to about 12 inches (about 305.0 mm). After fit adjustment of the magnets, angle "m" or "n" increases or decreases, depending on the displacement. In some embodiments, the ellipse dimensions and angles herein are an approximation of head dimensions. Due to the adjustability in the system, there is a range of ellipses that would contact the magnet housings with a wide range of dimensions. Such adjustability in the system ensures that in some embodiments, one magnet touches the forehead, one magnet touches approximately the top of the head, and the middle magnet is approximately in the middle.

Referring to FIG. 18B, in a particular embodiment, positions of the top 1814c and middle 1814b magnets are adjusted in order to fit to a patient's head that is smaller than the helmet in the portion corresponding to the helmet.

Referring to FIG. 18C, in a particular embodiment, range of adjustment positions of the top 1814c and middle 1814b magnets are optionally about 0.5 inches (about 13.0 mm). In this embodiment, the ellipse for nominal adjustment would contact all three magnet housings when the magnets are located at the middle of their range of adjustment. In some embodiments, the nominal ellipse is an approximation of the average-side head of a subject.

In some embodiments, a motor, a gear box, or other element within a magnet assembly is made of materials that only include non-ferromagnetic materials but do not include ferromagnetic materials. Alternatively, the materials only include ferromagnetic materials but do not include non-ferromagnetic materials. Alternatively, the materials include non-ferromagnetic materials, ferromagnetic materials, or both. As non-limiting examples, the materials include one or more selected from: plastic, aluminum, steel, copper, polymer, wood, rubber, silver, gold, glass, or the like. Alternatively, a motor, a gear box, or other element within a magnet assembly are shielded by non-ferromagnetic materials such that it has no or minimal interference or influence to the magnets and the magnetic field generated by the magnets.

While permanent magnets of any strength are utilized for the methods and devices described herein, generally magnets having strengths within the range of about 10 Gauss to about 3 Tesla (30,000 Gauss) are used. In some embodiments, the strength of at least one permanent magnet is from about 100 Gauss to about 2 Tesla (20,000 Gauss). In some embodiments, the strength of at least one permanent magnet is from about 300 Gauss to about 1 Tesla (10,000 Gauss). In some embodiments, the strength of at least one permanent magnet is from about 100 Gauss to about 0.5 Tesla (5,000 Gauss).

In some embodiments, the permanent magnets for the methods and devices described comprise rare earth magnets such as neodymium, iron, boron or samarium cobalt magnets. In some embodiments, the permanent magnets for the methods and devices described are neodymium iron boron magnets. In some embodiments, ceramic magnets, electromagnets or other more powerful magnets are utilized as they become available. In some embodiments, electromagnets are utilized for the methods and devices described. Current is supplied to the electromagnet by wires penetrating through the devices described and connecting to an external power source.

In some embodiments, the magnets as disclosed herein move relative to the upper part, lower part of the helmet, or the head of the subject when the helmet is fastened on the subject. In some embodiments, the movement of the magnet includes translational movement, rotational movement, swing movement, or any other suitable movement in order to position the magnet to a pre-determined position or to deliver a predetermined magnetic field to the subject. In some embodiments, the magnet rotates via an axle along a first axis of rotation. The axle drives movement of the magnet when actuated by a motor coupled to the axle. In some embodiments, the axes of rotation of all magnets are substantially parallel to each other. As a non-limiting example, all three magnets 414a, 414c, 414b rotate about axes that are substantially parallel to "x" axis in FIG. 4. In some embodiments, all the magnets rotate at substantially a same frequency. In some embodiments, all the magnets rotate at substantially a same frequency at specific points of a movement cycle. In further embodiments, all the magnets rotate in a manner such that the north-poles of the magnets are aligned during rotational movements. As a non-limiting example, the north pole-south pole axes of magnets 414a, 414b, 414c are orthogonal to the scalp at substantially the same time with north-poles pointing to the scalp while south poles are pointing away from the scalp. At a later time, the north pole-south pole axes of the magnets are orthogonal to the scalp again at substantially the same time with north-poles pointing away from the scalp. In some embodiments, all the magnets rotate in a manner such that the north pole of one magnet is aligned with the south-poles of the other magnets. In some embodiments, the term "aligned" means that the north pole-south pole axes of two or more magnets are pointed in substantially the same direction. In some embodiments, all the magnets of the magnet assembly rotate in the same rotational direction, either clockwise or counter-clockwise when viewed from the left side of the patient. In some embodiments, one magnet rotates in a direction that is opposite to the rotational direction of the other magnets. In further embodiments, the magnet rotating in the opposite direction from other magnets is the middle magnet 114b, 414b, 514b, 614b, 1714b. In further embodiments, the magnet rotating in the opposite direction from other magnets is the magnet, 114a, 414a, 514a, 614a, 1714a, closest to the forehead/eyebrow of the subject or the magnet closest to the top of the head, 114c, 414c, 514c, 614c, 1714c. As a non-limiting example, 414a and 414c, 1714a and 1714c rotates in the same direction while 414b, 1714b rotates in an opposite direction from that of the other two magnets at the same frequency. In this case, the north pole-south pole axes of all magnets rotate to be orthogonal to the scalp at substantially the same time with north-poles pointing to the scalp. At a later time, the north pole-south pole axes of the magnets rotate to be orthogonal to the scalp again at substantially the same time with north-poles pointing away from the scalp.

In some embodiments, the helmet as disclosed herein includes at least three magnets (FIGS. 3-6). In some embodiments, one magnet 114a, 414a, 514a, 614a, is closest to the forehead/eyebrow of the subject, one is closest to the top of the head 114c, 414c, 514c, 614c, and the other magnet 114b, 414b, 514b, 614b is in between the two magnets.

In some embodiments, all the magnets rotate synchronously such that each magnet is approximately at the same point of a movement cycle at the same time point.

In some embodiments, the north pole-to-south pole direction of one or more permanent magnets are parallel. In some embodiments, the north poles of two or more magnets move in a synchronized way in movement of the magnets such that the north poles of two or more magnets move to positions closest to the scalp of the subject approximately at the same time while the south poles of two or more magnets move to positions furthest to the scalp of the subject substantially at the same time. In other words, each magnet moves such that the different poles of each magnet approach the scalp in alternative manners at approximately the same points.

For instance, movements of one or more magnets are at, or close to, a frequency within a specific EEG band, for example, delta band (about 1-about 4 Hz), theta band (about 4-about 8 Hz), alpha band (about 8-about 13 Hz), and beta band (about 13-about 30 Hz). In some embodiments, the movement of magnet(s) include one or more frequencies from within one or more EEG bands. Alternatively, movement of the magnet(s) is at one or more frequencies within a range from about 1 Hz to about 100 Hz.

Figure 8:
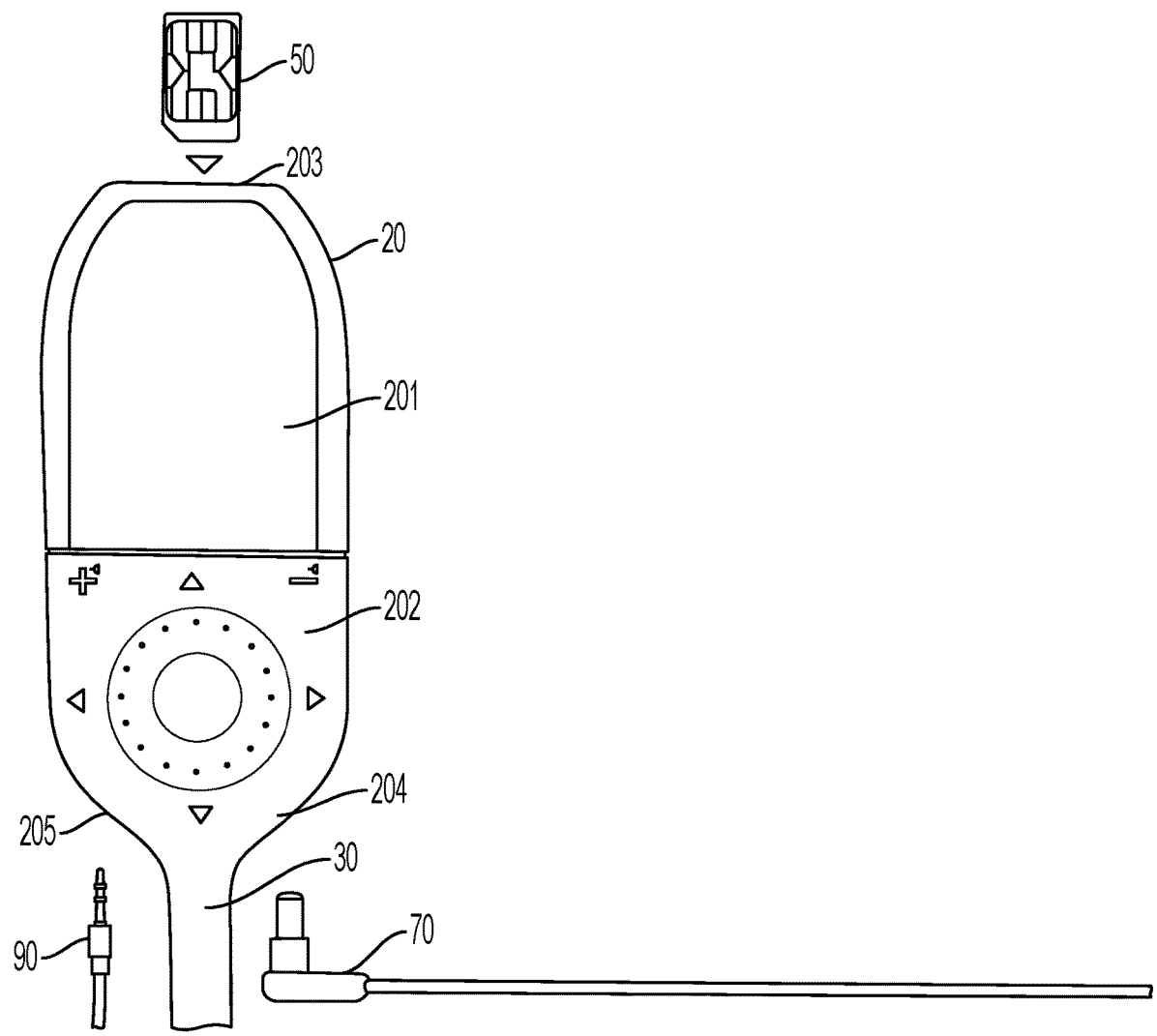
FIG. 8 shows the controller of the head-mountable device of FIG. 1, in accordance with embodiments.

In some embodiments, the devices and methods disclosed herein include a controller. Referring to FIGS. 7-8, in some embodiments, the controller 20 includes one or more selected from: an electronic display 201; an input interface; a button array 202; a connection 204 to receive a power source 70; a unit 203 to receive or read and write to computer readable media 50; a connection to receive or process EEG data 50; a unit 205 to connect to headphone(s) 90; a cable 30; a non-transitory computer memory unit; a rechargeable battery; an interface to electronically or mechanically connect to a helmet.

In some embodiments, the controller 20 includes one or more elements selected from: a digital processor; a logic; a digital signal processing unit; and non-transitory computer readable media. In some embodiments, the above-mentioned element(s) of the controller controls one or more selected from: the motor(s); the magnet(s); and the gear box. In some embodiments, the controller controls one or more selected from: duration of movement; repetition pattern of movement; track or trajectory of movement; frequency of movement; time for onset/stop of movement; acceleration of movement; speed of movement; direction of movement in two or three dimensions; type of motion; rotation axis of movement in two or three dimensions; distance of movement in two or three directions; distance of magnets to each other or to a determined portion of the head; and distance of magnets to one or more motors. In further cases, the control of magnets or motors results in the control of the magnetic field(s) generated thereby. In yet some embodiments, the controller controls the frequency of the magnetic field(s); the phase of the of the magnetic field(s); the amplitude of the magnetic field(s); the waveform of the frequency; the amplitude or the phase of the magnetic field; the duration of the magnetic field(s); the direction of the magnetic field(s); the polarity of the magnetic field(s); the properties of the magnetic flux; spatial distribution of the magnetic field; or a combination thereof.

The controller controls various aspects of the wearable device 10 and its elements. Such control requires certain user input(s) at the input interface, such as a treatment plan number or a target frequency. For example, a user manually inputs a target intrinsic frequency at the input interface, and the controller controls the movement of magnet fields at the input target frequency. As another example, a user inputs an application protocol number, and the controller controls the magnets to carry out the exact protocol including frequency, Q-factor, duration, or other parameters of the device. Alternatively, such control is automatic such that it requires minimal user input including power on, power off, starting a treatment, stopping a treatment, or the like. As an example, a user enters an intrinsic frequency of the subject, and the controller calculates a target frequency, a treatment plan based on the intrinsic frequency of the patient. As an example, a user uploads EEG data and starts treatment, and the controller calculates information from the EEG data, compares it to information from a healthy subject, and carries out a treatment plan based on that comparison. The controller is used to turn on or turn off the wearable device 10. The controller is used to display if the device is properly mounted to a subject, especially if each magnet has a height that is within a pre-specified range of heights. The controller is used to control magnet height such that each magnet has a pre-selected height above the scalp of the subject. The controller is used for receiving a frequency of movement, number of repetitions for each procedure, and/or duration of procedure from a user. The controller is used to automatically adjust a frequency of movement, number of repetitions for each procedure and/or duration of procedure. Further, such manual or automatic adjustment is based on the EEG data received and/or processed at the controller. The controller is used to select a pre-programmed procedure(s) of the device. Such selection is manual from a user at the input interface, or automatic. Alternatively, such manual or automatic selection is automatic based on the EEG data of the subject. The digital display is used to display status information of the device. As an example, a magnet height measured by a drop gauge is shown to a user at the display. The magnet height then is adjusted manually or automatically using the array pivot 113 and/or local adjustments 517b or 617b based on the measured height of the magnet(s). As another example, the digital display is used to display EEG data of a user before, during, or after a procedure. The digital display then displays the progress of a procedure.

The input interface enables user input to be received by the controller and thus controls various parameters of the helmet as disclosed herein.

In some embodiments, the above mentioned element(s) of the controller automatically receives one or more selected inputs from the feedback signal from the magnet(s), the feedback signal from the motor(s), and the feedback signal from the gear box(es). In some embodiments, the feedback signal includes one or more of the following: rotational speed, current, voltage, temperature, phase, frequency, position relative to a stationary element, position relative to one or more other movable element, and an error message. In some embodiments, the control of one or more elements disclosed herein is based on the automatic feedback signal(s). In further embodiments, the control includes a digital processor and a computer executable program to derive control command(s) based on at least an input from a user, an automatic feedback from the device, and/or internal program stored in the device.

The controller is a hand held unit or any other suitable unit that is portable. The controller includes one or more selected from: a digital processing device, non-transitory computer readable/writeable storage medium, a software module, a processor, a computer program, or any suitable software or hardware.

The device as disclosed herein includes a treatment plan, an application protocol, or use of the same. In some embodiments, the treatment plan or application protocol is generated at the device based on one or more parameters selected from: a subject's physical condition, a subject's EEG data, a subject's intrinsic frequency within a specified EEG band, a subject's Q-factor of an intrinsic frequency within a specified EEG band, a treatment record, a medical professional's instructions, or the like. In some embodiments, the treatment plan or application protocol is generated by the device based on inputs at the user input interface. In some embodiments, a treatment plan or an application protocol is received at the device from an external source. In some embodiments, a treatment plan or an application protocol is loaded into the device. In some embodiments, the user starts, pauses, stops, or modifies an existing plan or protocol using the controller.

In some embodiments, the devices and methods disclosed herein include a headband 102. In some embodiments, the headband is adjustable in order to provide a comfortable fit to a subject's head. In further embodiments, the headband includes an adjustment knob for adjusting the tightness of fit of the headband to a subject. In further embodiments, the adjustment knob is rotatable in order to adjust the circumference of the headband. In some embodiments, headband is removable to allow the headband and the elements attached thereto to be worn on or removed from the head of the subject.

In some embodiments, the devices and methods disclosed herein include computer readable media or a SIM card 50.

In some embodiments, the devices and methods disclosed herein include a processor 60 for processing EEG data. In further embodiments, the processor is for EEG data manipulation which includes but not limited to data compression, decompression, de-noise, frequency analysis, filtering, Fourier Transformation, data truncation, data sampling, data storage, calculation of intrinsic frequency within a specified EEG band, calculate Q-factor of an intrinsic frequency within a specified EEG band, or a combination thereof. In some embodiments, the processor is connected directly or indirectly to EEG lead(s) of a subject.

In some embodiments, the devices and methods disclosed herein include one or more EEG leads 91.

In some embodiments, the devices and methods disclosed herein include an AC adaptor 70.

In some embodiments, the devices and methods disclosed herein include a lay-flat cable 30. In some embodiments, the lay-flat cable is electronically or electrically connected to the motor(s), the magnet(s), or the motor(s) and the magnets so that the motor(s), the magnet(s), or both are controlled by the controller. In some embodiments, the control is automatically determined by the controller, or manually by a user. In some embodiments, the flat cable is electronically or electrically connected to the motor(s), the magnet(s), or the motor(s) and the magnets via an interface 105. In further embodiments, the interface 105 is located within the headband or underneath a headband wrap. In some embodiments, the interface is a USB connection interface, a phone line interface, an Internet cable interface, a WIFI connection interface, a Bluetooth connection interface, an e-SIM card interface, a virtual SIM card, a smart card interface, a SIM card interface, a USIM card interface, or the like.

Figure 9:
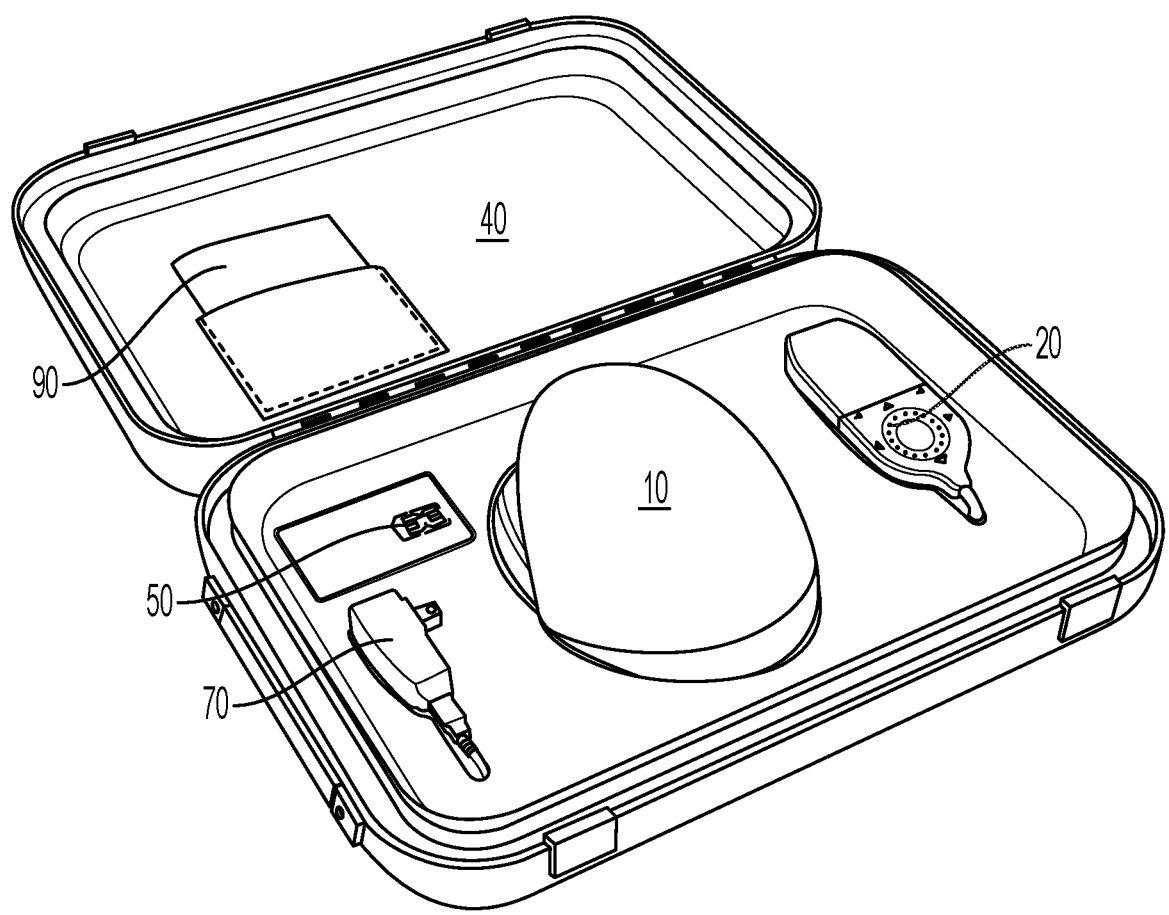
FIG. 9 shows the protective cover for enclosing the head-mountable device, in accordance with embodiments.

In some embodiments, the devices and methods disclosed herein includes a storage element 40 to store at least one tangible element of the devices as disclosed herein. In further embodiments, the storage element acts as a home base for use of the device in-home, allows convenient transportation for use on-the-go, protects device from external impact and possible damage. In some embodiments, the storage element is compact and/or dedicated to sustain the life of the devices. In some embodiments, the storage is used to store more than one element of the devices such that it allows usage of the device at home or on the go. In some embodiments, the storage has one or more compartments, each for holding one or more elements of the device for safety in transportation. In some embodiments, the storage 40 is used to hold one or more selected from: a helmet and its enclosing element 10, a power plug 70, a controller 20, a non-transitory computer-readable media 50, a headband wrap, a head pad, an EEG lead 91, a digital computing device, and instructions 90. In some embodiments, the devices and methods disclosed herein include a protective case 40. In some embodiments, the protective case has a size or weight that is suitable for portability of the case and elements enclosed therewithin. Referring to FIGS. 7, and 9, in some embodiments, the protective case houses all the tangible elements of the devices as disclosed herein.

In some embodiments, testing is performed to evaluate different motors for suitability in the device disclosed herein. Several different motor types are tested. In some embodiments, the magnets are driven directly by the motors without the use of an external drivetrain.

As a non-limiting example, in some embodiments, the DCX 22 S series of motors are selected (Maxon Motor AG). These motors are smaller in diameter than the magnets, have torque and power ratings exceeding the Faulhaber motors (used in other non-limiting examples), are shorter than certain motor/gearbox combinations, and are available in relatively short time frames. Initially, a 12V DC brushed motor with precious metal brushes, a 6.6:1 ratio gearbox, and a 1 impulse per turn encoder is selected for testing. After testing, it is understood that these motors do not allow for adequate speed control. These motors were also put on durability testing. The test was run by connecting the motors to a bench power supply. The motors were mounted in a prototype headset and a DC voltage was applied to achieve a 10 Hz output speed. After 172 hours of run time, one of the motors ceased to function. Upon inspection by Maxon Motor AG, it was determined that the brushes were completely burned away. This was a premature failure.

In some embodiments, 24V DC motors with precious metal brushes, a 1024 impulse encoder and a 5.3:1 gearbox were built into prototype headset for Electromagnetic Interference (EMI) testing. During EMI testing, the level of electromagnetic emissions increased over time. For the first several minutes, the emissions were fairly low, but then gradually increased to a very high level. When the motors were turned off, then turned back on, they had much lower emissions for several minutes then gradually increased. A correlation was shown that when large current spikes above or below the typical variation occurred, the motor electromagnetic emissions increased correspondingly. The magnets were replaced with metal slugs of similar weight. As a result, the motor current remained steady and did not exhibit "spikey" behavior. An individual motor with a magnet was run at a large distance from other magnets, and after a few minutes, it exhibited the "spikey" motor current behavior. This lead to the conclusion that the behavior in these motors was due to the magnetic fields.

In some embodiments, testing was run with a brushless DC (BLDC) motor with similar specifications to brushed DC motors tested herein, but without a gearbox or encoder. This motor drives the magnets at higher speeds than the brushed motors. By decreasing the motor speed to that of the brushed motor, magnet is driven to run at lower speeds. Adding a gearbox will help with achieving this speed difference in motor(s) and magnet(s) when using BLDC motors. In some embodiments, two different types of motors were test: BLDC motors (e.g.: Maxon EC Max 22 with a 4.4:1 gearbox), and Brushed DC motors with graphite brushes and a 5.3:1 gearbox. During durability testing, the BLDC motors periodically slowed down or sped up for 1-2 seconds, then immediately returned to the expected speed. Initially, this behavior occurred fairly regularly, e.g.: every 5-6 minutes. In some instances, attempts to adjust the tuning of the controllers had some effect, but only reduced the frequency of the undesired speed change. Isolating the encoder signals to a separately shielded cable also had no tangible effect. The brushed DC motors also exhibited momentary speed changes at fairly longer intervals. Typically, it took about 1.5-2.0 hours for the uncommanded speed changes (USC) to start occurring, then they would occur approximately every 15-30 minutes thereafter.

In an attempt to isolate the cause of the above failures, a series of tests were performed. In some embodiments, the original power supply was removed from the circuit of the device and a lab power supplies was used instead. The original power supply had a minimum expected load of 0.5 A and that caused unusual behavior. The change of power supply did not change the speed change behavior. Additional testing indicated that the motor controller temperature was a factor in the problem. In a separate test, the outside of the motors were heated to determine that motor temperature was not a noticeable factor causing the USC.

In some embodiments, to confirm the motor controller temperature dependency on USC, a test was run with the main enclosure open, but with the motor controller EMI shield in place. This allowed ambient air to better contact with the EMI enclosure and keep the motor controllers cooler. The main power supply was turned on to generate heat, but not used to power anything. After 1 hour and 50 minutes, a motor speed change occurred. The system was allowed to run for about 5 hours and 45 minutes. Speed changes were observed at random intervals of between 6 and 34 minutes. In some embodiments, this test indicated that the threshold was 39° C. or lower.

Afterwards, a large fan, (e.g., Sunon PMD1212PMB1-A), running at full speed was used to blow air over the open controller system, with EMI shields still in place. The temperature inside the motor controller EMI shield dropped quickly. One more speed change was observed, 7 minutes after applying the fan, but then the USC stopped. This indicated that the system was below the temperature threshold that caused USC. A lower temperature threshold of 33° C. was found by gradually reducing the fan speed.

To check whether the motor controllers were damaged, a series of tests were run replacing controllers with other samples. The controller parameters were kept the same. In each test, the uncommanded speed changes continued to occur. In one particular test, the system ran for 5:25 hours before a speed change was observed. This speed change was unusual because the motor temperature had climbed to close to 60° C., but then quickly fell after the speed change.

In some embodiments, constant power input into a motor would yield a steady state temperature at some point, given fixed environmental conditions. If the power is increasing while the motor speed remained constant, then the motor torque is increasing. In some embodiments, with an increased motor torque, additional load is present. The major sources of additional load are either magnetic field interactions between the spinning magnets or motor bearings or gears. In some embodiments, as the system exhibits a sudden reduction in power and temperature, motor bearings and gears are not unlikely sources of USCs. In some embodiments, the major cause of the USCs is the system magnets getting "out of phase" with each other, resulting in higher loads. Because all three motors were controlled with closed loop speed controllers, the relative phase relationship between the magnets were controlled very tightly over time. The magnetic fields of the magnets interact with each other, also helping to keep the phase relationship between the magnets. The motors must provide more power if the magnets are not in phase. The closed loop speed controllers are intended to control motor speed very closely, but not motor position. As a result, motor position errors build up over time, causing the magnets to operate out of phase. At some point, the phase error results in either a very high power requirement that the motors cannot match or a state where similar magnetic poles face each other, causing the magnets to repel each other. The result is an instantaneous change in motor speed where the motors return to operate. Motor controller tuning will result in either short periods of time of less than 5 minutes between USCs, or longer times greater than 2 hours. In addition, the magnets tend to re-align when the system is stopped. In some embodiments, additional noise and motor current would show up as the magnets were falling out of sync and the motors required more power to operate.

In some embodiments, the solution to the problem was to control the middle motor with a closed loop controller but use open loop control on the two outer motors. Two sets of protocols were set on durability testing. Protocol 1 was to run the device continuously, but Protocol 2 was configured to run the device for 1 hour and stop for 30 seconds. Over time, both protocols continued to exhibit USCs at varying intervals. Typically, USCs would happen after at least 4-5 hours of run time. Systems running at both protocols also had variable motor currents and sound levels over time. Motor power would seem to surge even though magnet speed was fairly constant. In both protocols, IxR Compensation (IxR Factor=1000, IxR Time Constant=5 ms) was used. In some embodiments, this feature adjusted the motor voltage to compensate for changes in motor resistance with temperature. After completing over 225 hours of run time, a design of experiments (DOE) was used to find an optimum setting to minimize power and reduce the variation. In some embodiments, the IxR Compensation Factor was set to 1 for the two open loop motors. This had the effect of dramatically lowering the variation in motor power as well as the overall magnitude of the power. Testing on both Protocol 1 and Protocol 2 showed that the audible surging was largely gone, and that the motor power remained fairly constant. Protocol 2 showed a reduction in power from cold-start to steady state motor temperature. This was explained by a reduction of mechanical drag in the motor as the grease in the gearbox and bearings heated up.

A design of experiments was performed to optimize the controller settings. An initial screening test confirmed that IxR compensation was a major cause of fluctuations in motor power. The screening test eliminated other variables, allowing for an optimization of the proportional gain for the closed loop motor. The proportional gain is a parameter frequently used in closed loop motor control and will be familiar to one skilled in the art of motor speed control.

In some embodiments, an alternative method of controlling the motors would be to use a synchronized, closed loop position controller for each motor instead of a speed controller. In these embodiments, the motor controllers would position each motor at a particular angle, corresponding to the desired speed. Any position errors would be corrected by the control system before the errors could build up and cause a large increase in motor torque. This was essentially robotic level control applied to each of the three motors. This method of control is feasible with the existing motor controllers on the system.

Non-limiting, exemplary operational motor parameters are provided in Table 1.

In some embodiments, the magnetic field interaction between motor assemblies work in such a way that the torque on the motors increase if the magnets fall out of a preferred synchronization or alignment of magnetic poles. Independently driving the three motors will lead to changes in this synchronization. In further embodiments, closed loop controllers tend to correct for speed errors in a very rigid manner, but allow small synchronization errors to add up over time, leading to very large synchronization errors. In some embodiments, open loop controllers do not control the magnet frequency to an adequate accuracy, however. As a result, a combination of the closed loop and open loop control are needed in some embodiments. By controlling the middle motor in a closed loop manner, but allowing the outer two motors to remain in pure open loop control, the synchronization errors do not build up in some embodiments. In further instances, the closed loop motor maintains a constant speed and the open loop motors allow their speed to follow the closed loop motor. In some embodiments, the magnetic fields interact and enforce the synchronization. In some embodiments, because the open loop motors come close to the desired speed, the closed loop motor does not have to work too hard to maintain a constant speed.

TABLE 1

| Parameter | Motor 1 (top) | Motor 2 (middle) | Motor 3 (front) |
| --- | --- | --- | --- |
| Current Controller Integral Time Constant | 101 us | 101 us | 101 us |
| Current Controller P Gain | 1116 | 1116 | 1116 |
| IxR Factor | 1 | (not used) | 1 |
| IxR Time Constant | 5 ms | (not used) | 5 ms |
| Motor Max. Output Current Limit | 1.5 A | 1.5 A | 1.5 A |

TABLE 1-continued

| Parameter | Motor 1 (top) | Motor 2 (middle) | Motor 3 (front) |
|---|---|---|---|
| Motor Max Permissible Speed | 5000 RPM | 5000 RPM | 5000 RPM |
| Nominal Current | 0.869 A | 0.869 A | 0.869 A |
| Rotor Inertia | 5.550 g * cm^2 | 5.550 g * cm^2 | 5.550 g * cm^2 |
| Speed Constant | 520 RPM/V | 520 RPM/V | 520 RPM/V |
| Terminal Inductance | 0.231 mH | 0.231 mH | 0.231 mH |
| Terminal Resistance | 3.69 Ohm | 3.69 Ohm | 3.69 Ohm |
| Thermal Time Constant Winding | 20.0 s | 20.0 s | 20.0 s |
| Mode of Controller | Reserved | Inner Current Control Loop | Reserved |
| Mode of IxR Compensation | Adaptive IxR Compensation | Reserved | Adaptive IxR Compensation |
| Mode of Operation | Speed Controller (Open Loop) | Speed Controller (Closed Loop) | Speed Controller (Open Loop) |
| Sensor Config - DC Tacho Constant | 0.520 V/1000 RPM | 0.520 V/1000 RPM | 0.520 V/1000 RPM |
| Sensor Config - Encoder Resolution | 1024 Counts/turn | 1024 Counts/turn | 1024 Counts/turn |
| Sensor Config - Sensor Polarity | 0x00 | 0x00 | 0x00 |
| Sensor Config - Speed Sensor | Digital Incremental Encoder | Digital Incremental Encoder | Digital Incremental Encoder |
| Speed Controller Integral Time Constant | (not used) | 375 ms | (not used) |
| Speed Controller P-Gain | (not used) | 50 | (not used) |
| Speed Filter cutoff Frequency | (not used) | 80 Hz | (not used) |
| Speed Ramp Acceleration | 2000 RPM/s | 2000 RPM/s | 2000 RPM/s |
| Speed Ramp Deceleration | 2000 RPM/s | 2000 RPM/s | 2000 RPM/s |
| Speed Ramp Deceleration | 10000 RPM/s | 10000 RPM/s | 10000 RPM/s |

In some embodiments, the platforms, media, methods, and applications described herein include a digital processing device, a processor, or use of the same. In some embodiments, the digital processing device includes one or more hardware central processing units (CPU) that carry out the device's functions. In still some embodiments, the digital processing device comprises an operating system configured to perform executable instructions. In some embodiments, the digital processing device is optionally connected to a computer network. In some embodiments, the digital processing device is optionally connected to the Internet such that it accesses the World Wide Web. In still some embodiments, the digital processing device is optionally connected to a cloud computing infrastructure. In some embodiments, the digital processing device is optionally connected to an intranet. In some embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatus used to store data or programs on a temporary or permanent basis. In some embodiments, the device is volatile memory and requires power to maintain stored information. In some embodiments, the device is non-volatile memory and retains stored information when the digital processing device is not powered. In some embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing based storage. In some embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In some embodiments, the display is a thin film transistor liquid crystal display (TFT-LCD). In some embodiments, the display is an organic light emitting diode (OLED) display. In various some embodiments, on OLED display is a passive-matrix OLED (PMOLED) or active-matrix OLED (AMOLED) display. In some embodiments, the display is a plasma display. In some embodiments, the display is a video projector. In still some embodiments, the display is a combination of devices such as those disclosed herein.

Figure 12:
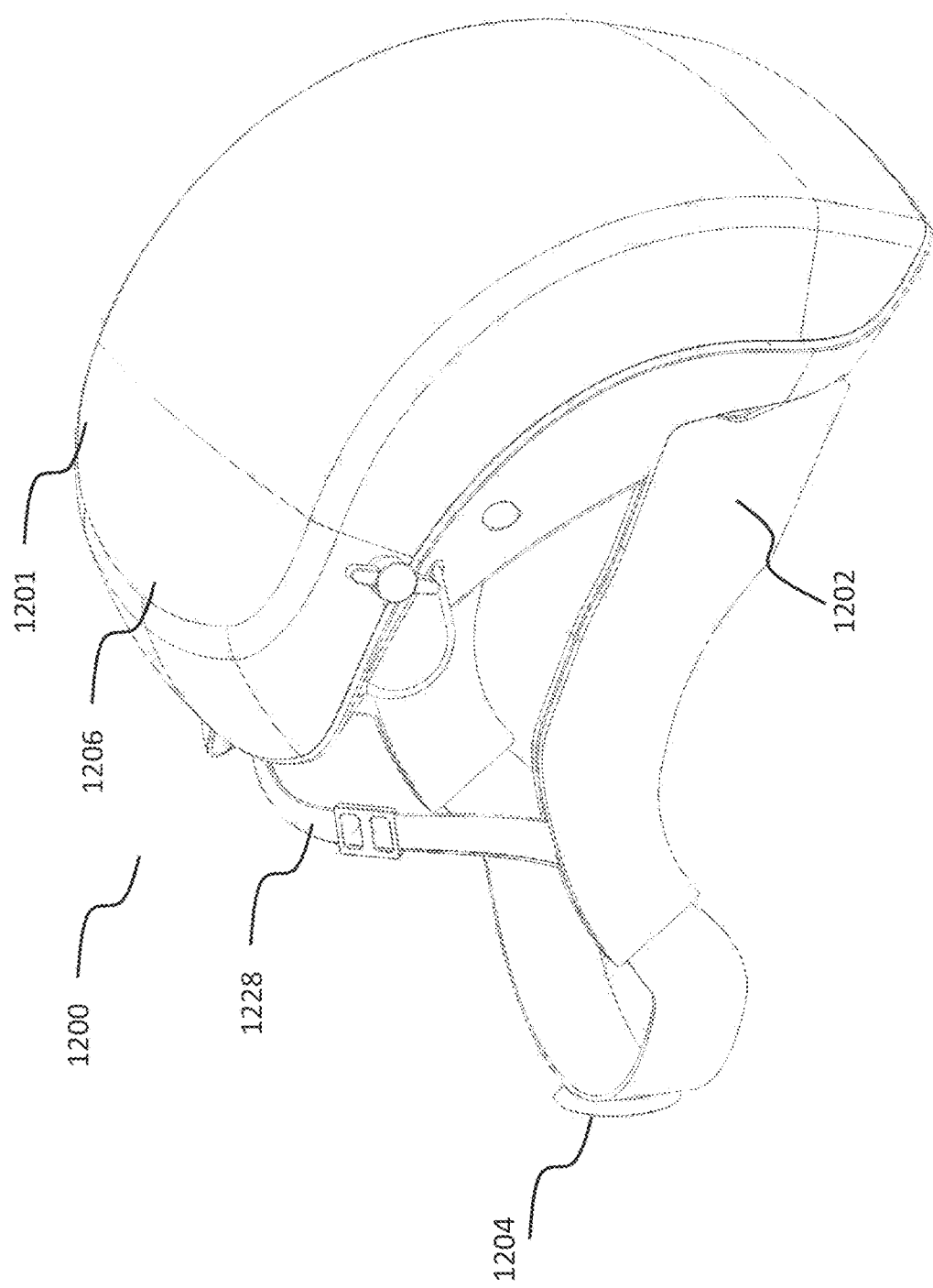
FIG. 12 shows an exemplary embodiment of the head-mountable device.

Referring to FIGS. 12-14, in a particular embodiment, a head-worn device 1200 is configurable to enclose three magnets rotatable by corresponding motors to provide an oscillating magnetic field to the head of the wearer. The device is attached to the head by an adjustable headband 1202 with adjuster 1204 such that one rotating magnet and its assembly 1321a, 1421a is placed on the forehead above the eyebrows, a second magnet is located at approximately the top of the head 1321c, 1421c, and the third magnet 1321b, 11421b is located between the other two. Upon proper wearing of the device, the rotating axes of the magnets are parallel to each other (within manufacturing tolerances) and perpendicular to the patient's medial/lateral plane 426 in FIG. 4. The medial/later plane is within the plane defined by the "y" and "z" axis. Upon proper wearing of the device, the magnets are located such that each magnet is split evenly by the media/lateral plane of the head of the wearer.

In this particular embodiment, one or more of the magnets' location is adjustable to fit different head sizes and shapes. The forehead magnet is fixed to the device housing 1201, but the other two magnets are mounted to pivotable arms 1422a, 1422b that allow for about +/−0.25" (about +/−7.0 mm) of displacement towards/away from the scalp of the wearer. This adjustment is approximately perpendicular to the scalp but the exact angle depends on the shape of the head and where the magnet is located in its range of adjustment.

In some embodiments, the device optionally rotates the magnets at frequencies between about 8 Hz to about 13 Hz. In some embodiments, to minimize undesired magnet vibration, the middle magnet rotates in the opposite direction from the two outer magnets. Referring to a particular instance in FIG. 17, when viewed from the patient's right side, the middle magnet rotates counter-clockwise while the other two magnets rotate clockwise.

In some embodiments, each magnet is driven by a separate motor 1615a. In some embodiments, the motors used herein are brushed DC motors with a single stage planetary gearbox 1624a. In some embodiments, the brushed DC motor generates torque directly from direct circuit (DC) electrical power supplied to the motor by using internal commutation, stationary magnets (permanent or electromagnets), and/or rotating magnets. In some embodiments, a different type of motor could be used, including a brushless DC motor. In some embodiments, a different style of gearbox is used. The planetary gearbox optionally provides an appropriate gear reduction in a smaller space. In some embodiments, the magnets are mounted to the output shaft of the gearbox using a shaft adapter sleeve 1625a. The adapter sleeve optionally adapts a larger inner diameter of the magnets to a shaft with a smaller diameter at its cross-section. Alternatively, a custom-designed gearbox with a larger output shaft or a magnet with a smaller inner diameter should be used without the shaft adapter. In some embodiments, the magnet, shaft, and shaft adapter sleeve are attached together optionally with adhesive. Alternate methods for attaching the shaft including interference fits, clamp collars, welding, etc. are also used. The possible advantage of using adhesive for attachment of the magnets, shaft and adapter sleeve is reduction in space.

In some embodiments, each motor is driven by a separate motor controller. The motor controllers control motor speed, and/or acceleration, but not position. In some embodiments, one or more of the magnets use a controller that utilizes a different controlling mechanism than controllers for the other magnets. More specifically, in some embodiments, the middle motor utilizes a closed-loop controller (feedback controller) that reads the motor speed. In some embodiments, the motor speed is read via a digital encoder or the like. This speed signal is then used by the controller to adjust the speed of the motor to the desired speed. In some embodiments, one or both of the outer two motors utilize an open loop controller. These open-loop controllers use a consistent command for the motor speed and do not use motor speed feedback to adjust this command.

In some embodiments, as the magnets are positioned within a same housing with short distance between them, the magnetic fields of the magnets are strong enough so that the rotational movement of one or more magnets is influenced by magnetic fields generated by other magnets of the same device. In some embodiments, the orientation, position, and/or synchronization of the magnets relative to each other has a low-energy state. In this state, the system of magnets requires a minimum amount of power too spin the magnets at a specific speed. The motors supply between about 0.3 Watts and about 3.5 Watts of power. In some embodiments, maintaining a pre-determined relative orientation of the magnets during their movements in operation of the device herein facilitate minimization of the power needed to drive the motors thus the desired movement of the magnets. In some embodiments, if one or more magnets shift away from this pre-determined relative orientation or synchronization among the magnets, the power required to maintain the proper speed of magnet(s) increases. In further embodiments, if the magnets become highly unsynchronized, the motor and/or motor controller reach a point where they cannot provide sufficient torque to move the magnet(s) at the desired speed. As a result, one or more motors slow down or speed up instantaneously due to the interactions of the magnetic fields. This is not desirable for the treatment.

In some embodiments, the device disclosed herein includes schemes to help avoid losing magnet synchronization. In some embodiments, the open-loop and closed-loop scheme is used for one or more motor controllers to avoid losing magnet synchronization. In particular, the closed-loop controller tightly controls motor speed, but different motor/motor controller combinations will have slightly different speeds over extended periods of time. If all three motors are controlled with closed-loop speed controllers, small position errors would add up, resulting in poor magnet synchronization. For example, a speed difference of about 0.00027% over 4 hours would result in magnets being 180 degrees out of phase. As an alternative, two outer motors are controlled with open-loop controllers, thus the magnetic fields generated by these two outer motors help to keep the motors synchronized. The open-loop controllers used herein allow small speed changes but they prevent synchronization errors from adding up over time. The interaction of magnetic fields between magnets causes the open loop motors to change speed slightly but the interaction works to keep the motors synchronized. Closed loop controllers fight these speed changes and allow synchronization errors to add up over time.

In some embodiments, different methods are also used to prevent loss of magnet synchronization. For example, three motors are controlled with a position controller rather than a speed controller, the device is set to synchronize all three motors and avoid large position errors at each magnet at a specific time point. This has the disadvantage of requiring a more expensive controller. Alternately, a mechanical synchronization mechanism such as a timing belt or a chain is used which optionally increases either the size and/or the weight of the device.

In some instances, the speed or frequency of movement for one or more magnet is not necessarily controlled to be a constant speed at all times. For example, the device is configured to ensure that the frequency at which the north and south poles pass a fixed point is consistent within an error less than 0.1 Hz. However, the system allows the magnet(s) to speed up and slow down slightly in between. As a result, the instantaneous speed or frequency of movement for the motor is not constant.

Figure 11:
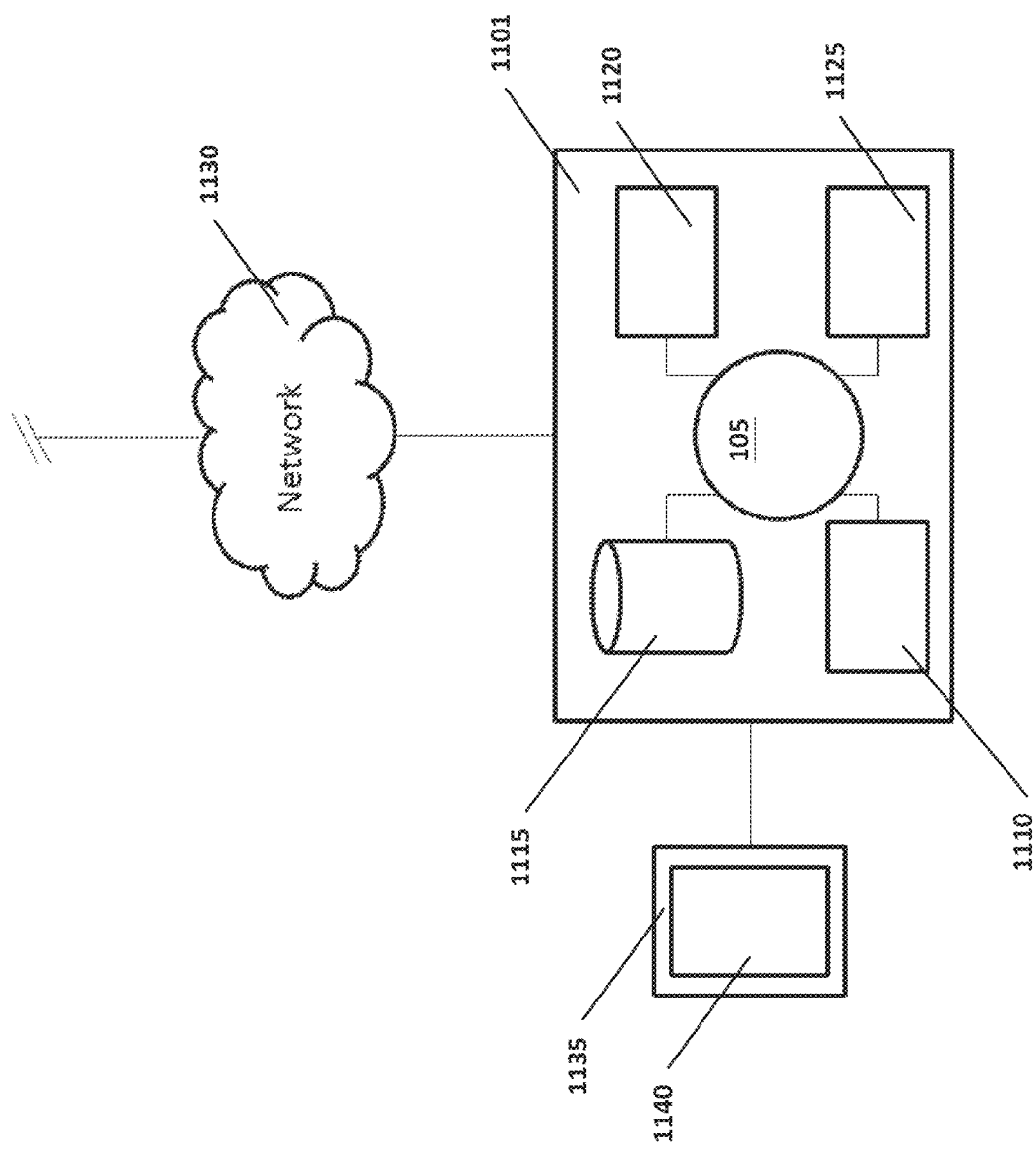
FIG. 11 shows a non-limiting exemplary embodiment of a digital processing device as disclosed herein.

Referring to FIG. 11, in a particular embodiment, an exemplary digital processing device 1101 is programmed or otherwise configured to control adjustment or movement of one or more magnets and/or motors via the fit mechanism semi-automatically or automatically. The device 1101 controls various aspects in the adjustment or movement of one or more magnets. As examples, the device sets an adjustment goal as a distance from an individual magnet to the head, either automatically, or based on user input; the device adjusts the position of an individual magnet based on a feedback received at the device; the device also sets an adjustment increment. As another example, the device also sets rotational frequency, direction, or other aspects of individual magnets. In this embodiment, the digital processing device 1101 includes a central processing unit (CPU, also "processor" and "computer processor" herein) 1105, which is a single core or multi core processor, or a plurality of processors for parallel processing. The digital processing device 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 105 through a communication bus (solid lines), such as a motherboard. The storage unit 1151 is a data storage unit (or data repository) for storing data. The digital processing device 1101 is operatively coupled to a computer network ("network") 1130 with the aid of the communication interface 1120. The network 1130 is the Internet, an internet and/or extranet, or an intranet and/or extranet that is in communication with the Internet. The network 1130 in some embodiments is a telecommunication and/or data network. The network 1130 includes one or more computer servers, which enable distributed computing, such as cloud computing. The network 1130, in some embodiments with the aid of the device 1101, implements a peer-to-peer network, which enables devices coupled to the device 1101 to behave as a client or a server. The digital processing device 1101 is operatively connected to one or more specialized medical devices (not shown) via the network 1130. Such connection enables data collection from the medical device; the data includes subject information, GPS information, EEG data, a predetermined rotational frequency and/or direction of magnet(s), a predetermined position of magnet(s), or other data related to the subject, the helmet, and elements enclosed therein.

Continuing to refer to FIG. 11, the CPU 1105 executes a sequence of machine-readable instructions, which are embodied in a program or software. The instructions are stored in a memory location, such as the memory 1110. The instructions are directed to the CPU 1105, which subsequently programs or otherwise configures the CPU 1105 to implement methods of the present disclosure. Examples of operations performed by the CPU 1105 include fetch, decode, execute, and write back. The CPU 1105 is part of a circuit, such as an integrated circuit. One or more other components of the device 1101 are included in the circuit. In some embodiments, the circuit is an application specific integrated circuit (ASIC) or a field programmable gate array (FPGA).

Continuing to refer to FIG. 11, the storage unit 1115 stores files, such as drivers, libraries and saved programs. The storage unit 1115 stores user data, e.g., user preferences and user programs. The digital processing device 1101 in some embodiments includes one or more additional data storage units that are external, such as located on a remote server that is in communication through an intranet or the Internet.

Continuing to refer to FIG. 11, the digital processing device 1101 communicates with one or more remote computer systems through the network 1130. For instance, the device 1101 communicates with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein are implemented by way of machine (e.g., computer processor) executable code stored on an electronic storage location of the digital processing device 1101, such as, for example, on the memory 1110 or electronic storage unit 1115. In some embodiments, the machine executable or machine readable code are provided in the form of software. In some embodiments, during use, the code is executed by the processor 1105. In some embodiments, the code is retrieved from the storage unit 1115 and stored on the memory 1110 for ready access by the processor 1105. In some situations, the electronic storage unit 1115 is precluded, and machine-executable instructions are stored on memory 1110.

In some embodiments, the platforms, media, methods and applications described herein include one or more non-transitory computer readable storage media encoded with a program including instructions executable by the operating system of an optionally networked digital processing device. In some embodiments, a computer readable storage medium is a tangible component of a digital processing device. In still some embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some embodiments, the program and instructions are permanently, substantially permanently, semi-permanently, or non-transitorily encoded on the media.

In some embodiments, the platforms, media, methods and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions are combined or distributed as desired in various environments. In some embodiments, a computer program comprises one sequence of instructions. In some embodiments, a computer program comprises a plurality of sequences of instructions. In some embodiments, a computer program is provided from one location. In some embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, the platforms, media, methods and applications described herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In some embodiments, software modules are in more than one computer program or application. In some embodiments, software modules are hosted on one machine. In some embodiments, software modules are hosted on more than one machine. In some embodiments, software modules are hosted on cloud computing platforms. In some embodiments, software modules are hosted on one or more machines in one location. In some embodiments, software modules are hosted on one or more machines in more than one location.

In some embodiments, the magnetic field used by the methods or devices are not capable of exciting brain cells. In some embodiments, the magnetic field used by the methods or devices are below thresholds of exciting brain cells. In some embodiments, the devices described have one or more permanent magnets mounted onto one or more rotating shafts in such a way that it creates an alternating magnetic field when the shaft or shafts are spun. In some embodiments, the speed of rotation is set by the user or controlled using neurological feedback to provide optimal therapy.

Methods and devices described herein are used to treat at least one mental disorder listed below:
 (a) Major depression;
 (b) Bipolar disorder;
 (c) Schizophrenia;
 1(d) Anxiety disorder;
 (e) Obsessive-Compulsive disorder;
 (f) ADHD;
 (g) Autism;
 (h) Sleep disorder;
 (j) Parkinson's disease;
 (k) Drug addiction;
 (l) Substance abuse;
 (m) Seizure;
 (n) Head Injury;
 (o) Alzheimer's disease;
 (p) Eating disorder;
 (q) Tinnitus; and
 (r) Fibromyalgia.

In some embodiments, methods and devices described herein are used to treat at least two mental disorders listed above. In some embodiments, methods and devices described herein are used to treat at least three mental disorders listed above. In some embodiments, methods and devices described herein are used to treat at least four mental disorders listed above. In some embodiments, methods and devices described herein are used to treat at least five mental disorders listed above. In some embodiments, methods and devices described herein are used to treat at least six mental disorders listed above. In some embodiments, methods and devices described herein are not used to treat schizophrenia.

Provided herein are methods of treating anxiety in a subject, comprising tuning up the Q-factor of an intrinsic frequency of the subject by applying a magnetic field close to a head of the subject, wherein the magnetic field comprises at least one of (a) a single pre-selected frequency; (b) a plurality of frequencies within a specified EEG band; and (c) an intrinsic frequency of a brain of the subject within a specified EEG band. In some embodiments, any of the devices described herein are used to treat anxiety.

In some embodiments, are method of treating depression in a subject, comprising tuning down the Q-factor of an intrinsic frequency of the subject by applying a magnetic field close to a head of the subject, wherein the magnetic field comprises at least one of (a) a single frequency; (b) a plurality of frequencies within a specified EEG band; and (c) an intrinsic frequency of a brain of the subject within a specified EEG band. In some embodiments, any of the devices described herein are used to treat depression.

In some embodiments, methods and/or devices as described herein are used to treat symptoms of fibromyalgia. In some embodiments, methods and/or devices as described herein are used to improve symptoms of fibromyalgia. For non-limiting example, some symptoms that are improved include widespread pain, tenderness to touch, nausea dizziness, temporomandibular joint dysfunction, skin problems, depression, myofascial pain, morning stiffness, sleep issues, headaches, chemical sensitivity, dysmenorrhea, muscle twitches and weakness, fatigue, urinary and pelvic problems, fibro-fog cognitive and/or memory impairment, anxiety, memory loss, breathing problems, and vision problems.

In some embodiments, methods and/or devices as described herein are used to halt the onset of a seizure. In some embodiments, methods and/or devices as described herein are used to prevent the onset of a seizure. In some embodiments, methods and/or devices as described herein are used to reduce or eliminate seizures by detuning the brain near the frequency of the seizures. In some embodiments, methods and/or devices as described herein are used to reduce or eliminate seizures by tuning up an area of the brain (i.e., an intrinsic frequency in a band, such as alpha) different than the seizure area of the brain, thereby reducing the energy in the frequency associated with the seizure. The seizure is caused by various conditions, diseases, injuries, and/or other factors. For non-limiting example, the conditions include abnormalities in the blood vessels of the brain, atherosclerosis, or hardening of the arteries supplying the brain, bleeding into the brain, such as a subarachnoid hemorrhage, brain tumors, chromosomal abnormalities, congenital diseases or conditions, high blood pressure, pregnancy and problems associated with pregnancy, stroke, transient ischemic attack (mini-stroke). For non-limiting example, the diseases include liver disease, Alzheimer's disease, dementia diseases, epilepsy, nervous system diseases, hereditary diseases, infections involving the brain, encephalitis, brain abscess, bacterial meningitis, kidney failure, and chronic renal failure. For non-limiting example, the injuries include choking, head injuries, electrical injuries, birth injuries, poisonous bites or stings.

Methods and devices described herein are used to improve at least one indication selected from the group of replacement for meditation, quick nap, stress release, attention span, comprehension, memory, lowered blood pressure, increased libido, sports performance, academic performance, and any combination thereof. In some embodiments, methods and devices described herein are used to improve at least two indications from the group presented above. In some embodiments, methods and devices described herein are used to improve at least three indications from the group presented above. In some embodiments, methods and devices described herein are used to improve at least four indications from the group presented above. In some embodiments, methods and devices described herein are used to improve at least five indications from the group presented above. In some embodiments, methods and devices described herein are used to improve at least six indications from the group presented above.

In some embodiments, methods and devices described herein are used to improve at least one indication from the group presented herein, and/or at least one mental disorder listed herein. In some embodiments, methods and devices described herein are used to improve at least one characteristic from the group presented herein, and/or at least one mental disorder listed herein.

Methods and devices described herein are used to improve at least one characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, methods and devices described herein are used to improve at least two indications from the group presented above. In some embodiments, methods and devices described herein are used to improve at least three indications from the group presented above. In some embodiments, methods and devices described herein are used to improve at least four indications from the group presented above. In some embodiments, methods and devices described herein are used to improve at least five indications from the group presented above. In some embodiments, methods and devices described herein are used to improve at least six indications from the group presented above.

Methods and devices described herein are used to provide an improvement to a mental disorder as measured using a rating scale selected from the group consisting of HAMA, HAMD, PANSS, MADRS, BARS, SAS, and any combination thereof. In some embodiments of at least one aspect described above, the method provides an improvement as measured using the Unified Parkinson's Rating Scale. In some embodiments of at least one aspect described above, the method provides an improvement as measured using a modified Unified Parkinson's Rating Scale. The modified Unified Parkinson's Rating Scale includes, for non-limiting example, measuring muscle tone and knee/arm flexibility.

Figure 10:
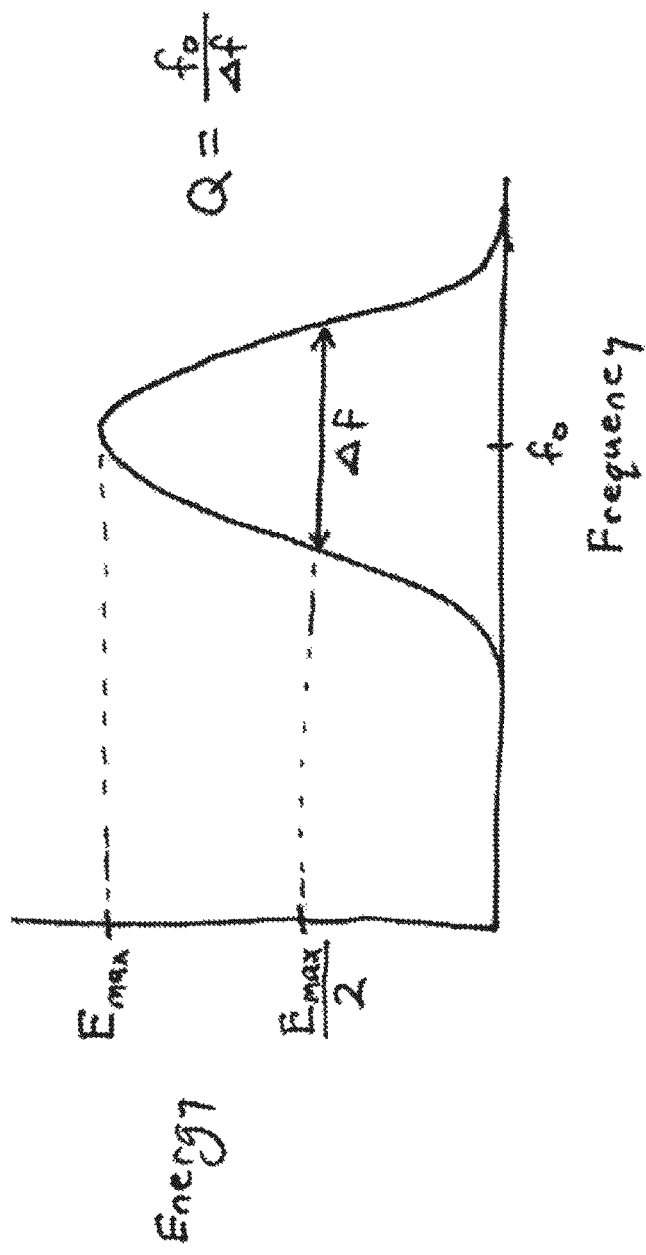
FIG. 10 shows an example of the Q-factor and the intrinsic frequency, in accordance with embodiments.

FIG. 10 shows an example of the Q-factor as disclosed herein. The figure shows a sample graph of the frequency distribution of the energy of an EEG signal. As shown, a frequency range, $\Delta f$ is defined as the frequency bandwidth for which the energy is above one-half the peak energy. The frequency $f_0$ is defined as the intrinsic frequency in the specified band. The Q-factor is defined as the ratio of $f_0/\Delta f$. As shown, when $\Delta F$ decreases for a given $f_0$, the Q-factor will increase. This occurs when the peak energy $E_{max}$ of the signal increases or when the bandwidth of the EEG signal decreases.

In some embodiments, the pre-selected and/or target intrinsic frequency as disclosed herein is any frequency in the range from 0 Hz to 250 Hz. In some case, a target frequency is chosen from one or more intrinsic frequencies in the specified EEG band. In some embodiments, the target intrinsic frequency is chosen from one or more intrinsic frequencies across a plurality of EEG bands. The target frequency is the average frequency calculated using intrinsic frequencies in the specified EEG band of a population of subjects. The target frequency is the average frequency calculated using intrinsic frequencies in more than one EEG bands of a population of subjects. The population is a healthy population or a population with a common physiological character.

In some embodiments, a specified EEG band is the Alpha band, the Beta band, the Gamma band, the Theta band, the Delta band or any other EEG band of a subject.

In some embodiments, the magnetic fields as disclosed herein are not capable of exciting brain cells. In some embodiments, the magnetic fields as disclosed herein are below thresholds of exciting brain cells. In some embodiments, the magnetic fields as disclosed herein does not include a frequency, field strength/intensity, and/or duration that excite brain cells. In some embodiments, the magnetic fields as disclosed herein does not include a frequency, field strength/intensity, and/or duration that excite brain cells outside the preselected areas of the brain. As a non-limiting example, the magnetic field does not have higher frequencies (>10 Hz) that increase cortical excitability. As another example, the magnetic field does not have field intensity greater than about 1 Tesla (10,000 Gauss) to about 2 Tesla (20,000 Gauss). As another example, the magnetic field does not have a pulse train with 1-2 seconds short pulses, and inter-train intervals of about 30 seconds to about 60 seconds.

"Patient" and "subject" are synonyms, and are used interchangeably. As used herein, they mean any animal (e.g. a mammal) on which the inventions described herein is practiced. Neither the term "subject" nor the term "patient" is limited to an animal under the care of a physician.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for applying a magnetic field to a head of a subject, comprising:
    a housing operable to receive at least a portion of the head of the subject, wherein the housing is reversibly transformable between a closed configuration and an open configuration;
    a magnet assembly within the housing comprising: a first permanent magnet, a second permanent magnet, a third permanent magnet, and a first motor coupled to one or more of:
        a first axle of the first permanent magnet, wherein the first axle has a first axis of rotation, and wherein the first axle is operable to drive movement of the first permanent magnet;
        a second axle connected to the second permanent magnet, wherein the second axle has a second axis of rotation, and wherein the second axle is operable to drive movement of the second permanent magnet; or
        a third axle connected to the third permanent magnet, wherein the third axle has a third axis of rotation, wherein the third axle is operable to drive movement of the third permanent magnet;
        wherein two or more of the first axis, the second axis, or the third axis are substantially parallel to each other; and
    a first fit mechanism comprising a first adjuster coupled to the first permanent magnet, wherein movement of the first adjuster moves the first permanent magnet independently of one or more of the second permanent magnet and the third permanent magnet, relative to the housing, and wherein the first adjuster extends outside of the housing when the housing is in the closed configuration such that the first adjuster is operable to be accessible to one or more of a user and the subject when the housing is positioned on the head of the subject.

2. The device of claim 1, wherein the housing comprises a concave surface such that upon placement of the housing on the subject:
    the second permanent magnet is positioned in between the first and the third permanent magnets;
    the first and the third permanent magnets rotate in a first direction; and
    the second permanent magnet rotates in an opposite direction from the first direction.

3. The device of claim 1, wherein the housing comprises an upper part and a lower part, wherein a first portion of the upper part and a first portion of the lower part are connected when the housing is in the closed configuration, and wherein a second portion of the upper part and a second portion of the lower part are not connected when the housing is in the closed configuration.

4. The device of claim 1, wherein the first fit mechanism is operable to reversibly move the first permanent magnet relative to the housing by 0.01 inches to 0.5 inches.

5. The device of claim 1, wherein the first fit mechanism further comprises:
    a fastener attached to the housing, the fastener operable to fasten the first axle and the first permanent magnet at a height;
    a limiter operable to limit an adjustment of the height within a pre-selected range;
    a height measurement sensor operable to measure a distance from the first permanent magnet to the head of the subject when the housing is positioned on the head of the subject;
    a feedback receiver that receives a distance feedback from the height measurement sensor;
    a processor;
    a computer readable media executable by the processor to control the movement of the first adjuster based on the feedback; or
    a combination thereof.

6. The device of claim 1, wherein the first adjuster comprises:
    a knob;
    a lever;
    a buckle with adjustable straps;
    a screw mechanism; or
    a combination thereof.

7. The device of claim 1, wherein a north pole-south pole axes of two or more of said first, second, or third permanent magnets are aligned during rotational movements.

8. The device of claim 1, wherein neutral planes of two or more of said first, second, or third permanent magnets are aligned.

9. The device of claim 1, wherein two or more of said first permanent magnet, said second permanent magnet, or said third permanent magnet are spaced apart from each other by one or more preselected distances, and wherein the one or more preselected distances are adjustable.

10. The device of claim 1, wherein the first fit mechanism is operable to adjust a distance between the first motor and the head of the subject when the housing is positioned on the head of the subject.

11. The device of claim 1, further comprising a second fit mechanism comprising a second adjuster coupled to the second permanent magnet, wherein the second adjuster is operable to be accessible to one or more of the user and the subject when the housing is positioned on the head of the subject, and wherein movement of the second adjuster moves the second permanent magnet independently of one or more of the first permanent magnet and the third permanent magnet, relative to the head of the subject, by a distance of from about 0.1 millimeter to about 50.0 millimeters when the housing is positioned on the head of the subject.

12. The device of claim 11, further comprising a third fit mechanism comprising a third adjuster coupled to the third permanent magnet, wherein the third adjuster is operable to be accessible to one or more of the user and the subject when the housing is positioned on the head of the subject, and wherein movement of the third adjuster moves the third permanent magnet independently of one or more of the first permanent magnet and the second permanent magnet, relative to the head of the subject, by a distance of from about 0.1 millimeter to about 50.0 millimeters when the housing is positioned on the head of the subject.

13. The device of claim 1, further comprising a padding, wherein the padding is operable to be positioned between a concave surface of the housing and the head of the subject.

14. The device of claim 1, further comprising a fastener that is operable to fasten the housing relative to the head of the subject.

15. A system, comprising:
a device comprising:
a housing operable to receive at least a portion of a head of a subject, wherein the housing is reversibly transformable between a closed configuration and an open configuration;
a magnet assembly within the housing comprising: a first permanent magnet, a second permanent magnet, and a third permanent magnet; and
a first fit mechanism comprising a first adjuster coupled to the first permanent magnet, wherein movement of the first adjuster moves the first permanent magnet independently of one or more of the second permanent magnet and the third permanent magnet, relative to the housing, and wherein the first adjuster extends outside of the housing when the housing is in the closed configuration such that the first adjuster is operable to be accessible to one or more of a user and the subject when the housing is positioned on the head of the subject; and
a controller comprising a processor and non-transitory computer readable media, wherein the processor is operable to execute an instruction to control the first fit mechanism of the device using one or more of a wired connection and a wireless connection.

16. The system of claim 15, wherein the controller is not positioned within the housing.

17. The system of claim 15, wherein the controller is not physically attached to the housing.

18. The system of claim 15, wherein the processor is further configured to execute an instruction to cause one or more of:
collecting electroencephalogram (EEG) data of the subject,
receiving the EEG data of the subject,
storing the EEG data of the subject,
calculating an intrinsic frequency using the EEG data of the subject, and
calculating a Q-factor of the intrinsic frequency using the EEG data of the subject.

19. A device, comprising
a housing operable to receive at least a portion of a head of a subject, wherein the housing is reversibly transformable between a closed configuration and an open configuration;
a magnet assembly within the housing comprising:
a first permanent magnet,
a second permanent magnet, and
a third permanent magnet; and
a first fit mechanism comprising a first adjuster coupled to the first permanent magnet, wherein movement of the first adjuster moves the first permanent magnet independently of one or more of the second permanent magnet and the third permanent magnet, relative to the housing, and wherein the first adjuster extends outside of the housing when the housing is in the closed configuration such that the first adjuster is operable to be accessible to one or more of a user and the subject when the housing is positioned on the head of the subject.

20. The device of claim 19, wherein the magnet assembly further comprises a first motor coupled to one or more of:
a first axle of the first permanent magnet, wherein the first axle has a first axis of rotation, and wherein the first axle is operable to drive movement of the first permanent magnet;
a second axle connected to the second permanent magnet, wherein the second axle has a second axis of rotation, and wherein the second axle is operable to drive movement of the second permanent magnet; and
a third axle connected to the third permanent magnet, wherein the third axle has a third axis of rotation, wherein the third axle is operable to drive movement of the third permanent magnet,
wherein two or more of the first axis, the second axis, or the third axis are substantially parallel to each other.

* * * * *